(12) United States Patent
Connolly et al.

(10) Patent No.: US 8,981,117 B2
(45) Date of Patent: Mar. 17, 2015

(54) PROCESSES FOR THE PREPARATION OF ISOINDOLE COMPOUNDS AND ISOTOPOLOGUES THEREOF

(71) Applicant: Celgene Corporation, Summit, NJ (US)

(72) Inventors: Terrence J. Connolly, Warick, NY (US); Alexander L. Ruchelman, Cream Ridge, NJ (US); Kelvin H. Y. Yong, Westfield, NJ (US); Chengmin Zhang, Florham Park, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/026,794

(22) Filed: Sep. 13, 2013

(65) Prior Publication Data

US 2014/0081032 A1    Mar. 20, 2014

Related U.S. Application Data

(60) Provisional application No. 61/701,424, filed on Sep. 14, 2012.

(51) Int. Cl.
| | | |
|---|---|---|
| *C07D 209/46* | (2006.01) | |
| *C07D 209/48* | (2006.01) | |
| *C07C 315/04* | (2006.01) | |

(52) U.S. Cl.
CPC ............ *C07D 209/48* (2013.01); *C07D 209/46* (2013.01); *C07C 315/04* (2013.01)
USPC .......................................... 548/472; 548/473

(58) Field of Classification Search
CPC ...................................................... C07D 209/46
USPC ................................................... 548/472, 473
See application file for complete search history.

(56) References Cited

U.S. PATENT DOCUMENTS

| 6,667,316 B1 | 12/2003 | Man et al. |
| 7,427,638 B2 | 9/2008 | Muller et al. |

FOREIGN PATENT DOCUMENTS

| WO | 2012/097116 A2 | 7/2012 |
| WO | 2013/126495 A2 | 8/2013 |

OTHER PUBLICATIONS

Vippagunta, et al. Advanced Drug Delivery Reviews 48 (2001) 3-26.*

* cited by examiner

*Primary Examiner* — Shawquia Jackson
(74) *Attorney, Agent, or Firm* — Jones Day

(57) ABSTRACT

Processes for the preparation of certain isoindole compounds, and isotopologues thereof, are provided. In some embodiments, the processes comprise catalytic assymetrical hydrogenation with hydrogen gas or deuterium gas in a solvent containing exchangeable proton or deuterium for proton-deuterium exchange.

25 Claims, No Drawings

PROCESSES FOR THE PREPARATION OF ISOINDOLE COMPOUNDS AND ISOTOPOLOGUES THEREOF

This application claims priority to U.S. Provisional Application No. 61/701,424, filed Sep. 14, 2012, the entirety of which is incorporated herein by reference.

1. FIELD

Provided herein are processes for the preparation of certain isoindole compounds, and isotopologues thereof, which are useful for treating, preventing, or managing diseases and conditions including, but not limited to, inflammatory diseases, autoimmune diseases, and cancers.

2. BACKGROUND

Tumor necrosis factor alpha, (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. But TNF-α also has a role in many diseases. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-born tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as but not limited to asthma and inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNF-α and NF-κB. Increased levels of cAMP also leads to the relaxation of airway smooth muscle.

It is believed that the primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150-155, 1990). There are eleven known PDE families. It is recognized, for example, that the inhibition of PDE type IV is particularly effective in both the inhibition of inflammatory mediator release and the relaxation of airway smooth muscle (Verghese, et al., *Journal of Pharmacology and Experimental Therapeutics*, 272(3), 1313-1320, 1995). Thus, compounds that inhibit PDE4 (PDE IV) specifically, may inhibit inflammation and aid the relaxation of airway smooth muscle with a minimum of unwanted side effects, such as cardiovascular or anti-platelet effects. Currently used PDE4 inhibitors lack the selective action at acceptable therapeutic doses.

Cancer is a particularly devastating disease, and increases in blood TNF-α levels are implicated in the risk of and the spreading of cancer. Normally, in healthy subjects, cancer cells fail to survive in the circulatory system, one of the reasons being that the lining of blood vessels acts as a barrier to tumor-cell extravasation. But increased levels of cytokines have been shown to substantially increase the adhesion of cancer cells to endothelium in vitro. One explanation is that cytokines, such as TNF-α, stimulate the biosynthesis and expression of a cell surface receptors called ELAM-1 (endothelial leukocyte adhesion molecule). ELAM-1 is a member of a family of calcium-dependent cell adhesion receptors, known as LEC-CAMs, which includes LECAM-1 and GMP-140. During an inflammatory response, ELAM-1 on endothelial cells functions as a "homing receptor" for leukocytes. Recently, ELAM-1 on endothelial cells was shown to mediate the increased adhesion of colon cancer cells to endothelium treated with cytokines (Rice et al., 1989, *Science* 246:1303-1306).

Inflammatory diseases such as arthritis, related arthritic conditions (e.g., osteoarthritis and rheumatoid arthritis), inflammatory bowel disease (e.g., Crohn's disease and ulcerative colitis), sepsis, psoriasis, atopic dermatitis, contact dermatitis, and chronic obstructive pulmonary disease, chronic inflammatory pulmonary diseases are also prevalent and problematic ailments. TNF-α plays a central role in the inflammatory response and the administration of their antagonists block chronic and acute responses in animal models of inflammatory disease.

Enhanced or unregulated TNF-α production has been implicated in viral, genetic, inflammatory, allergic, and autoimmune diseases. Examples of such diseases include but are not limited to: HIV; hepatitis; adult respiratory distress syndrome; bone-resorption diseases; chronic obstructive pulmonary diseases; chronic pulmonary inflammatory diseases; asthma, dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; ENL in leprosy; radiation damage; asthma; and hyperoxic alveolar injury. Tracey et al., 1987, *Nature* 330:662-664 and Hinshaw et al., 1990, *Circ. Shock* 30:279-292 (endotoxic shock); Dezube et al., 1990, *Lancet*, 335:662 (cachexia); Millar et al., 1989, *Lancet* 2:712-714 and Ferrai-Baliviera et al., 1989, *Arch. Surg.* 124:1400-1405 (adult respiratory distress syndrome); Bertolini et al., 1986, *Nature* 319:516-518, Johnson et al., 1989, *Endocrinology* 124:1424-1427, Holler et al., 1990, *Blood* 75:1011-1016, and Grau et al., 1989, *N. Engl. J. Med.* 320:1586-1591 (bone resorption diseases); Pignet et al., 1990, *Nature*, 344:245-247, Bissonnette et al., 1989, *Inflammation* 13:329-339 and Baughman et al., 1990, *J. Lab. Clin. Med.* 115:36-42 (chronic pulmonary inflammatory diseases); Elliot et al., 1995, *Int. J. Pharmac.* 17:141-145 (rheumatoid arthritis); von Dullemen et al., 1995, *Gastroenterology*, 109: 129-135 (Crohn's disease); Duh et al., 1989, *Proc. Nat. Acad. Sci.* 86:5974-5978, Poll et al., 1990, *Proc. Nat. Acad. Sci.* 87:782-785, Monto et al., 1990, *Blood* 79:2670, Clouse et al., 1989, *J. Immunol.* 142, 431-438, Poll et al., 1992, *AIDS Res. Hum. Retrovirus*, 191-197, Poli et al., 1990, *Proc. Natl. Acad. Sci.* 87:782-784, Folks et al., 1989, *PNAS* 86:2365-2368 (HIV and opportunistic infections resulting from HIV).

Thus, compounds and compositions that can block the activity or inhibit the production of PDE4 or certain cytokines, including TNF-α, may be beneficial as therapeutics. Many small-molecule inhibitors have demonstrated an ability to treat or prevent inflammatory diseases implicated by PDE4 or TNF-α (for a review, see Lowe, 1998 *Exp. Opin. Ther. Patents* 8:1309-1332).

Certain isoindoline compounds, including (S)—N-(2-(1-(3-ethoxy-4-methoxyphenyl)-2-(methylsulfonyl)ethyl)-1,3-dioxoisoindolin-4-yl)acetamide and (S)—N-(2-(1-(3-ethoxy-4-methoxyphenyl)-2-(methylsulfonyl)ethyl)-3- oxoisoindolin-4-yl)cyclopropanecarboxamide, have been reported to be capable of controlling angiogenesis or inhibiting the production of certain cytokines, including TNF-α, and useful in the treatment and prevention of various diseases and conditions. See, e.g., U.S. Pat. Nos. 7,427,638 and 6,667,316, respectively, which are incorporated herein by reference in their entireties.

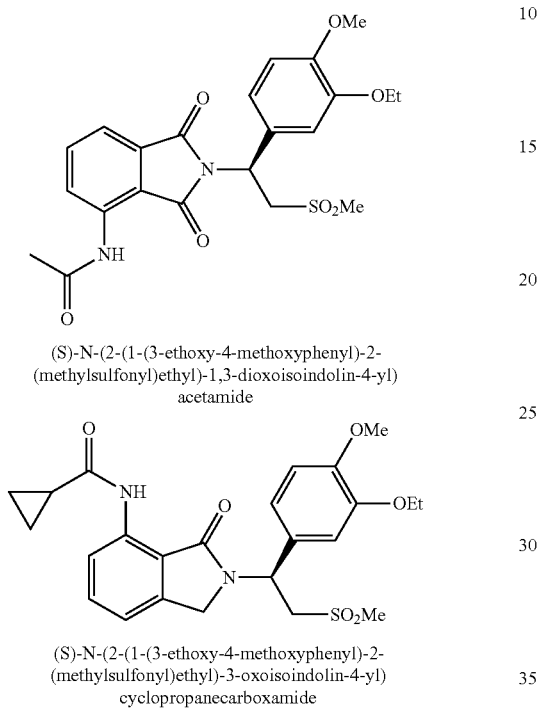

(S)-N-(2-(1-(3-ethoxy-4-methoxyphenyl)-2-(methylsulfonyl)ethyl)-1,3-dioxoisoindolin-4-yl)acetamide (S)-N-(2-(1-(3-ethoxy-4-methoxyphenyl)-2-(methylsulfonyl)ethyl)-3-oxoisoindolin-4-yl)cyclopropanecarboxamide Processes for the preparation of isotopologues of isoindoline compounds, including (S)—N-(2-(1-(3-ethoxy-4-methoxyphenyl)-2-(methylsulfonyl)ethyl)-1,3-dioxoisoindolin-4-yl)acetamide and (S)—N-(2-(1-(3-ethoxy-4-methoxyphenyl)-2-(methylsulfonyl)ethyl)-3-oxoisoindolin-4-yl)cyclopropanecarboxamide, have been reported in International Application Publication No. WO2012/097116, which is incorporated herein by reference in its entirety.

For example, (S)—N-(2-(1-(3-ethoxy-4-methoxyphenyl)-2-(methylsulfonyl)ethyl)-1,3-dioxoisoindolin-4-yl)acetamide enriched with deuterium at its chiral center can be prepared by reacting (S)-aminosulfone 1 with intermediate 2. (S)-aminosulfone 1 can be prepared by resolution of racemic aminosulfone 3 with N—Ac-L-Leu. Racemic aminosulfone 3 can be prepared by reacting 3-ethoxy-4-methoxybenzonitrile 4 with LiCH$_2$SO$_2$CH$_3$, followed by reduction with NaBD$_4$ and borate hydrolysis.

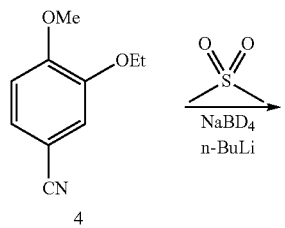

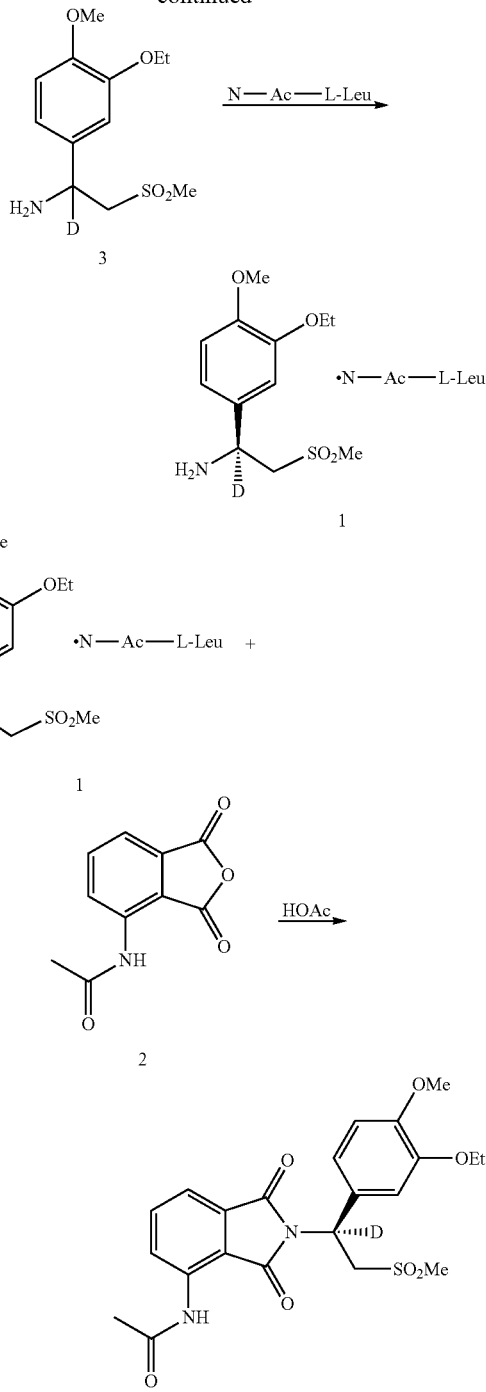

A need exists as to more efficient (e.g., without the need of chiral resolution) processes for the preparation of enantiomerically enriched or enantiomerically pure isoindole compounds and their isotopologues. A need also exists as to processes for the preparation of isotopologues of isoindole compounds, in which the methylene group adjacent to the chiral center is also enriched with isotopes such as deuterium.

3. SUMMARY

Provided herein are processes for the preparation of isoindole compounds, or isotopologues thereof. In one embodiment, provided herein are processes for the preparation of enantiomerically enriched or enantiomerically pure isoindole compounds, or isotopologues thereof, comprising a step of catalytic asymmetrical hydrogenation with hydrogen gas or deuterium gas in a solvent containing exchangeable proton or deuterium for proton-deuterium exchange.

In one embodiment, provided herein is a process for the preparation of an enantiomerically enriched or enantiomerically pure compound of Formula (I):

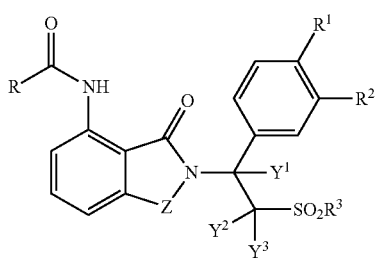

(I)

or a salt, solvate including a hydrate, stereoisomer, isotopologue, or polymorph thereof, wherein:
   $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;
   $R^3$ is $(C_1-C_6)$alkyl, or an isotopologue thereof;
   R is $(C_1-C_3)$alkyl, $(C_3-C_6)$cycloalkyl, or an isotopologue thereof;
   Z is C=O, methylene, or an isotopologue thereof; and
   $Y^1$, $Y^2$, and $Y^3$ are independently hydrogen or deuterium;
comprising the step of
   (a) reducing an enamine of Formula (II):

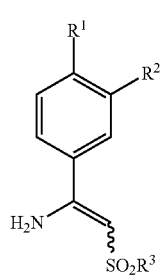

(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

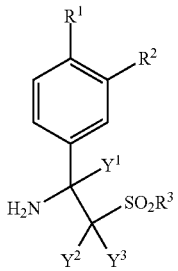

(III)

or a salt or isotopologue thereof.

Also provided herein is a process for the preparation of an enantiomerically enriched or enantiomerically pure aminosulfone compound of Formula (III):

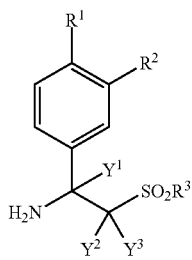

(III)

or a salt, solvate including a hydrate, stereoisomer, isotopologue, or polymorph thereof, wherein:
   $R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;
   $R^3$ is $(C_1-C_6)$alkyl, or an isotopologue thereof; and
   $Y^1$, $Y^2$, and $Y^3$ are independently hydrogen or deuterium;
   wherein not all of $Y^1$, $Y^2$, and $Y^3$ are hydrogen;
comprising the step of
   (a) reducing an enamine of Formula (II):

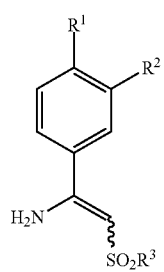

(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III), or a salt or isotopologue thereof, wherein deuterium gas or a solvent containing exchangeable deuterium for proton-deuterium exchange or both is used.

4. DETAILED DESCRIPTION

4.1 Definitions

As used herein, and unless otherwise indicated, the term "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

As used herein, and unless otherwise indicated, the term "isotopically enriched" refers to an atom having an isotopic composition other than the natural isotopic composition of that atom. "Isotopically enriched" may also refer to a compound containing at least one atom having an isotopic composition other than the natural isotopic composition of that atom. As used herein, an "isotopologue" is an isotopically enriched compound.

As used herein, and unless otherwise indicated, the term "isotopic enrichment" refers to the percentage of incorporation of an amount of a specific isotope at a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

As used herein, and unless otherwise indicated, the term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom.

The isotopic enrichment and isotopic enrichment factor of the compounds provided herein can be determined using conventional analytical methods known to one of ordinary skill in the art, including mass spectrometry and nuclear magnetic resonance spectroscopy.

As used herein and unless otherwise indicated, the term "process(es)" provided herein refers to the methods disclosed herein which are useful for preparing a compound provided herein. Modifications to the methods disclosed herein (e.g., starting materials, reagents, protecting groups, solvents, temperatures, reaction times, purification) are also encompassed by the present disclosure.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive groups or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein, and unless otherwise indicated, a reaction that is "substantially complete" or is driven to "substantial completion" means that the reaction contains more than about 80% by percent yield, in one embodiment more than about 90% by percent yield, in another embodiment more than about 95% by percent yield, and in another embodiment more than about 97% by percent yield of the desired product.

As used herein, and unless otherwise indicated, the term "salt" includes, but is not limited to, salts of acidic or basic groups that may be present in the compounds disclosed herein. Compounds that are basic in nature are capable of forming a wide variety of salts with various inorganic and organic acids. The acids that may be used to prepare salts of such basic compounds are those that form salts comprising anions including, but not limited to acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise indicated, the term "hydrate" means a compound or a salt thereof, that further includes a stoichiometric or non-stoichiometeric amount of water bound by non-covalent intermolecular forces.

As used herein, and unless otherwise indicated, the term "solvate" means a solvate formed from the association of one or more solvent molecules to a compound. The term "solvate" includes hydrates (e.g., mono-hydrate, dihydrate, trihydrate, tetrahydrate, and the like).

As used herein, and unless otherwise indicated, the term "polymorph" means solid crystalline forms of a compound or complex thereof. Different polymorphs of the same compound can exhibit different physical, chemical and/or spectroscopic properties.

As used herein, and unless otherwise indicated, the term "halo", "halogen", or the like means —F, —Cl, —Br, or —I.

As used herein, and unless otherwise indicated, the term "alkyl" means a saturated, monovalent, unbranched or branched hydrocarbon chain. Examples of alkyl groups include, but are not limited to, ($C_1$-$C_6$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-butyl, 2-ethyl-1-butyl, butyl, isobutyl, t-butyl, pentyl, isopentyl, neopentyl, and hexyl. Longer alkyl groups include heptyl, octyl, nonyl and decyl groups. An alkyl group can be unsubstituted or substituted with one or more suitable substituents. The alkyl groups may also be isotopologues of the natural abundance alkyl groups by being enriched in isotopes of carbon and/or hydrogen (i.e. deuterium or tritium).

As used herein, and unless otherwise indicated, the term "alkoxy" means an alkyl group that is linked to another group via an oxygen atom (i.e., —O-alkyl). An alkoxy group can be unsubstituted or substituted with one or more suitable substituents. Examples of alkoxy groups include, but are not limited to, ($C_1$-$C_6$)alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, —O-2-ethyl-1-butyl, —O-butyl, —O-isobutyl, —O-t-butyl, —O-pentyl, —O-isopentyl, —O-neopentyl and —O-hexyl. The alkoxy groups may also be isotopologues of the natural abundance alkoxy groups by being enriched in isotopes of carbon, oxygen and/or hydrogen (i.e., deuterium or tritium).

As used herein, and unless otherwise indicated, the term "alcohol" means any compound substituted with an —OH group. The alcohol group may also be isotopologues of the natural abundance alcohol groups by being enriched in isotopes of oxygen and/or hydrogen (i.e., deuterium or tritium).

As used herein, and unless otherwise indicated, the term "amino" or "amino group" means a monovalent group of the formula —$NH_2$, —NH(alkyl), —NH(aryl), —N(alkyl)$_2$, —N(aryl)$_2$ or —N(alkyl)(aryl). The amino groups may also be isotopologues of the natural abundance amino groups by being enriched in isotopes of carbon, nitrogen and/or hydrogen (i.e., deuterium or tritium).

Unless otherwise indicated, the compounds provided herein, including intermediates useful for the preparation of the compounds provided herein, which contain reactive functional groups (such as, without limitation, carboxy, hydroxy, and amino moieties) also include protected derivatives thereof. "Protected derivatives" are those compounds in which a reactive site or sites are blocked with one or more protecting groups (also known as blocking groups). Suitable protecting groups for carboxy moieties include benzyl, t-butyl, and the like as well as isotopologues of the like. Suitable protecting groups for amino and amido groups include acetyl, trifluoroacetyl, t-butyloxycarbonyl, benzyloxycarbonyl, and the like. Suitable protecting groups for hydroxy include benzyl and the like. Other suitable protecting groups are well known to those of ordinary skill in the art. The choice and use of protecting groups and the reaction conditions to install and remove protecting groups are described in T. W. Green, *Protective Groups in Organic Synthesis* (Third Ed., Wiley, New York, 1999), which is incorporated herein by reference in its entirety.

As used herein, and unless otherwise indicated, acronyms or symbols for groups or reagents have the following definition: HPLC=high performance liquid chromatography; TFA=trifluoroacetic acid; TFE=2,2,2-trifluoroethanol, THF=tetrahydrofuran; $CH_3CN$=acetonitrile; HOAc=acetic acid; DCM=dichloromethane.

As used herein, and unless otherwise indicated, the term "substituted" or "substitution," when used to describe a chemical structure or moiety, refers to a derivative of that structure or moiety wherein one or more of its hydrogen atoms is replaced with a substituent such as, but not limited to: alkyl, alkenyl, alkynyl, and cycloalkyl; alkoxyalkyl; aroyl; deuterium, halo; haloalkyl (e.g., trifluoromethyl); heterocloalkyl; haloalkoxy (e.g., trifluoromethoxy); hydroxy; alkoxy; cycloalkyloxy; heterocylooxy; oxo; alkanoyl; aryl; heteroaryl (e.g., indolyl, imidazolyl, furyl, thienyl, thiazolyl, pyrrolidyl, pyridyl, and pyrimidyl); arylalkyl; alkylaryl; heteroaryl; heteroarylalkyl; alkylheteroaryl; heterocyclo; heterocycloalkyl-alkyl; aryloxy, alkanoyloxy; amino; alkylamino; arylamino; arylalkylamino; cycloalkylamino; heterocycloamino; mono- and di-substituted amino; alkanoylamino; aroylamino; aralkanoylamino; aminoalkyl; carbamyl (e.g., $CONH_2$); substituted carbamyl (e.g., CONH-alkyl, CONH-aryl, CONH-arylalkyl or instances where there are two substituents on the nitrogen); carbonyl; alkoxycarbonyl; carboxy; cyano; ester; ether; guanidino; nitro; sulfonyl; alkylsulfonyl; arylsulfonyl; arylalkylsulfonyl; sulfonamido (e.g., $SO_2NH_2$); substituted sulfonamido; thiol; alkylthio; arylthio; arylalkylthio; cycloalkylthio; heterocyclothio; alkylthiono; arylthiono; and arylalkylthiono. In some embodiments, a substituent itself may be substituted with one or more chemical moieties such as, but not limited to, those described herein.

As used herein, and unless otherwise indicated, the term "about" is used to specify that the values given are approximate. For example, the term "about," where it is used in connection with reaction temperatures, denotes that the temperature deviations within 30%, 25%, 20%, 15%, 10%, or 5% are encompassed by the temperature indicated. Similarly, the term "about," where it is used in connection with reaction time, denotes that the time period deviations within 30%, 25%, 20%, 15%, 10%, or 5% are encompassed by the time period indicated.

If the stereochemistry of a structure or a portion thereof is not indicated, e.g., with bold or dashed lines, the structure or portion thereof is to be interpreted as encompassing all enantiomerically pure, enantiomerically enriched, diastereomerically pure, diastereomerically enriched, and racemic mixtures of the compounds.

Unless otherwise indicated, the terms "enantiomerically enriched" and "enantiomerically pure," as used interchangeably herein, refer to compositions in which the percent by weight of one enantiomer is greater than the amount of that one enantiomer in a control mixture of the racemic composition (e.g. greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, and even such as at least 80% by weight. In some embodiments, the enrichment can be much greater than 80% by weight, providing a "substantially optically enriched," "substantially enantiomerically enriched," "substantially enantiomerically pure" or a "substantially non-racemic" preparation, which refers to preparations of compositions which have at least 85% by weight of one enantiomer relative to other enantiomer, such as at least 90% by weight, and such as at least 95% by weight. In some embodiments, the enantiomerically enriched composition has a higher potency with respect to therapeutic utility per unit mass than does the racemic mixture of that composition.

As used herein, and unless otherwise indicated, the term "hydrogenation" refers to a chemical process that adds hydrogen atom, or an isotope thereof (i.e., deuterium or tritium) to an unsaturated bond.

The disclosure can be understood more fully by reference to the following detailed description and illustrative examples, which are intended to exemplify non-limiting embodiments.

Although most embodiments and examples provided herein are directed to the (S)-enantiomer of an aminosulfone or an isoindoline compound, it is to be understood that the corresponding (R)-enantiomer can be prepared by the processes provided herein when the stereochemistry of chiral reactant, reagent, solvent, catalyst, ligand or the like is reversed. It is also to be understood that the corresponding racemic compounds can be prepared by the processes provided herein when the corresponding non-chiral reactant, reagent, solvent, catalyst, ligand or the like is used in place of the chiral reactant, reagent, solvent, catalyst, ligand or the like.

4.2 Processes

Provided herein are processes for the preparation of isoindole compounds, or isotopologues thereof. In one embodiment, provided herein are processes for the preparation of enantiomerically enriched or enantiomerically pure isoindole compounds, or isotopologues thereof.

In one embodiment, provided herein is a process for the preparation of an enantiomerically enriched or enantiomerically pure compound of Formula (I):

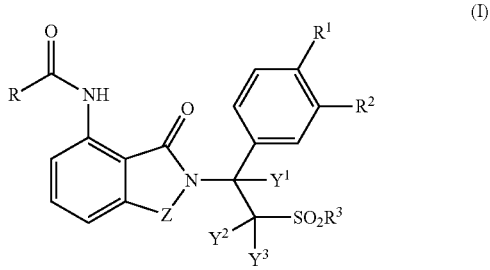

or a salt, solvate including a hydrate, stereoisomer, isotopologue, or polymorph thereof, wherein:

$R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;

$R^3$ is $(C_1-C_6)$alkyl, or an isotopologue thereof;

R is $(C_1-C_3)$alkyl, $(C_3-C_6)$cycloalkyl, or an isotopologue thereof;

Z is C=O, methylene, or an isotopologue thereof; and $Y^1$, $Y^2$, and $Y^3$ are independently hydrogen or deuterium;

comprising the step of
(a) reducing an enamine of Formula (II):

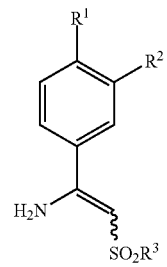

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

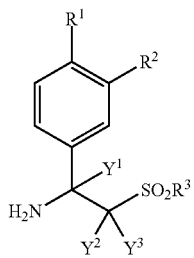

or a salt or isotopologue thereof.

In one embodiment, $R^1$ and $R^2$ are substituted or unsubstituted $(C_1-C_6)$alkoxy, or an isotopologue thereof. In one embodiment, $R^1$ is OMe, or an isotopologue thereof; $R^2$ is OEt, or an isotopologue thereof; and $R^3$ is Me, or an isotopologue thereof. In one embodiment, $R^1$ is OMe enriched with 0, 1, 2, or 3 deuterium; $R^2$ is OEt enriched with 0, 1, 2, 3, 4, or 5 deuterium; and $R^3$ is Me enriched with 0, 1, 2, or 3 deuterium. In one embodiment, $R^1$ is $OCH_3$. In another embodiment, $R^1$ is $OCD_3$. In one embodiment, $R^2$ is $OCH_2CH_3$. In another embodiment, $R^2$ is $OCD_2CD_3$. In one embodiment, $R^1$ is $OCD_3$ and $R^2$ is $OCH_2CH_3$. In another embodiment, $R^1$ is $OCH_3$ and $R^2$ is $OCD_2CD_3$. In yet another embodiment, $R^1$ is $OCD_3$ and $R^2$ is $OCD_2CD_3$.

In one embodiment, $Y^1$ is hydrogen or deuterium, and $Y^2$ and $Y^3$ are both hydrogen or both deuterium. In one embodiment, $Y^1$, $Y^2$ and $Y^3$ are all hydrogen. In another embodiment, $Y^1$ is hydrogen, and $Y^2$ and $Y^3$ are both deuterium. In yet another embodiment, $Y^1$ is deuterium, and $Y^2$ and $Y^3$ are both hydrogen. In yet another embodiment, $Y^1$, $Y^2$ and $Y^3$ are all deuterium.

In one embodiment, $Y^1$ is hydrogen or deuterium, $Y^2$ is hydrogen, and $Y^3$ is deuterium. In another embodiment, $Y^1$ is hydrogen or deuterium, $Y^2$ is deuterium, and $Y^3$ is hydrogen.

In one embodiment of step (a), the hydrogenation occurs to an enamine of Formula (II), or an isotopologue thereof, in free base form. In another embodiment of step (a), the hydrogenation occurs to an enamine of Formula (II), or an isotopologue thereof, in a salt form. In one embodiment, the hydrogenation occurs to an enamine of Formula (II), or an isotopologue thereof, in hydrochloride salt form.

In some embodiments, an enamine of Formula (II), or a salt or isotopologue thereof, may be synthesized based upon the routes described in International Application Publication No.

WO2012/097116, or other techniques known in the art. In one embodiment, an enamine of Formula (II), or a salt or isotopologue thereof, is synthesized by reacting a nitrile of Formula (IV):

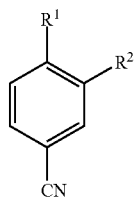
(IV)

or an isotopologue thereof, with $LiCH_2SO_2R^3$, or an isotopologue thereof.

In one embodiment, the enamine of Formula (II), or a salt or isotopologue thereof, is an enamine of Formula (II-a):

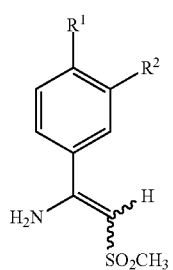
(II-a)

or a salt or isotopologue thereof. In one embodiment, an enamine of Formula (II-a), or a salt or isotopologue thereof, is synthesized by reacting a nitrile of Formula (IV), or an isotopologue thereof, with $CH_3SO_2CH_3$ and n-BuLi.

In one embodiment, the enamine of Formula (II), or a salt or isotopologue thereof, is an enamine of Formula (II-b):

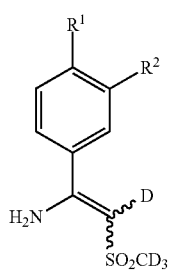
(II-b)

or a salt or isotopologue thereof. In one embodiment, an enamine of Formula (II-b), or a salt or isotopologue thereof, is synthesized by reacting a nitrile of Formula (IV), or an isotopologue thereof, with $CD_3SO_2CD_3$ and n-BuLi.

It is to be understood that an enamine of Formula (II) also refers to its imine tautomer of Formula (II'). In one embodiment, the hydrogenation in step (a) occurs with hydrogen gas. In another embodiment, the hydrogenation in step (a) occurs with deuterium gas.

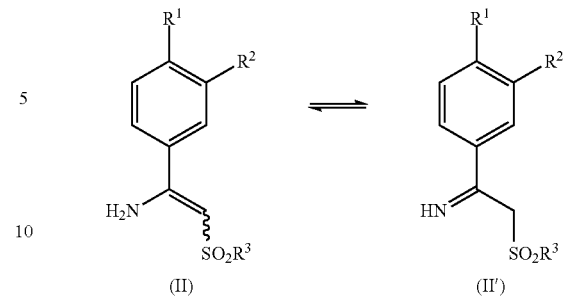

The hydrogenation in step (a) can occur in a solvent, or a mixture of solvents, that is suitable to promote catalytic asymmetric hydrogenation. For example, the hydrogenation in step (a) can occur in a solvent such as, but not limited to, ethyl acetate, diethyl ether, tetrahydrofuran, 1,4-dioxane, acetonitrile, dichloromethane, chloroform, N-methylpyrrolidinone, N,N-dimethyl-formamide, dimethyl sulfoxide, formic acid, acetic acid, methanol, ethanol, isopropanol, 2,2,2-trifluoroethanol, and mixtures and isotopologues thereof.

In one embodiment, the hydrogenation in step (a) occurs in a solvent containing exchangeable deuterium for proton-deuterium exchange. In one embodiment, a —CH— group attached to the sulfone in an enamine of Formula (II) or a —$CH_2$— or —CHD- group attached to the sulfone group in an imine of Formula (II') can undergo proton-deuterium exchange in a solvent containing exchangeable deuterium for proton-deuterium exchange to form a —$CD_2$- group. In one embodiment, the solvent containing exchangeable deuterium for proton-deuterium exchange is 2,2,2-trifluoroethanol-$d^1$ (i.e., $CF_3CH_2OD$ or $d^1$-TFE). In another embodiment, the solvent containing exchangeable deuterium for proton-deuterium exchange is 2,2,2-trifluoroethanol-$d^3$ (i.e., $CF_3CD_2OD$ or $d^3$-TFE).

In one embodiment, the hydrogenation in step (a) occurs in a solvent containing exchangeable proton for proton-deuterium exchange. In one embodiment, a —CD- group attached to the sulfone in an enamine of Formula (II) or a —$CD_2$- or —CHD- group attached to the sulfone group in an imine of Formula (II') can undergo proton-deuterium exchange in a solvent containing exchangeable proton for proton-deuterium exchange to form a —$CH_2$— group. In one embodiment, the solvent containing exchangeable proton for proton-deuterium exchange is 2,2,2-trifluoroethanol (i.e., $CF_3CH_2OH$ or TFE).

In one embodiment of step (a), the hydrogenation is conducted with hydrogen gas in a solvent containing exchangeable proton for proton-deuterium exchange, and the enantiomerically enriched or enantiomerically pure aminosulfone formed is of Formula (III-a):

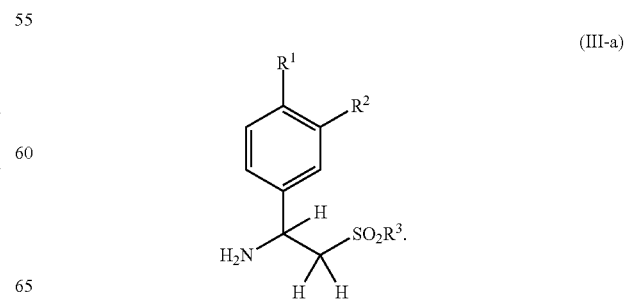
(III-a)

In one embodiment of step (a), the hydrogenation is conducted with deuterium gas in a solvent containing exchangeable proton for proton-deuterium exchange, and the enantiomerically enriched or enantiomerically pure aminosulfone formed is of Formula (III-b):

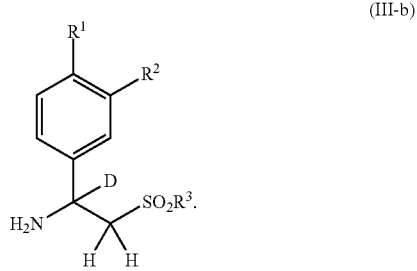

(III-b)

In one embodiment of step (a), the hydrogenation is conducted with hydrogen gas in a solvent containing exchangeable deuterium for proton-deuterium exchange, and the enantiomerically enriched or enantiomerically pure aminosulfone formed is of Formula (III-c):

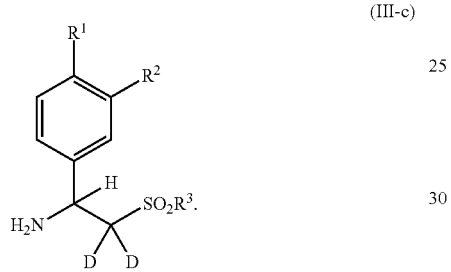

(III-c)

In one embodiment of step (a), the hydrogenation is conducted with deuterium gas in a solvent containing exchangeable deuterium for proton-deuterium exchange, and the enantiomerically enriched or enantiomerically pure aminosulfone formed is of Formula (III-d):

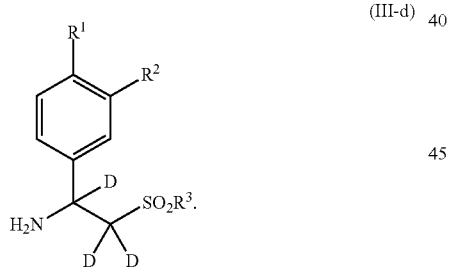

(III-d)

In one embodiment, provided herein is a process for the preparation of an enantiomerically enriched or enantiomerically pure compound of Formula (I):

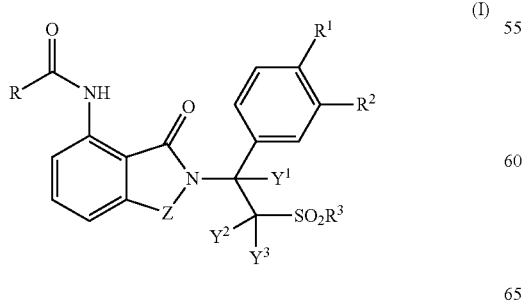

(I)

or a salt, solvate including a hydrate, stereoisomer, isotopologue, or polymorph thereof, wherein:

$R^1$ and $R^2$ are each independently hydrogen, halogen, substituted or unsubstituted $(C_1\text{-}C_6)$alkyl, substituted or unsubstituted $(C_1\text{-}C_6)$alkoxy, $(C_3\text{-}C_{18})$cycloalkyl, $(C_3\text{-}C_6)$cycloalkoxy, cyano, —$CF_3$, $(C_3\text{-}C_{18})$cycloalkyl-$(C_1\text{-}C_6)$alkoxy, or an isotopologue thereof;

$R^3$ is $(C_1\text{-}C_6)$alkyl, or an isotopologue thereof;

R is $(C_1\text{-}C_3)$alkyl, $(C_3\text{-}C_6)$cycloalkyl, or an isotopologue thereof;

Z is C=O, methylene, or an isotopologue thereof; and $Y^1$, $Y^2$, and $Y^3$ are independently hydrogen or deuterium; wherein not all of $Y^1$, $Y^2$, and $Y^3$ are hydrogen;

comprising the step of (a) reducing an enamine of Formula (II):

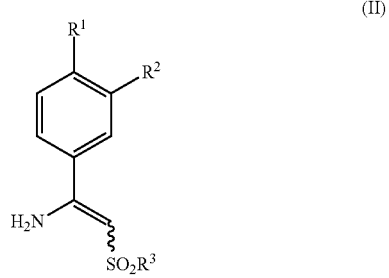

(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

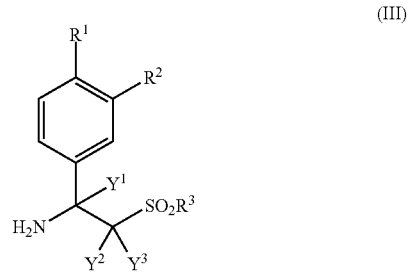

(III)

or a salt or isotopologue thereof; wherein deuterium gas or a solvent containing exchangeable deuterium for proton-deuterium exchange or both is used.

In one embodiment, provided herein is a process for the preparation of an enantiomerically enriched or enantiomerically pure compound of Formula (I):

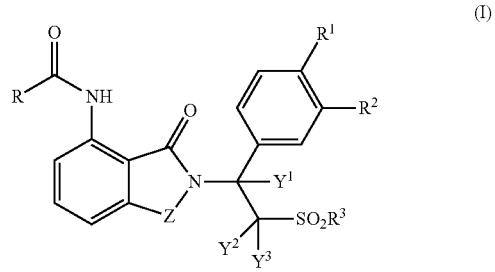

(I)

or a salt, solvate including a hydrate, stereoisomer, isotopologue, or polymorph thereof, wherein:

$R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;

$R^3$ is $(C_1-C_6)$alkyl, or an isotopologue thereof;

R is $(C_1-C_3)$alkyl, $(C_3-C_6)$cycloalkyl, or an isotopologue thereof;

Z is C=O, methylene, or an isotopologue thereof;

$Y^1$ is hydrogen or deuterium; and $Y^2$ and $Y^3$ are both deuterium;

comprising the step of (a) reducing an enamine of Formula (II):

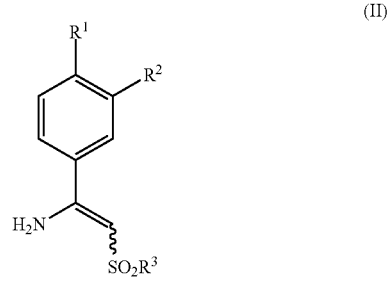

(II)

or a salt or isotopologue thereof, via hydrogenation with hydrogen gas or deuterium gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III):

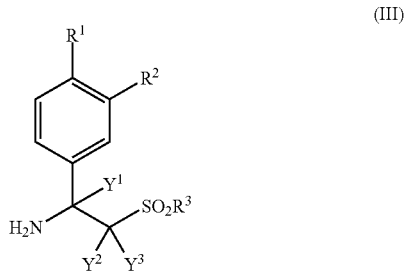

(III)

or a salt or isotopologue thereof.

The metal catalyst can be any metal catalyst that is capable of promoting hydrogenation. In one embodiment, the metal catalyst contains a metal such as, but not limited to, copper, nickel, palladium, platinum, rhodium, iridium, and ruthenium. In one embodiment, the metal catalyst contains rhodium. In another embodiment, the metal catalyst contains ruthenium. In yet another embodiment, the metal catalyst contains iridium. In one embodiment, the metal catalyst is $Rh(cod)_2OTf$. In another embodiment, the metal catalyst is $Rh(cod)_2BF_4$. In yet another embodiment, the metal catalyst is $[Ir(cod)Cl]_2$.

The chiral ligand or chiral metal catalyst/ligand complex can be any chiral ligand or chiral metal catalyst/ligand complex that is capable of promoting asymmetric hydrogenation. In one embodiment, the chiral ligand or chiral metal catalyst/ligand complex is, but not limited to, (S,R)-t-Bu Josiphos, Josiphos SL-J011-2, (S,S)-Me-Duphos, (S,S)-Chiraphos, (R)-Phanephos, (R)—$Ru(OAc)_2$(DM-segphos), [(R,R)-Me-BPE]$Rh(cod)BF_4$, (R)—$C_3$-TunePhos, (R)-[Rh(cod)TCFP]$BF_4$, or a stereoisomer thereof. In one embodiment, the chiral ligand is (S,R)-t-Bu Josiphos or Josiphos SL-J011-2. In one embodiment, the chiral ligand is (S,R)-t-Bu Josiphos. In another embodiment, the chiral ligand is Josiphos SL-J011-2. In another embodiment, the chiral ligand is (R,S)-t-Bu Josiphos.

The hydrogenation can occur with a load of catalyst no less than about 0.025 mol %. In general, the higher the load of catalyst, the higher the conversion and the shorter the reaction time. However, when the load of catalyst is sufficiently high, the yield of desired product may decrease due to competing side reactions. In one embodiment, the load of catalyst is between about 0.025 mol % and about 20 mol %. In one embodiment, the load of catalyst is between about 0.025 mol % and about 10 mol %. In one embodiment, the load of catalyst is between about 0.05 mol % and about 5 mol %. In one embodiment, the load of catalyst is between about 0.05 mol % and about 2.5 mol %. In one embodiment, the load of catalyst is between about 0.05 mol % and about 1 mol %. In one embodiment, the load of catalyst is between about 0.05 mol % and about 0.25 mol %. In one embodiment, the load of catalyst is about 5 mol %. In another embodiment, the load of catalyst is about 1 mol %. In yet another embodiment, the load of catalyst is about 0.25 mol %.

The molar ratio of the chiral ligand to the metal catalyst can be any ratio that is capable of promoting hydrogenation. In one embodiment, the molar ratio of the chiral ligand to the metal catalyst is from about 3:1 to about 1:3. In one embodiment, the molar ratio of the chiral ligand to the metal catalyst is from about 3:1 to about 1:1. In one embodiment, the molar ratio of the chiral ligand to the metal catalyst is about 2:1. In another embodiment, the molar ratio of the chiral ligand to the metal catalyst is about 1:1.

The hydrogenation can occur under a hydrogen (or deuterium) pressure between about 1 psia and about 550 psia. In general, the higher the hydrogen pressure, the shorter is the reaction time. In one embodiment, the hydrogen pressure is between about 15 psig and about 250 psig. In one embodiment, the hydrogen pressure is between about 15 psig and about 90 psig. In another embodiment, the hydrogen pressure is between about 90 psig and about 250 psig. In one embodiment, the hydrogen pressure is about 15 psig. In another embodiment, the hydrogen pressure is about 90 psig. In yet another embodiment, the hydrogen pressure is about 250 psig.

The reaction temperature for the hydrogenation can be between about 10° C. and about 90° C. In one embodiment, the reaction temperature is between about 40° C. and about 60° C. In one embodiment, the reaction temperature is about 50° C.

The reaction time for the hydrogenation can vary from about 1 to about 72 hours, depending on the reaction temperature and the hydrogen pressure. In general, the higher the reaction temperature and the higher the hydrogen pressure, the shorter is the reaction time.

In one embodiment, R is $(C_1-C_3)$alkyl, or an isotopologue thereof. In one embodiment, R is methyl, or an isotopologue thereof. In one embodiment, R is methyl enriched with 0, 1, 2, or 3 deuterium.

4.2.1 Preparation of Isoindolin-1,3-dione Compounds

In one embodiment, provided herein is a process for the preparation of an enantiomerically enriched or enantiomerically pure compound of Formula (I-a):

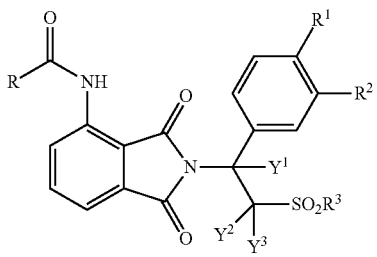

(I-a)

or a salt, solvate including a hydrate, stereoisomer, isotopologue, or polymorph thereof, wherein:
  $R^1$ and $R^2$ are each independently hydrogen, halogen, substituted or unsubstituted $(C_1$-$C_6)$alkyl, substituted or unsubstituted $(C_1$-$C_6)$alkoxy, $(C_3$-$C_{18})$cycloalkyl, $(C_3$-$C_6)$cycloalkoxy, cyano, —$CF_3$, $(C_3$-$C_{18})$cycloalkyl-$(C_1$-$C_6)$alkoxy, or an isotopologue thereof;
  $R^3$ is $(C_1$-$C_6)$alkyl, or an isotopologue thereof;
  R is $(C_1$-$C_3)$alkyl, $(C_3$-$C_6)$cycloalkyl, or an isotopologue thereof; and
  $Y^1$, $Y^2$, and $Y^3$ are independently hydrogen or deuterium;
comprising the steps of
  (a) reducing an enamine of Formula (II):

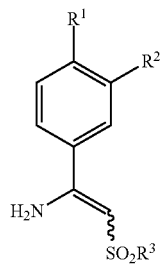

(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

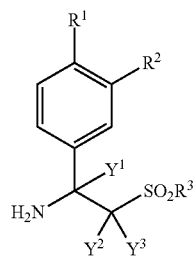

(III)

or a salt or isotopologue thereof; and
  (b) reacting the enantiomerically enriched or enantiomerically pure aminosulfone of Formula (III), or a salt or isotopologue thereof, with a compound of Formula (V):

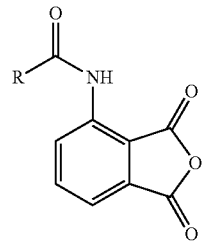

(V)

or a salt or isotopologue thereof, to form the enantiomerically enriched or enantiomerically pure compound of Formula (I-a), or a salt or isotopologue thereof.

In one embodiment, provided herein is a process for the preparation of an enantiomerically enriched or enantiomerically pure compound of Formula (I-a):

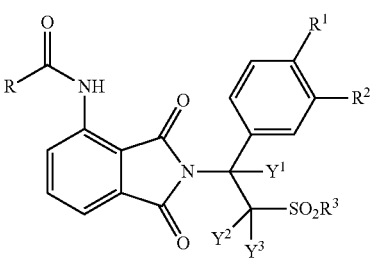

(I-a)

or a salt, solvate including a hydrate, stereoisomer, isotopologue, or polymorph thereof, wherein:
  $R^1$ and $R^2$ are each independently hydrogen, halogen, substituted or unsubstituted $(C_1$-$C_6)$alkyl, substituted or unsubstituted $(C_1$-$C_6)$alkoxy, $(C_3$-$C_{18})$cycloalkyl, $(C_3$-$C_6)$cycloalkoxy, cyano, —$CF_3$, $(C_3$-$C_{18})$cycloalkyl-$(C_1$-$C_6)$alkoxy, or an isotopologue thereof;
  $R^3$ is $(C_1$-$C_6)$alkyl, or an isotopologue thereof;
  R is $(C_1$-$C_3)$alkyl, $(C_3$-$C_6)$cycloalkyl, or an isotopologue thereof; and
  $Y^1$, $Y^2$, and $Y^3$ are independently hydrogen or deuterium; wherein not all of $Y^1$, $Y^2$, and $Y^3$ are hydrogen;
comprising the steps of
  (a) reducing an enamine of Formula (II):

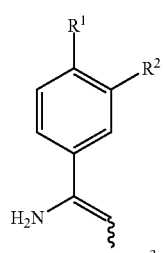

(II)

or a salt or isotopologue thereof, via hydrogenation with hydrogen gas or deuterium gas, in a solvent, and in the presence of (i) a metal catalyst and a chiral ligand or (2) a chiral metal catalyst/ligand complex to form an enantiomerically enriched or enantiomerically pure aminosulfone of Formula (III):

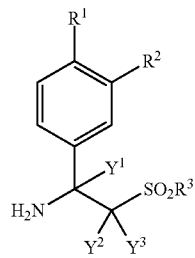
(III)

or a salt or isotopologue thereof; wherein deuterium gas or a solvent containing exchangeable deuterium for proton-deuterium exchange or both is used; and (b) reacting the enantiomerically enriched or enantiomerically pure aminosulfone of Formula (III), or a salt or isotopologue thereof, with a compound of Formula (V):

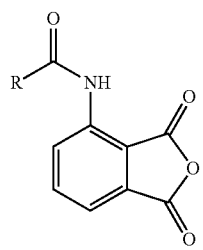
(V)

or a salt or isotopologue thereof, to form the enantiomerically enriched or enantiomerically pure compound of Formula (I-a), or a salt or isotopologue thereof.

In one embodiment, provided herein is a process for the preparation of an enantiomerically enriched or enantiomerically pure compound of Formula (I-a):

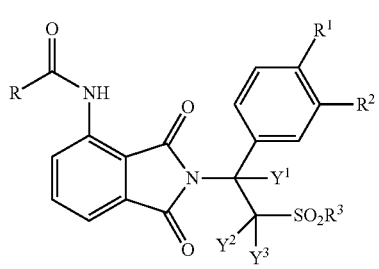
(I-a)

or a salt, solvate including a hydrate, stereoisomer, isotopologue, or polymorph thereof, wherein:

$R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;

$R^3$ is $(C_1-C_6)$alkyl, or an isotopologue thereof;

R is $(C_1-C_3)$alkyl, $(C_3-C_6)$cycloalkyl, or an isotopologue thereof;

$Y^1$ is hydrogen or deuterium; and $Y^2$ and $Y^3$ are both deuterium;

comprising the steps of
(a) reducing an enamine of Formula (II):

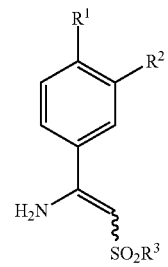
(II)

or a salt or isotopologue thereof, via hydrogenation with hydrogen gas or deuterium gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III):

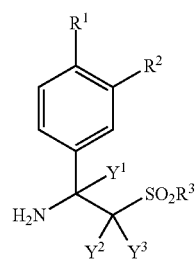
(III)

or a salt or isotopologue thereof; and (b) reacting the enantiomerically enriched or enantiomerically pure aminosulfone of Formula (III), or a salt or isotopologue thereof, with a compound of Formula (V):

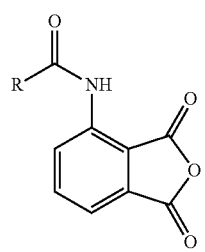
(V)

or a salt or isotopologue thereof, to form the enantiomerically enriched or enantiomerically pure compound of Formula (I-a), or a salt or isotopologue thereof.

In one embodiment, R is $(C_1-C_3)$alkyl, or an isotopologue thereof. In one embodiment, R is methyl, or an isotopologue thereof. In one embodiment, R is methyl enriched with 0, 1, 2, or 3 deuterium. In one embodiment, R is $CD_3$.

Step (a) is as described herein and elsewhere above.

In some embodiments of step (b), the reaction of the enantiomerically enriched or enantiomerically pure aminosulfone of Formula (III), or a salt or isotopologue thereof, with a compound of Formula (V), or a salt or isotopologue thereof, may be conducted based upon the routes described in International Application Publication No. WO2012/097116 and U.S. Pat. No. 6,962,940, the entireties of which are incorporated herein by reference. In one embodiment of step (b), the reaction occurs in a solvent (e.g., acetic acid) via heating (e.g., refluxing).

In one embodiment, provided herein is a process for the preparation of an enantiomerically enriched or enantiomerically pure compound of Formula (I-a-1):

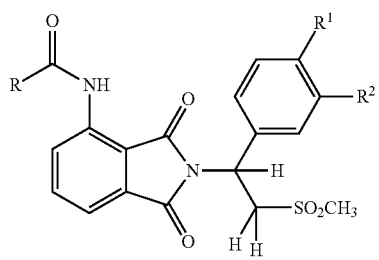

(I-a-1)

or a salt, solvate including a hydrate, stereoisomer, isotopologue, or polymorph thereof, wherein:
R$^1$ is OMe enriched with 0, 1, 2, or 3 deuterium;
R$^2$ is OEt enriched with 0, 1, 2, 3, 4, or 5 deuterium; and
R is methyl enriched with 0, 1, 2, or 3 deuterium;
comprising the steps of
(a) reducing an enamine of Formula (II-a):

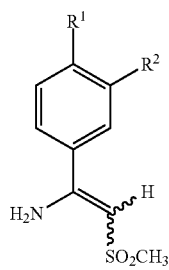

(II-a)

or a salt or isotopologue thereof, via hydrogenation with hydrogen gas, in a solvent not containing exchangeable deuterium (including a solvent containing exchangeable proton for proton-deuterium exchange, such as TFE), and in the presence of (1) a metal catalyst and a chiral ligand or (2) a chiral metal catalyst/ligand complex to form an enantiomerically enriched or enantiomerically pure aminosulfone of Formula (III-1):

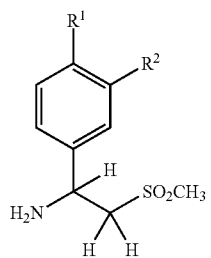

(III-1)

or a salt or isotopologue thereof; and
(b) reacting the enantiomerically enriched or enantiomerically pure aminosulfone of Formula (III-1), or a salt or isotopologue thereof, with a compound of Formula (V):

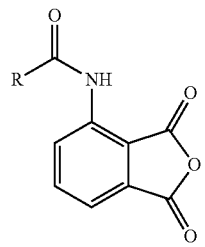

(V)

or a salt or isotopologue thereof, to form the enantiomerically enriched or enantiomerically pure compound of Formula (I-a-1), or a salt or isotopologue thereof.

In one embodiment, provided herein is a process for the preparation of an enantiomerically enriched or enantiomerically pure compound of Formula (I-a-2):

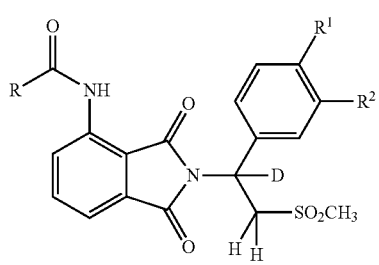

(I-a-2)

or a salt, solvate including a hydrate, stereoisomer, isotopologue, or polymorph thereof, wherein:
R$^1$ is OMe enriched with 0, 1, 2, or 3 deuterium;
R$^2$ is OEt enriched with 0, 1, 2, 3, 4, or 5 deuterium; and
R is methyl enriched with 0, 1, 2, or 3 deuterium;
comprising the steps of
(a) reducing an enamine of Formula (II-a):

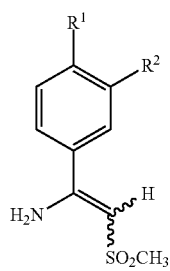

(II-a)

or a salt or isotopologue thereof, via hydrogenation with deuterium gas, in a solvent containing exchangeable proton for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-2):

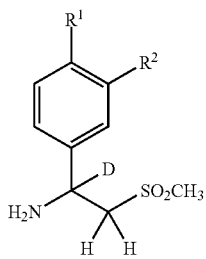

or a salt or isotopologue thereof; and (b) reacting the enantiomerically enriched or enantiomerically pure aminosulfone of Formula (III-2), or a salt or isotopologue thereof, with a compound of Formula (V):

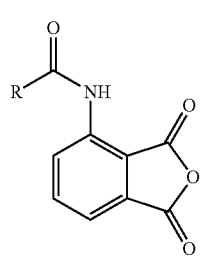

or a salt or isotopologue thereof, to form the enantiomerically enriched or enantiomerically pure compound of Formula (I-a-2), or a salt or isotopologue thereof.

In one embodiment, provided herein is a process for the preparation of an enantiomerically enriched or enantiomerically pure compound of Formula (I-a-3):

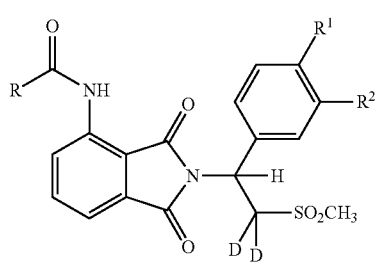

or a salt, solvate including a hydrate, stereoisomer, isotopologue, or polymorph thereof, wherein:

$R^1$ is OMe enriched with 0, 1, 2, or 3 deuterium;
$R^2$ is OEt enriched with 0, 1, 2, 3, 4, or 5 deuterium; and
R is methyl enriched with 0, 1, 2, or 3 deuterium;

comprising the steps of (a) reducing an enamine of Formula (II-a):

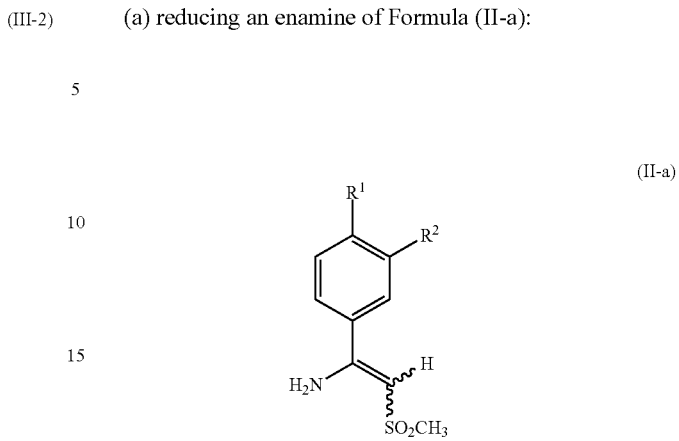

or a salt or isotopologue thereof, via hydrogenation with hydrogen gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-3):

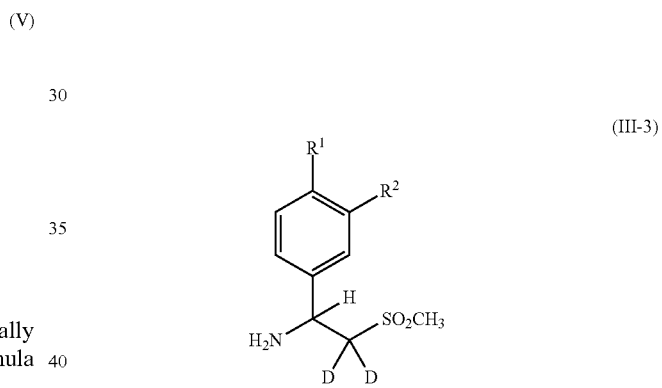

or a salt or isotopologue thereof; and (b) reacting the enantiomerically enriched or enantiomerically pure aminosulfone of Formula (III-3), or a salt or isotopologue thereof, with a compound of Formula (V):

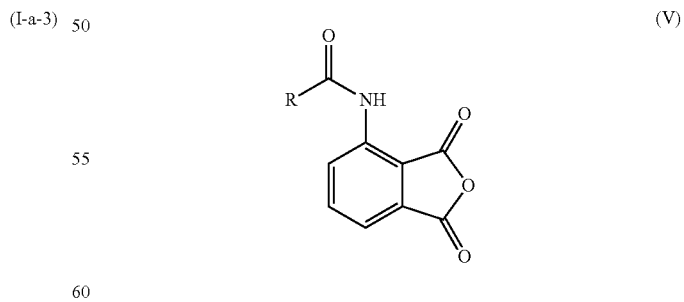

or a salt or isotopologue thereof, to form the enantiomerically enriched or enantiomerically pure compound of Formula (I-a-3), or a salt or isotopologue thereof.

In one embodiment, provided herein is a process for the preparation of an enantiomerically enriched or enantiomerically pure compound of Formula (I-a-4):

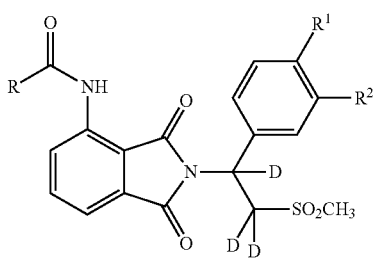
(I-a-4)

or a salt, solvate including a hydrate, stereoisomer, isotopologue, or polymorph thereof, wherein:

$R^1$ is OMe enriched with 0, 1, 2, or 3 deuterium;

$R^2$ is OEt enriched with 0, 1, 2, 3, 4, or 5 deuterium; and

R is methyl enriched with 0, 1, 2, or 3 deuterium;

comprising the steps of (a) reducing an enamine of Formula (II-a):

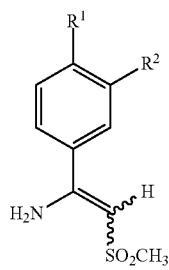
(II-a)

or a salt or isotopologue thereof, via hydrogenation with deuterium gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-4):

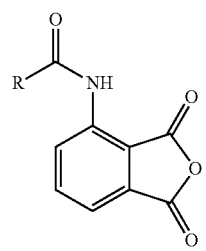
(III-4)

or a salt or isotopologue thereof; and (b) reacting the enantiomerically enriched or enantiomerically pure aminosulfone of Formula (III-4), or a salt or isotopologue thereof, with a compound of Formula (V):

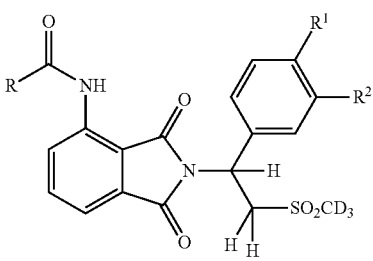
(V)

or a salt or isotopologue thereof, to form the enantiomerically enriched or enantiomerically pure compound of Formula (I-a-4), or a salt or isotopologue thereof.

In one embodiment, provided herein is a process for the preparation of an enantiomerically enriched or enantiomerically pure compound of Formula (I-a-5):

(I-a-5)

or a salt, solvate including a hydrate, stereoisomer, isotopologue, or polymorph thereof, wherein:

$R^1$ is OMe enriched with 0, 1, 2, or 3 deuterium;

$R^2$ is OEt enriched with 0, 1, 2, 3, 4, or 5 deuterium; and

R is methyl enriched with 0, 1, 2, or 3 deuterium;

comprising the steps of (a) reducing an enamine of Formula (II-b):

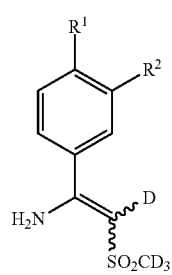
(II-b)

or a salt or isotopologue thereof, via hydrogenation with hydrogen gas, in a solvent containing exchangeable proton for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-5):

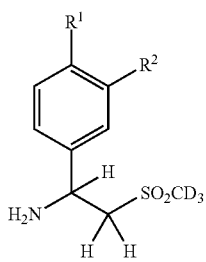

(III-5)

or a salt or isotopologue thereof; and (b) reacting the enantiomerically enriched or enantiomerically pure aminosulfone of Formula (III-5), or a salt or isotopologue thereof, with a compound of Formula (V):

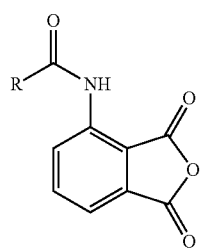

(V)

or a salt or isotopologue thereof, to form the enantiomerically enriched or enantiomerically pure compound of Formula (I-a-5), or a salt or isotopologue thereof.

In one embodiment, provided herein is a process for the preparation of an enantiomerically enriched or enantiomerically pure compound of Formula (I-a-6):

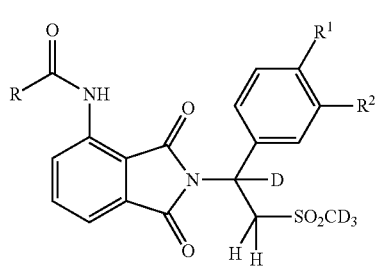

(I-a-6)

or a salt, solvate including a hydrate, stereoisomer, isotopologue, or polymorph thereof, wherein:

R¹ is OMe enriched with 0, 1, 2, or 3 deuterium;
R² is OEt enriched with 0, 1, 2, 3, 4, or 5 deuterium; and
R is methyl enriched with 0, 1, 2, or 3 deuterium;

comprising the steps of (a) reducing an enamine of Formula (II-b):

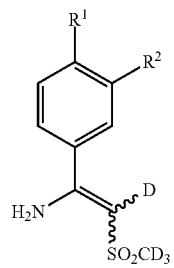

(II-b)

or a salt or isotopologue thereof, via hydrogenation with deuterium gas, in a solvent containing exchangeable proton for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-6):

(III-6)

or a salt or isotopologue thereof; and (b) reacting the enantiomerically enriched or enantiomerically pure aminosulfone of Formula (III-6), or a salt or isotopologue thereof, with a compound of Formula (V):

(V)

or a salt or isotopologue thereof, to form the enantiomerically enriched or enantiomerically pure compound of Formula (I-a-6), or a salt or isotopologue thereof.

In one embodiment, provided herein is a process for the preparation of an enantiomerically enriched or enantiomerically pure compound of Formula (I-a-7):

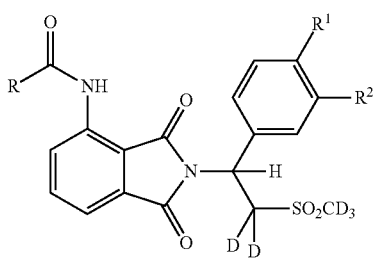

(I-a-7)

or a salt, solvate including a hydrate, stereoisomer, isotopologue, or polymorph thereof, wherein:

$R^1$ is OMe enriched with 0, 1, 2, or 3 deuterium;

$R^2$ is OEt enriched with 0, 1, 2, 3, 4, or 5 deuterium; and

R is methyl enriched with 0, 1, 2, or 3 deuterium;

comprising the steps of (a) reducing an enamine of Formula (II-b):

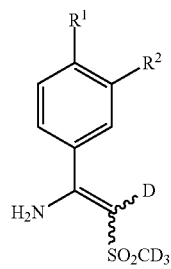

(II-b)

or a salt or isotopologue thereof, via hydrogenation with hydrogen gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-7):

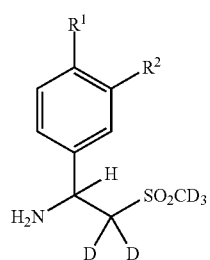

(III-7)

or a salt or isotopologue thereof; and (b) reacting the enantiomerically enriched or enantiomerically pure aminosulfone of Formula (III-7), or a salt or isotopologue thereof, with a compound of Formula (V):

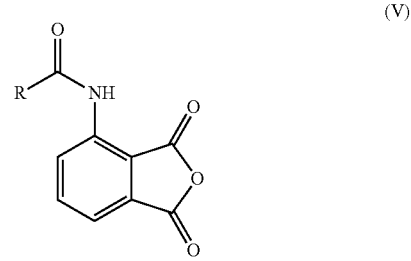

(V)

or a salt or isotopologue thereof, to form the enantiomerically enriched or enantiomerically pure compound of Formula (I-a-7), or a salt or isotopologue thereof.

In one embodiment, provided herein is a process for the preparation of an enantiomerically enriched or enantiomerically pure compound of Formula (I-a-8):

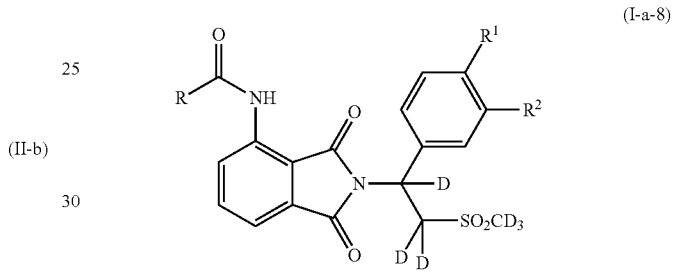

(I-a-8)

or a salt, solvate including a hydrate, stereoisomer, isotopologue, or polymorph thereof, wherein:

$R^1$ is OMe enriched with 0, 1, 2, or 3 deuterium;

$R^2$ is OEt enriched with 0, 1, 2, 3, 4, or 5 deuterium; and

R is methyl enriched with 0, 1, 2, or 3 deuterium;

comprising the steps of (a) reducing an enamine of Formula (II-b):

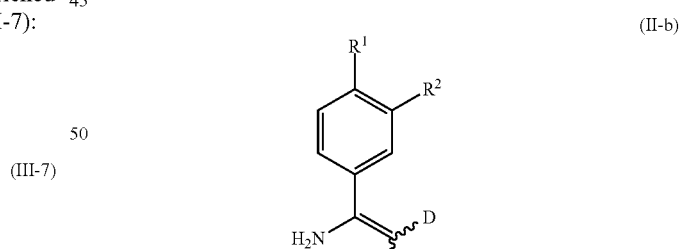

(II-b)

or a salt or isotopologue thereof, via hydrogenation with deuterium gas, in a solvent not containing exchangeable proton (including a solvent containing exchangeable deuterium for proton-deuterium exchange, such as $d_1$-TFE), and in the presence of (1) a metal catalyst and a chiral ligand or (2) a chiral metal catalyst/ligand complex to form an enantiomerically enriched or enantiomerically pure aminosulfone of Formula (III-8):

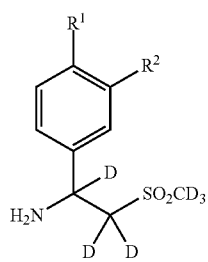
(III-8)

or a salt or isotopologue thereof; and (b) reacting the enantiomerically enriched or enantiomerically pure aminosulfone of Formula (III-8), or a salt or isotopologue thereof, with a compound of Formula (V):

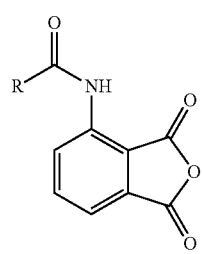
(V)

or a salt or isotopologue thereof, to form the enantiomerically enriched or enantiomerically pure compound of Formula (I-a-8), or a salt or isotopologue thereof.

In one embodiment, an enantiomerically enriched or enantiomerically pure compound of Formula (I-a), or an isotopologue thereof, is a compound A:

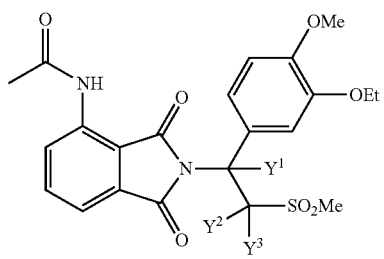
A or an isotopologue thereof.

4.2.2 Preparation of Isoindolin-1-one Compounds

In one embodiment, provided herein is a process for the preparation of an enantiomerically enriched or enantiomerically pure compound of Formula (I-b):

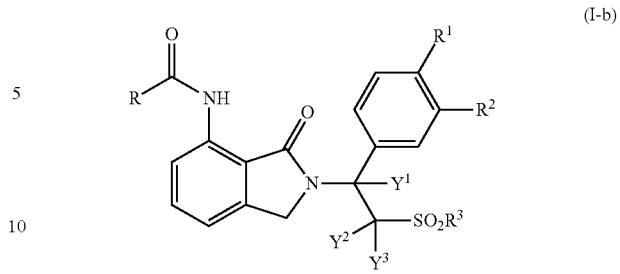
(I-b)

or a salt, solvate including a hydrate, stereoisomer, isotopologue, or polymorph thereof, wherein:

$R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;

$R^3$ is $(C_1-C_6)$alkyl, or an isotopologue thereof;

R is $(C_1-C_3)$alkyl, $(C_3-C_6)$cycloalkyl, or an isotopologue thereof; and $Y^1$, $Y^2$, and $Y^3$ are independently hydrogen or deuterium;

comprising the steps of (a) reducing an enamine of Formula (II):

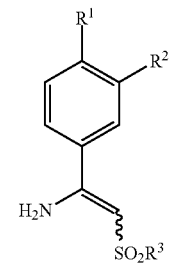
(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

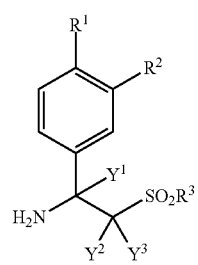
(III)

or a salt or isotopologue thereof;

(b) reacting the enantiomerically enriched or enantiomerically pure aminosulfone of Formula (III), or a salt or isotopologue thereof, with a compound of Formula (VI):

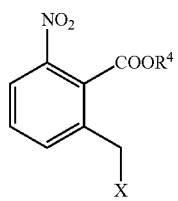

or a salt or isotopologue thereof, wherein R⁴ is $(C_1$-$C_3)$alkyl, and X is halogen, to form an enantiomerically enriched or enantiomerically pure compound of Formula (VII):

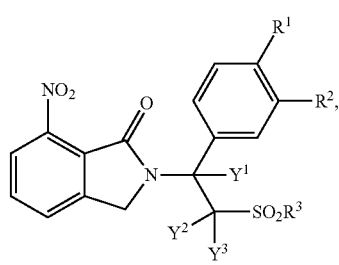

or a salt or isotopologue thereof.

(c) reducing the enantiomerically enriched or enantiomerically pure compound of Formula (VII), or a salt or isotopologue thereof, to form an enantiomerically enriched or enantiomerically pure compound of Formula (VIII):

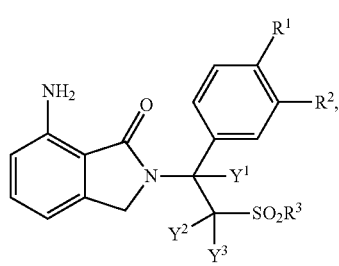

or a salt or isotopologue thereof; and (d) reacting the enantiomerically enriched or enantiomerically pure compound of Formula (VIII), or a salt or isotopologue thereof, with an acid chloride RCOCl, or an isotopologue thereof, to form the enantiomerically enriched or enantiomerically pure compound of Formula (I-b), or a salt or isotopologue thereof.

In one embodiment, provided herein is a process for the preparation of an enantiomerically enriched or enantiomerically pure compound of Formula (I-b):

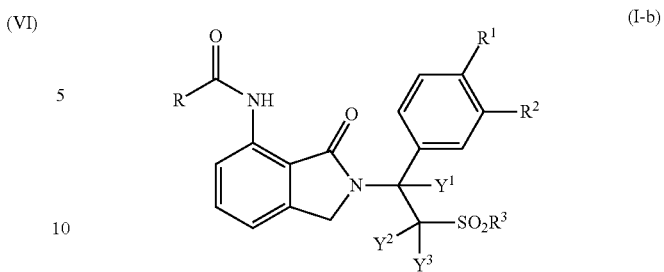

or a salt, solvate including a hydrate, stereoisomer, isotopologue, or polymorph thereof, wherein:

$R^1$ and $R^2$ are each independently hydrogen, halogen, substituted or unsubstituted $(C_1$-$C_6)$alkyl, substituted or unsubstituted $(C_1$-$C_6)$alkoxy, $(C_3$-$C_{18})$cycloalkyl, $(C_3$-$C_6)$cycloalkoxy, cyano, —CF₃, $(C_3$-$C_{18})$cycloalkyl-$(C_1$-$C_6)$alkoxy, or an isotopologue thereof;

$R^3$ is $(C_1$-$C_6)$alkyl, or an isotopologue thereof;

R is $(C_1$-$C_3)$alkyl, $(C_3$-$C_6)$cycloalkyl, or an isotopologue thereof; and $Y^1$, $Y^2$, and $Y^3$ are independently hydrogen or deuterium; wherein not all of $Y^1$, $Y^2$, and $Y^3$ are hydrogen;

comprising the steps of (a) reducing an enamine of Formula (II):

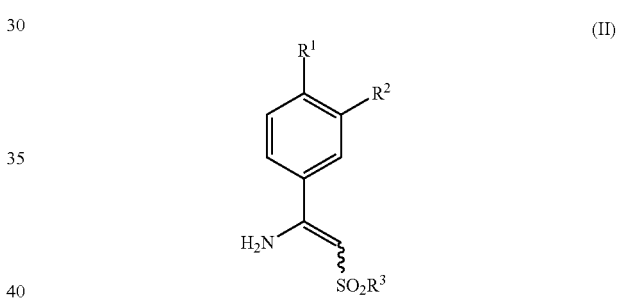

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

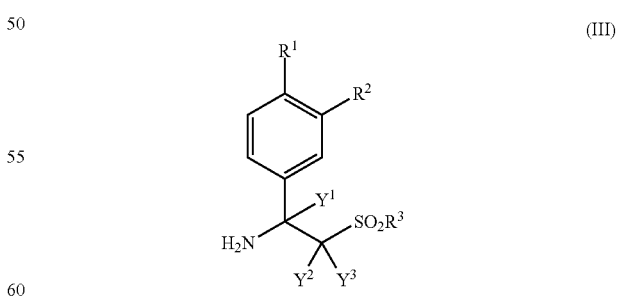

or a salt or isotopologue thereof; wherein deuterium gas or a solvent containing exchangeable deuterium for proton-deuterium exchange or both is used;

(b) reacting the enantiomerically enriched or enantiomerically pure aminosulfone of Formula (III), or a salt or isotopologue thereof, with a compound of Formula (VI):

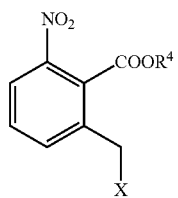
(VI)

or a salt or isotopologue thereof, wherein $R^4$ is $(C_1$-$C_3)$alkyl, and X is halogen, to form an enantiomerically enriched or enantiomerically pure compound of Formula (VII):

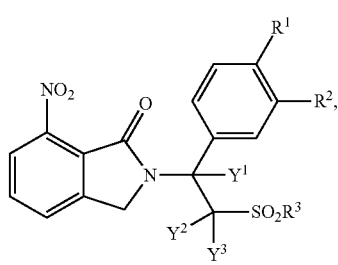
(VII)

or a salt or isotopologue thereof;

(c) reducing the enantiomerically enriched or enantiomerically pure compound of Formula (VII), or a salt or isotopologue thereof, to form an enantiomerically enriched or enantiomerically pure compound of Formula (VIII):

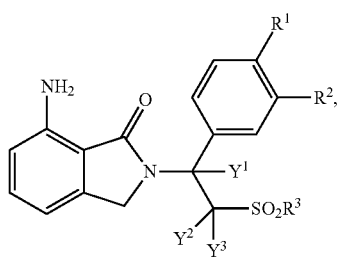
(VIII)

or a salt or isotopologue thereof; and (d) reacting the enantiomerically enriched or enantiomerically pure compound of Formula (VIII), or a salt or isotopologue thereof, with an acid chloride RCOCl, or an isotopologue thereof, to form the enantiomerically enriched or enantiomerically pure compound of Formula (I-b), or a salt or isotopologue thereof.

In one embodiment, provided herein is a process for the preparation of an enantiomerically enriched or enantiomerically pure compound of Formula (I-b):

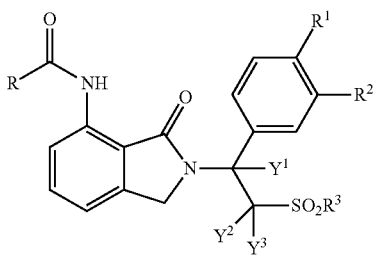
(I-b)

or a salt, solvate including a hydrate, stereoisomer, isotopologue, or polymorph thereof, wherein:
$R^1$ and $R^2$ are each independently hydrogen, halogen, substituted or unsubstituted $(C_1$-$C_6)$alkyl, substituted or unsubstituted $(C_1$-$C_6)$alkoxy, $(C_3$-$C_{18})$cycloalkyl, $(C_3$-$C_6)$cycloalkoxy, cyano, —$CF_3$, $(C_3$-$C_{18})$cycloalkyl-$(C_1$-$C_6)$alkoxy, or an isotopologue thereof;
$R^3$ is $(C_1$-$C_6)$alkyl, or an isotopologue thereof;
R is $(C_1$-$C_3)$alkyl, $(C_3$-$C_6)$cycloalkyl, or an isotopologue thereof;
$Y^1$ is hydrogen or deuterium; and
$Y^2$ and $Y^3$ are both deuterium;
comprising the steps of
(a) reducing an enamine of Formula (II):

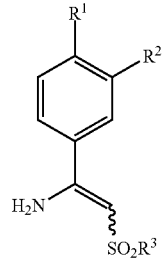
(II)

or a salt or isotopologue thereof, via hydrogenation with hydrogen gas or deuterium gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III):

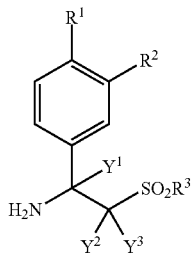
(III)

or a salt or isotopologue thereof;
(b) reacting the enantiomerically enriched or enantiomerically pure aminosulfone of Formula (III), or a salt or isotopologue thereof, with a compound of Formula (VI):

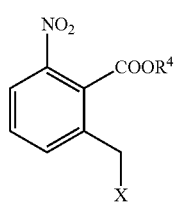

(VI)

or a salt or isotopologue thereof, wherein $R^4$ is $(C_1-C_3)$alkyl, and X is halogen, to form an enantiomerically enriched or enantiomerically pure compound of Formula (VII):

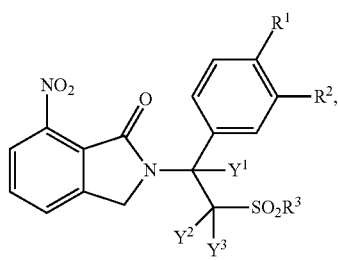

(VII)

or a salt or isotopologue thereof;

(c) reducing the enantiomerically enriched or enantiomerically pure compound of Formula (VII), or a salt or isotopologue thereof, to form an enantiomerically enriched or enantiomerically pure compound of Formula (VIII):

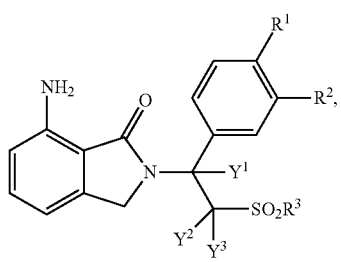

(VIII)

or a salt or isotopologue thereof; and (d) reacting the enantiomerically enriched or enantiomerically pure compound of Formula (VIII), or a salt or isotopologue thereof, with an acid chloride RCOCl, or an isotopologue thereof, to form the enantiomerically enriched or enantiomerically pure compound of Formula (I-b), or a salt or isotopologue thereof.

In one embodiment, R is $(C_3-C_6)$cycloalkyl, or an isotopologue thereof. In one embodiment, R is cyclopropyl, or an isotopologue thereof. In one embodiment, R is cyclopropyl enriched with 0, 1, 2, 3, 4, or 5 deuterium. In one embodiment, R is cyclopropyl enriched with 5 deterium.

Step (a) is described as herein and elsewhere above.

In some embodiments of step (b), the reaction of the enantiomerically enriched or enantiomerically pure aminosulfone of Formula (III), or a salt or isotopologue thereof, with a compound of Formula (VI), or a salt or isotopologue thereof, may be conducted based upon the routes described in International Application Publication No. WO2012/097116 and U.S. Pat. Nos. 6,667,316, 6,020,358, and 7,034,052, the entireties of which are incorporated herein by reference. In one embodiment of step (b), $R^4$ is methyl or ethyl, and X is bromo. In one embodiment of step (b), the reaction occurs in a solvent (e.g., DMF) via heating (e.g., about 100° C.) in the presence of a base (e.g., triethylamine).

In some embodiments of step (c), the reduction of the enantiomerically enriched or enantiomerically pure compound of Formula (VII), or a salt or isotopologue thereof, may be conducted based upon the routes described in International Application Publication No. WO2012/097116 and U.S. Pat. Nos. 6,667,316, 6,020,358, and 7,034,052. In one embodiment of step (c), the reduction occurs via hydrogenation in a solvent (e.g., ethyl acetate) in the presence of a metal catalyst (e.g., Pd/C).

In some embodiments of step (d), the reaction of the enantiomerically enriched or enantiomerically pure compound of Formula (VIII), or a salt or isotopologue thereof, with an acid chloride RCOCl, or an isotopologue thereof, may be conducted based upon the routes described in International Application Publication No. WO2012/097116 and U.S. Pat. Nos. 6,667,316, 6,020,358, and 7,034,052. In one embodiment of step (d), the reaction occurs in a solvent (e.g., DMF) in the presence of a base (e.g., triethylamine).

In one embodiment, provided herein is a process for the preparation of an enantiomerically enriched or enantiomerically pure compound of Formula (I-b-1):

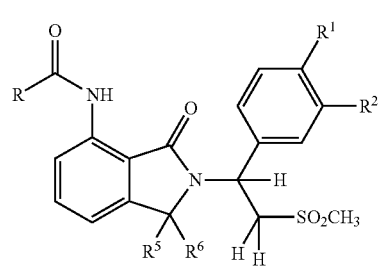

(I-b-1)

or a salt, solvate including a hydrate, stereoisomer, isotopologue, or polymorph thereof, wherein:

$R^1$ is OMe enriched with 0, 1, 2, or 3 deuterium;
$R^2$ is OEt enriched with 0, 1, 2, 3, 4, or 5 deuterium;
$R^5$ and $R^6$ are independently hydrogen or deuterium; and
R is cyclopropyl enriched with 0, 1, 2, 3, 4, or 5 deuterium;

comprising the steps of (a) reducing an enamine of Formula (III-a):

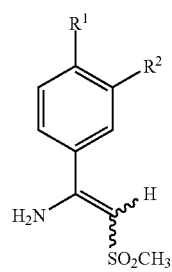

(II-a)

or a salt or isotopologue thereof, via hydrogenation with hydrogen gas, in a solvent not containing exchangeable deuterium (including a solvent containing exchangeable proton for proton-deuterium exchange, such as TFE), and in the presence of (1) a metal catalyst and a chiral ligand or (2) a chiral metal catalyst/ligand complex to form an enantiomerically enriched or enantiomerically pure aminosulfone of Formula (III-1):

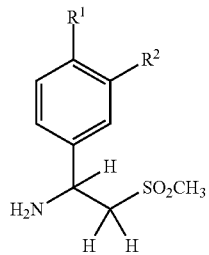

(III-1)

or a salt or isotopologue thereof;

(b) reacting the enantiomerically enriched or enantiomerically pure aminosulfone of Formula (III-1), or a salt or isotopologue thereof, with a compound of Formula (VI-a):

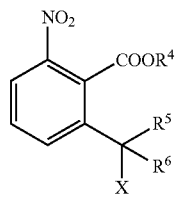

(VI-a)

or a salt or isotopologue thereof, wherein $R^4$ is $(C_1-C_3)$alkyl, and X is halogen, to form an enantiomerically enriched or enantiomerically pure compound of Formula (VIII-1):

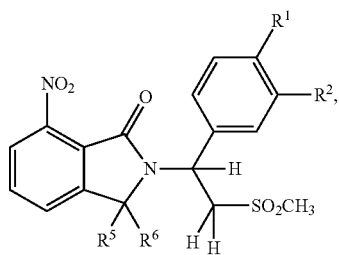

(VIII-1)

or a salt or isotopologue thereof;

(c) reducing the enantiomerically enriched or enantiomerically pure compound of Formula (VIII-1), or a salt or isotopologue thereof, to form an enantiomerically enriched or enantiomerically pure compound of Formula (IX-1):

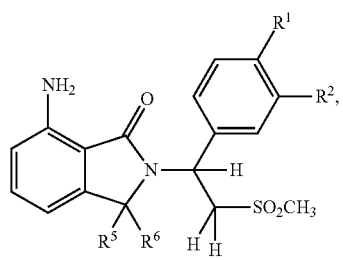

(IX-1)

or a salt or isotopologue thereof; and (d) reacting the enantiomerically enriched or enantiomerically pure compound of Formula (IX-1), or a salt or isotopologue thereof, with an acid chloride RCOCl, or an isotopologue thereof, to form the enantiomerically enriched or enantiomerically pure compound of Formula (I-b-1), or a salt or isotopologue thereof.

In one embodiment, provided herein is a process for the preparation of an enantiomerically enriched or enantiomerically pure compound of Formula (I-b-2):

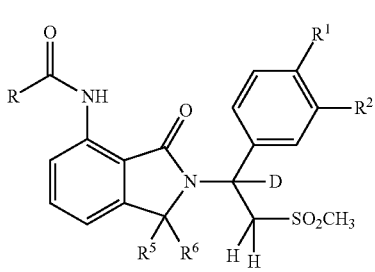

(I-b-2)

or a salt, solvate including a hydrate, stereoisomer, isotopologue, or polymorph thereof, wherein:

$R^1$ is OMe enriched with 0, 1, 2, or 3 deuterium;
$R^2$ is OEt enriched with 0, 1, 2, 3, 4, or 5 deuterium;
$R^5$ and $R^6$ are independently hydrogen or deuterium; and
R is cyclopropyl enriched with 0, 1, 2, 3, 4, or 5 deuterium;

comprising the steps of (a) reducing an enamine of Formula (II-a):

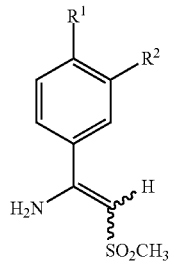

(II-a)

or a salt or isotopologue thereof, via hydrogenation with deuterium gas, in a solvent containing exchangeable proton for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-2):

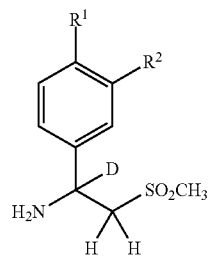

(III-2)

or a salt or isotopologue thereof;

(b) reacting the enantiomerically enriched or enantiomerically pure aminosulfone of Formula (III-2), or a salt or isotopologue thereof, with a compound of Formula (VI-a):

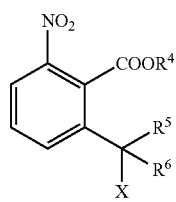

(VI-a)

or a salt or isotopologue thereof, wherein $R^4$ is $(C_1\text{-}C_3)$alkyl, and X is halogen, to form an enantiomerically enriched or enantiomerically pure compound of Formula (VIII-2):

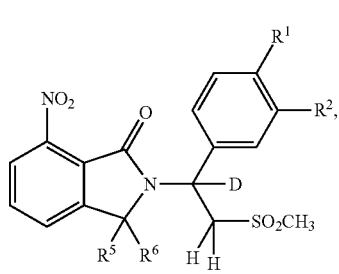

(VIII-2)

or a salt or isotopologue thereof;

(c) reducing the enantiomerically enriched or enantiomerically pure compound of Formula (VIII-2), or a salt or isotopologue thereof, to form an enantiomerically enriched or enantiomerically pure compound of Formula (IX-2):

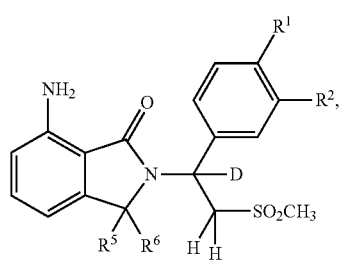

(IX-2)

or a salt or isotopologue thereof; and (d) reacting the enantiomerically enriched or enantiomerically pure compound of Formula (IX-2), or a salt or isotopologue thereof, with an acid chloride RCOCl, or an isotopologue thereof, to form the enantiomerically enriched or enantiomerically pure compound of Formula (I-b-2), or a salt or isotopologue thereof.

In one embodiment, provided herein is a process for the preparation of an enantiomerically enriched or enantiomerically pure compound of Formula (I-b-3):

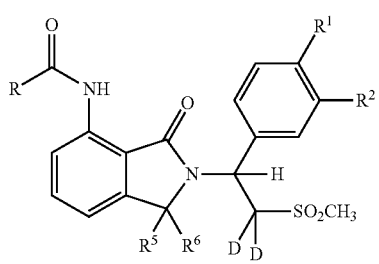

(I-b-3)

or a salt, solvate including a hydrate, stereoisomer, isotopologue, or polymorph thereof, wherein:

$R^1$ is OMe enriched with 0, 1, 2, or 3 deuterium;
$R^2$ is OEt enriched with 0, 1, 2, 3, 4, or 5 deuterium;
$R^5$ and $R^6$ are independently hydrogen or deuterium; and
R is cyclopropyl enriched with 0, 1, 2, 3, 4, or 5 deuterium;
comprising the steps of (a) reducing an enamine of Formula (III-a):

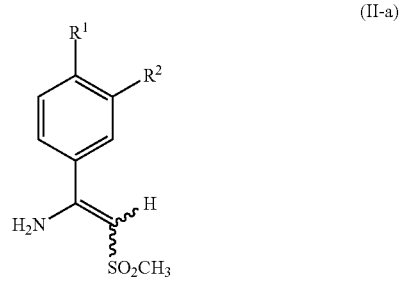

(II-a)

or a salt or isotopologue thereof, via hydrogenation with hydrogen gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-3):

(III-3)

[structure]

or a salt or isotopologue thereof;

(b) reacting the enantiomerically enriched or enantiomerically pure aminosulfone of Formula (III-3), or a salt or isotopologue thereof, with a compound of Formula (VI-a):

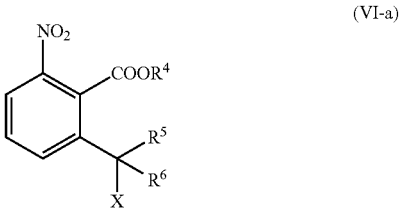

(VI-a)

or a salt or isotopologue thereof, wherein $R^4$ is $(C_1\text{-}C_3)$alkyl, and X is halogen, to form an enantiomerically enriched or enantiomerically pure compound of Formula (VIII-3):

(VIII-3)

[Structure: 7-nitro-isoindolin-1-one with N-substituted CH(Ar)-CD2-SO2CH3 group, Ar = 4-R1, 3-R2 phenyl; R5, R6 on isoindoline C3]

or a salt or isotopologue thereof;

(c) reducing the enantiomerically enriched or enantiomerically pure compound of Formula (VIII-3), or a salt or isotopologue thereof, to form an enantiomerically enriched or enantiomerically pure compound of Formula (IX-3):

(IX-3)

[Structure: 7-amino analog of VIII-3]

or a salt or isotopologue thereof; and (d) reacting the enantiomerically enriched or enantiomerically pure compound of Formula (IX-3), or a salt or isotopologue thereof, with an acid chloride RCOCl, or an isotopologue thereof, to form the enantiomerically enriched or enantiomerically pure compound of Formula (I-b-3), or a salt or isotopologue thereof.

In one embodiment, provided herein is a process for the preparation of an enantiomerically enriched or enantiomerically pure compound of Formula (I-b-4):

(I-b-4)

[Structure: R-C(=O)-NH-isoindolinone with N-CD(Ar)-CD2-SO2CH3; Ar = 4-R1, 3-R2 phenyl; R5, R6 on C3]

or a salt, solvate including a hydrate, stereoisomer, isotopologue, or polymorph thereof, wherein:

$R^1$ is OMe enriched with 0, 1, 2, or 3 deuterium;

$R^2$ is OEt enriched with 0, 1, 2, 3, 4, or 5 deuterium;

$R^5$ and $R^6$ are independently hydrogen or deuterium; and

R is cyclopropyl enriched with 0, 1, 2, 3, 4, or 5 deuterium;

comprising the steps of (a) reducing an enamine of Formula (II-a):

(II-a)

[Structure: Ar-C(NH2)=CH-SO2CH3, Ar = 4-R1, 3-R2 phenyl]

or a salt or isotopologue thereof, via hydrogenation with deuterium gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-4):

(III-4)

[Structure: Ar-CD(NH2)-CD2-SO2CH3]

or a salt or isotopologue thereof;

(b) reacting the enantiomerically enriched or enantiomerically pure aminosulfone of Formula (II-4), or a salt or isotopologue thereof, with a compound of Formula (VI-a):

(VI-a)

[Structure: 2-nitro-6-(CR5R6X)-benzoate COOR4]

or a salt or isotopologue thereof, wherein $R^4$ is $(C_1$-$C_3)$alkyl, and X is halogen, to form an enantiomerically enriched or enantiomerically pure compound of Formula (VIII-4):

(VIII-4)

[Structure: 7-nitro-isoindolin-1-one with N-CD(Ar)-CD2-SO2CH3; R5, R6 on C3]

or a salt or isotopologue thereof;

(c) reducing the enantiomerically enriched or enantiomerically pure compound of Formula (VIII-4), or a salt or isotopologue thereof, to form an enantiomerically enriched or enantiomerically pure compound of Formula (IX-4):

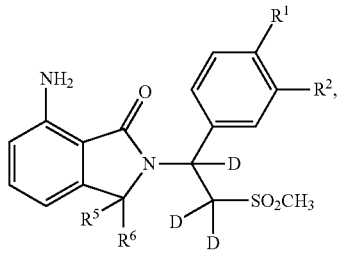

(IX-4)

or a salt or isotopologue thereof; and (d) reacting the enantiomerically enriched or enantiomerically pure compound of Formula (IX-4), or a salt or isotopologue thereof; with an acid chloride RCOCl, or an isotopologue thereof, to form the enantiomerically enriched or enantiomerically pure compound of Formula (I-b-4), or a salt or isotopologue thereof.

In one embodiment, provided herein is a process for the preparation of an enantiomerically enriched or enantiomerically pure compound of Formula (I-b-5):

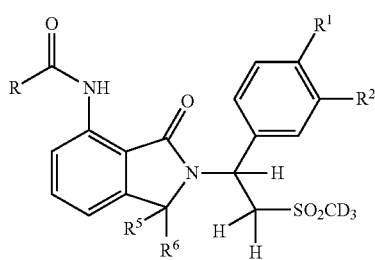

(I-b-5)

or a salt, solvate including a hydrate, stereoisomer, isotopologue, or polymorph thereof, wherein:

R$^1$ is OMe enriched with 0, 1, 2, or 3 deuterium;
R$^2$ is OEt enriched with 0, 1, 2, 3, 4, or 5 deuterium;
R$^5$ and R$^6$ are independently hydrogen or deuterium; and
R is cyclopropyl enriched with 0, 1, 2, 3, 4, or 5 deuterium;
comprising the steps of
(a) reducing an enamine of Formula (II-b):

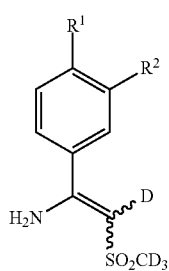

(II-b)

or a salt or isotopologue thereof, via hydrogenation with hydrogen gas, in a solvent containing exchangeable proton for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-5):

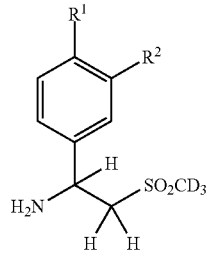

(III-5)

or a salt or isotopologue thereof;

(b) reacting the enantiomerically enriched or enantiomerically pure aminosulfone of Formula (III-5), or a salt or isotopologue thereof, with a compound of Formula (VI-a):

(VI-a)

or a salt or isotopologue thereof, wherein R$^4$ is (C$_1$-C$_3$)alkyl, and X is halogen, to form an enantiomerically enriched or enantiomerically pure compound of Formula (VIII-5):

(VIII-5)

or a salt or isotopologue thereof;

(c) reducing the enantiomerically enriched or enantiomerically pure compound of Formula (VIII-5), or a salt or isotopologue thereof, to form an enantiomerically enriched or enantiomerically pure compound of Formula (IX-5):

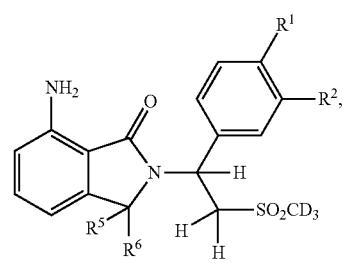

(IX-5)

or a salt or isotopologue thereof; and (d) reacting the enantiomerically enriched or enantiomerically pure compound of Formula (IX-5), or a salt or isotopologue thereof, with an acid chloride RCOCl, or an isotopologue thereof, to form the enantiomerically enriched or enantiomerically pure compound of Formula (I-b-5), or a salt or isotopologue thereof.

In one embodiment, provided herein is a process for the preparation of an enantiomerically enriched or enantiomerically pure compound of Formula (I-b-6):

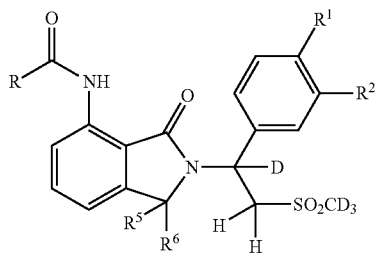
(I-b-6)

or a salt, solvate including a hydrate, stereoisomer, isotopologue, or polymorph thereof wherein:

$R^1$ is OMe enriched with 0, 1, 2, or 3 deuterium;
$R^2$ is OEt enriched with 0, 1, 2, 3, 4, or 5 deuterium;
$R^5$ and $R^6$ are independently hydrogen or deuterium; and
R is cyclopropyl enriched with 0, 1, 2, 3, 4, or 5 deuterium;
comprising the steps of
(a) reducing an enamine of Formula (II-b):

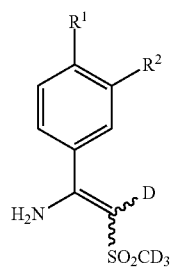
(II-b)

or a salt or isotopologue thereof, via hydrogenation with deuterium gas, in a solvent containing exchangeable proton for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-6):

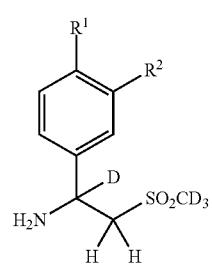
(III-6)

or a salt or isotopologue thereof;

(b) reacting the enantiomerically enriched or enantiomerically pure aminosulfone of Formula (III-6), or a salt or isotopologue thereof, with a compound of Formula (VI-a):

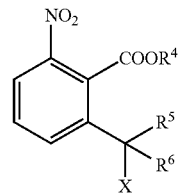
(VI-a)

or a salt or isotopologue thereof, wherein $R^4$ is $(C_1-C_3)$alkyl, and X is halogen, to form an enantiomerically enriched or enantiomerically pure compound of Formula (VIII-6):

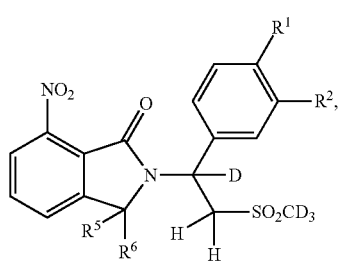
(VIII-6)

or a salt or isotopologue thereof;

(c) reducing the enantiomerically enriched or enantiomerically pure compound of Formula (VIII-6), or a salt or isotopologue thereof, to form an enantiomerically enriched or enantiomerically pure compound of Formula (IX-6):

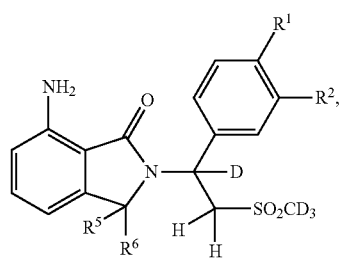
(IX-6)

or a salt or isotopologue thereof; and (d) reacting the enantiomerically enriched or enantiomerically pure compound of Formula (IX-6), or a salt or isotopologue thereof, with an acid chloride RCOCl, or an isotopologue thereof, to form the enantiomerically enriched or enantiomerically pure compound of Formula (I-b-6), or a salt or isotopologue thereof.

In one embodiment, provided herein is a process for the preparation of an enantiomerically enriched or enantiomerically pure compound of Formula (I-b-7):

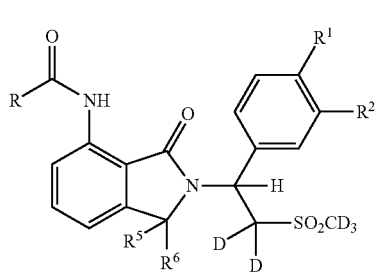
(I-b-7)

or a salt, solvate including a hydrate, stereoisomer, isotopologue, or polymorph thereof, wherein:

$R^1$ is OMe enriched with 0, 1, 2, or 3 deuterium;

$R^2$ is OEt enriched with 0, 1, 2, 3, 4, or 5 deuterium;

$R^5$ and $R^6$ are independently hydrogen or deuterium; and

R is cyclopropyl enriched with 0, 1, 2, 3, 4, or 5 deuterium;

comprising the steps of (a) reducing an enamine of Formula (II-b):

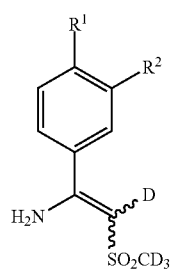

(II-b)

or a salt or isotopologue thereof, via hydrogenation with hydrogen gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III-7):

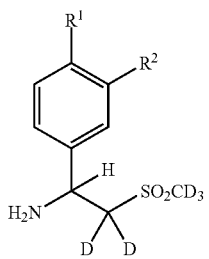

(III-7)

or a salt or isotopologue thereof;

(b) reacting the enantiomerically enriched or enantiomerically pure aminosulfone of Formula (II-7), or a salt or isotopologue thereof, with a compound of Formula (VI-a):

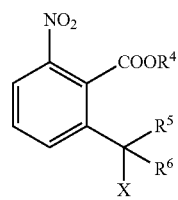

(VI-a)

or a salt or isotopologue thereof, wherein $R^4$ is $(C_1-C_3)$alkyl, and X is halogen, to form an enantiomerically enriched or enantiomerically pure compound of Formula (VIII-7):

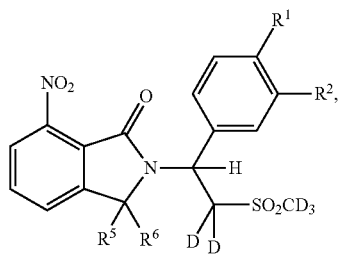

(VIII-7)

or a salt or isotopologue thereof;

(c) reducing the enantiomerically enriched or enantiomerically pure compound of Formula (VIII-7), or a salt or isotopologue thereof, to form an enantiomerically enriched or enantiomerically pure compound of Formula (IX-7):

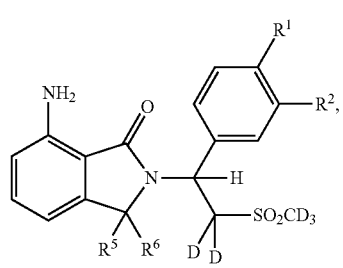

(IX-7)

or a salt or isotopologue thereof; and (d) reacting the enantiomerically enriched or enantiomerically pure compound of Formula (IX-7), or a salt or isotopologue thereof, with an acid chloride RCOCl, or an isotopologue thereof, to form the enantiomerically enriched or enantiomerically pure compound of Formula (I-b-7), or a salt or isotopologue thereof.

In one embodiment, provided herein is a process for the preparation of an enantiomerically enriched or enantiomerically pure compound of Formula (I-b-8):

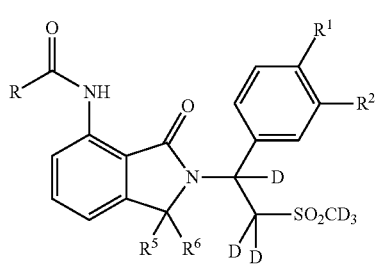

(I-b-8)

or a salt, solvate including a hydrate, stereoisomer, isotopologue, or polymorph thereof, wherein:

$R^1$ is OMe enriched with 0, 1, 2, or 3 deuterium;

$R^2$ is OEt enriched with 0, 1, 2, 3, 4, or 5 deuterium;

$R^5$ and $R^6$ are independently hydrogen or deuterium; and

R is cyclopropyl enriched with 0, 1, 2, 3, 4, or 5 deuterium;

comprising the steps of (a) reducing an enamine of Formula (II-b):

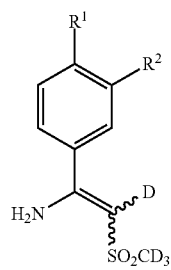

(II-b)

or a salt or isotopologue thereof, via hydrogenation with deuterium gas, in a solvent not containing exchangeable proton (including a solvent containing exchangeable deuterium for proton-deuterium exchange, such as $d_1$-TFE), and in the presence of (1) a metal catalyst and a chiral ligand or (2) a chiral metal catalyst/ligand complex to form an enantiomerically enriched or enantiomerically pure aminosulfone of Formula (III-8):

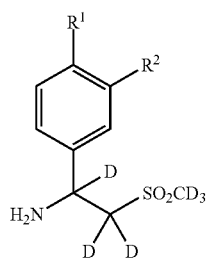

(III-8)

or a salt or isotopologue thereof;

(b) reacting the enantiomerically enriched or enantiomerically pure aminosulfone of Formula (II-8), or a salt or isotopologue thereof, with a compound of Formula (VI-a):

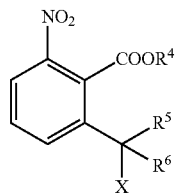

(VI-a)

or a salt or isotopologue thereof, wherein $R^4$ is $(C_1\text{-}C_3)$alkyl, and X is halogen, to form an enantiomerically enriched or enantiomerically pure compound of Formula (VIII-8):

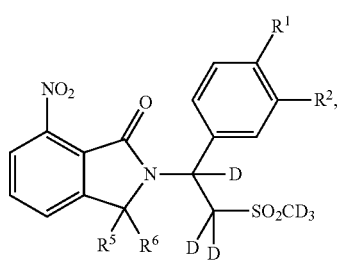

(VIII-8)

or a salt or isotopologue thereof;

(c) reducing the enantiomerically enriched or enantiomerically pure compound of Formula (VIII-8), or a salt or isotopologue thereof, to form an enantiomerically enriched or enantiomerically pure compound of Formula (IX-8):

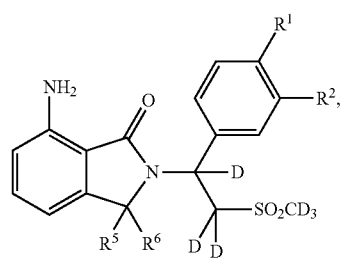

(IX-8)

or a salt or isotopologue thereof; and (d) reacting the enantiomerically enriched or enantiomerically pure compound of Formula (IX-8), or a salt or isotopologue thereof, with an acid chloride RCOCl, or an isotopologue thereof, to form the enantiomerically enriched or enantiomerically pure compound of Formula (I-b-8), or a salt or isotopologue thereof.

With regard to the processes provided herein for the preparation of a compound of Formula (I-b-1), (I-b-2), (I-b-3), (I-b-4), (I-b-5), (I-b-6), (I-b-7), or (I-b-8), in one embodiment, $R^5$ and $R^6$ are both hydrogen. In another embodiment, $R^5$ and $R^6$ are both deuterium. In yet another embodiment, $R^5$ is hydrogen and $R^6$ is deuterium.

In one embodiment, an enantiomerically enriched or enantiomerically pure compound of Formula (I-b), or an isotopologue thereof, is a compound B:

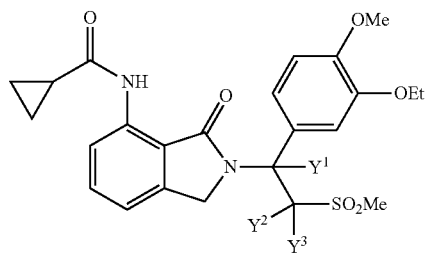

B or an isotopologue thereof.

4.2.3 Other Isotopologues

Although most embodiments and examples provided herein are directed to processes for the preparation of compounds enriched with one or more deuterium in the

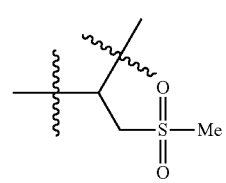 [SMILES: *C(*)CS(C)(=O)=O]

moiety of a compound provided herein, it is to be understood that the corresponding compounds enriched with isotopes of carbon (e.g., $^{13}C$) and nitrogen (e.g., $^{15}N$) or enriched with deuterium at other moieties of a compound provided herein can be synthesized by the processes provided herein when the corresponding isotopically enriched starting materials are used. For example, certain isotopically enriched intermediates have been reported in International Application Publication No. WO2012/097116.

In one embodiment, the processes provided herein are applied to the following isopotologues of a compound of Formula (V):

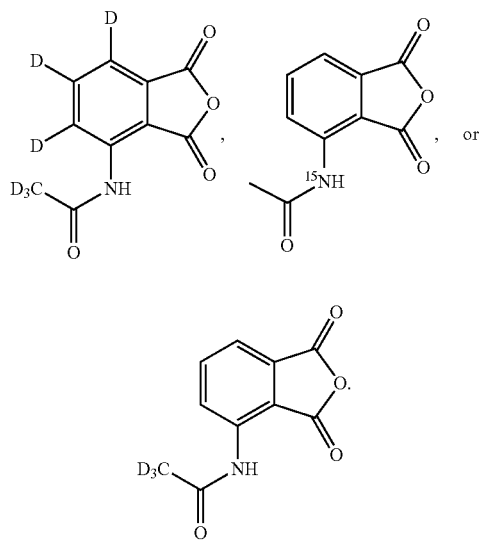

In one embodiment, the processes provided herein are applied to the following isopotologues of a compound of Formula (III):

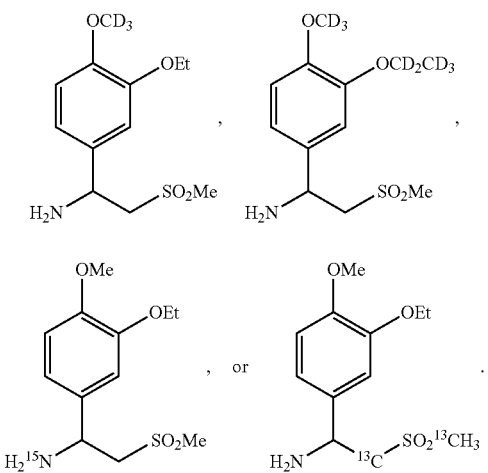

A compound of Formula (I) prepared by the processes provided herein may be subjected to further modifications known in the art to provide isotopologues of a compound of Formula (I). In one embodiment, as illustrated below, a compound of Formula (I) is subsequently subjected to aromatic deuteration conditions to afford an aromatically deuterated compound of Formula (I).

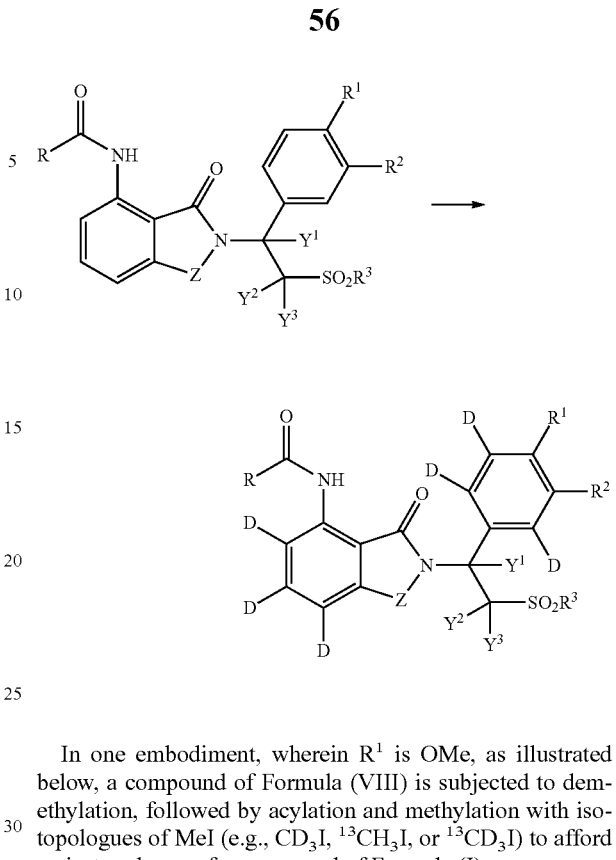

In one embodiment, wherein R¹ is OMe, as illustrated below, a compound of Formula (VIII) is subjected to demethylation, followed by acylation and methylation with isotopologues of MeI (e.g., CD₃I, ¹³CH₃I, or ¹³CD₃I) to afford an isotopologue of a compound of Formula (I).

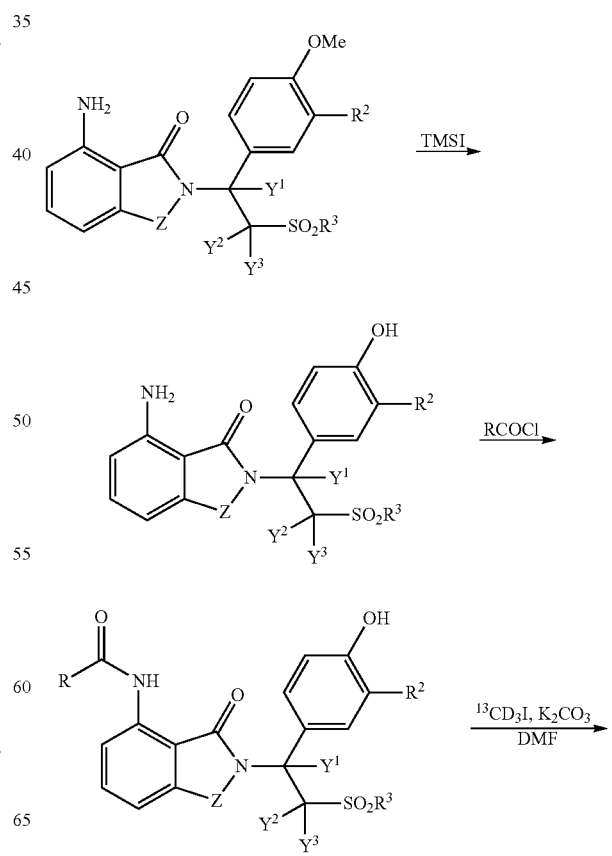

-continued

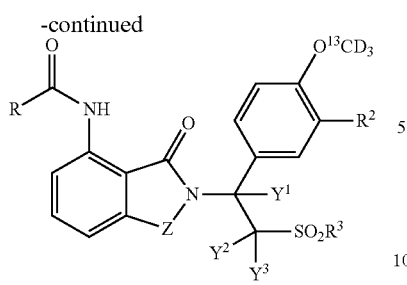

In one embodiment, wherein $R^1$ is $OCD_3$, as illustrated below, a 4-(methoxy-$d_3$)-benzaldehyde is prepared by contacting a 4-OH-benzaldehyde with $D_3COSO_2OCD_3$ in the presence of a base (e.g., $Cs_2CO_3$) and in a solvent. In one embodiment, the solvent is acetone. In another embodiment, the solvent is a mixture of acetone and water. In one embodiment, the solvent is 95:5 acetone/water. In one embodiment, the presence of water in the solvent suppresses formation of impurities resulted from aldo condensation. In one embodiment, the amount of $Cs_2CO_3$ is between about 1 equiv. to about 3 equiv. to the 4-OH-benzaldehyde. In one embodiment, the amount of $Cs_2CO_3$ is 1 equiv. to the 4-OH-benzaldehyde.

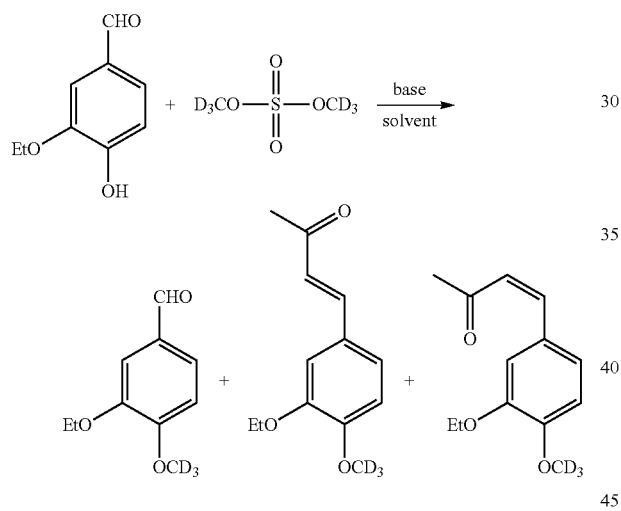

4.2.4 Preparation of Aminosulfone Compounds

In one embodiment, provided herein is a process for the preparation of an enantiomerically enriched or enantiomerically pure aminosulfone compound of Formula (III):

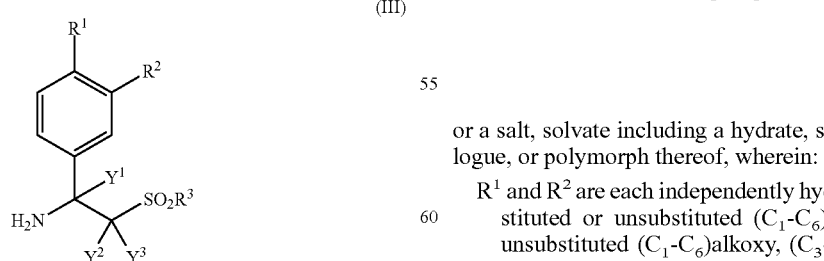

or a salt, solvate including a hydrate, stereoisomer, isotopologue, or polymorph thereof, wherein:

$R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;

$R^3$ is $(C_1-C_6)$alkyl, or an isotopologue thereof; and $Y^1, Y^2,$ and $Y^3$ are independently hydrogen or deuterium;

comprising the step of (a) reducing an enamine of Formula (II):

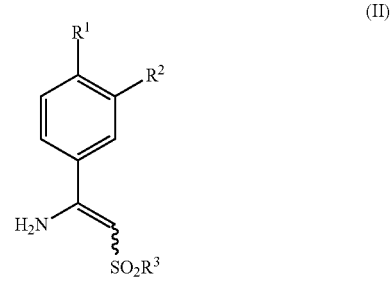

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III), or a salt or isotopologue thereof.

In one embodiment, provided herein is a process for the preparation of an enantiomerically enriched or enantiomerically pure aminosulfone compound of Formula (III):

(III)

or a salt, solvate including a hydrate, stereoisomer, isotopologue, or polymorph thereof, wherein:

$R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;

$R^3$ is $(C_1-C_6)$alkyl, or an isotopologue thereof; and $Y^1, Y^2,$ and $Y^3$ are independently hydrogen or deuterium;

wherein not all of $Y^1, Y^2,$ and $Y^3$ are hydrogen;

comprising the step of
(a) reducing an enamine of Formula (II):

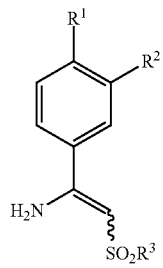

(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III), or a salt or isotopologue thereof, wherein deuterium gas or a solvent containing exchangeable deuterium for proton-deuterium exchange or both is used.

In one embodiment, provided herein is a process for the preparation of an enantiomerically enriched or enantiomerically pure aminosulfone compound of Formula (III):

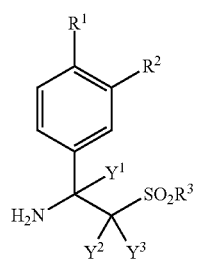

(III)

or a salt, solvate including a hydrate, stereoisomer, isotopologue, or polymorph thereof, wherein:
$R^1$ and $R^2$ are each independently hydrogen, halogen, substituted or unsubstituted $(C_1$-$C_6)$alkyl, substituted or unsubstituted $(C_1$-$C_6)$alkoxy, $(C_3$-$C_{18})$cycloalkyl, $(C_3$-$C_6)$cycloalkoxy, cyano, —$CF_3$, $(C_3$-$C_{18})$cycloalkyl-$(C_1$-$C_6)$alkoxy, or an isotopologue thereof;
$R^3$ is $(C_1$-$C_6)$alkyl, or an isotopologue thereof;
$Y^1$ is hydrogen or deuterium; and
$Y^2$ and $Y^3$ are both deuterium;
comprising the step of
(a) reducing an enamine of Formula (II):

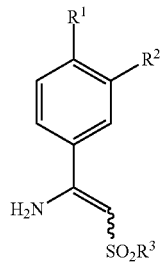

(II)

or a salt or isotopologue thereof, via hydrogenation with hydrogen gas or deuterium gas, in a solvent containing exchangeable deuterium for proton-deuterium exchange, and in the presence of (1) a metal catalyst and a chiral ligand or (2) a chiral metal catalyst/ligand complex to form an enantiomerically enriched or enantiomerically pure aminosulfone of Formula (III), or a salt or isotopologue thereof.

Step (a) is as described herein and elsewhere above.

5. EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); M (molar); mM (millimolar); μM (micromolar); eq. (equivalent); mmol (millimoles); Hz (Hertz); MHz (megahertz); hr or hrs (hour or hours); min (minutes); and MS (mass spectrometry).

For all of the following examples, unless otherwise specified, standard work-up and purification methods known to those skilled in the art can be utilized. Unless otherwise specified, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

Isotopically enriched analogs of the compounds provided herein may generally be prepared according synthetic routes known in the art, wherein one or more of the reagents, starting materials, precursors, or intermediates used is replaced by one or more isotopically enriched reagents, starting materials, precursors, or intermediates. Isotopically enriched reagents, starting materials, precursors, or intermediates are commercially available or may be prepared by routine procedures known to one of skill in the art. For example, the preparation of certain isotopically enriched intermediates have been reported in International Application Publication No. WO2012/097116.

Example 1

1-(3-ethoxy-4-methoxyphenyl)-2-(methylsulfonyl) ethenamine (H—CH3-Compound C)

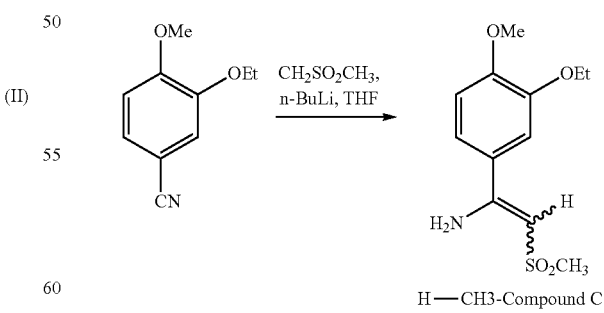

A slurry of dimethylsulfone (85 g, 903 mmol) in THF (480 ml) was treated with a 1.6M solution of n-butyllithium in hexane (505 ml, 808 mmol) at 0-5° C. The resulting mixture was agitated for 1 hour then a solution of 3-ethoxy-4-methoxybenzonitrile (80 g, 451 mmol) in THF (240 ml) was added at 0-5° C. The mixture was agitated at 0-5° C. for 0.5 hour, warmed to 25-30° C. over 0.5 hour and then agitated for 1 hour. Water (1.4 L) was added at 25-30° C. and the reaction mass was agitated overnight at room temperature (20-30° C.). The solid was filtered and subsequently washed with a 2:1 mixture of water:THF (200 ml), water (200 ml) and heptane (2×200 ml). The solid was dried under reduced pressure at 40-45° C. to provide the product as a white solid (102 g, 83% yield); $^1$H NMR (DMSO-d) δ 1.34 (t, J=7.0 Hz, 3H), 2.99 (s, 3H), 3.80 (s, 3H), 4.08 (q, J=7.0 Hz, 2H), 5.03 (s, 1H), 6.82 (s, 2H), 7.01 (d, J=8.5 Hz, 1H), 7.09-7.22 (m, 2H).

Example 2

S)-1-(3-ethoxy-4-methoxyphenyl)-2-(methylsulfonyl)ethanamine (H—CH2-CH3-Compound D

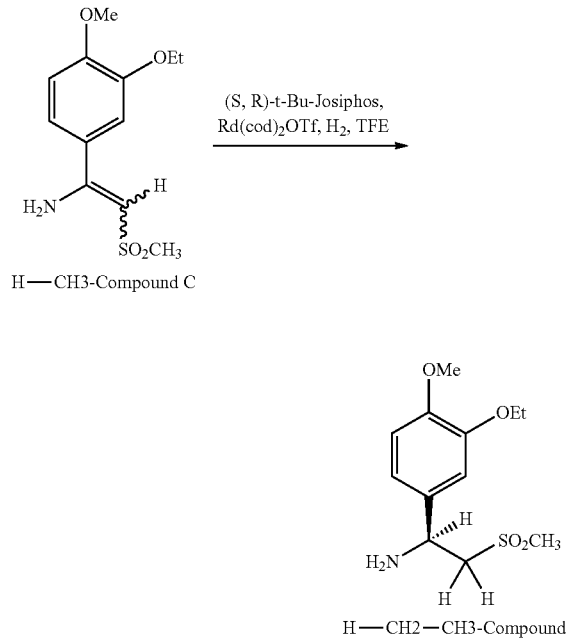

H—CH3-Compound C

H—CH2—CH3-Compound D

A solution of bis(1,5-cyclooctadiene)rhodium(I) trifluoromethanesulfonate (36 mg, 0.074 mmol) and (S)-1-[(R)-2-(diphenylphosphino)ferrocenyl]ethyldi-tert-butylphosphine (40 mg, 0.074 mmol) in 25 mL of 2,2,2-trifluoroethanol was prepared under nitrogen. To this solution was then charged 1-(3-ethoxy-4-methoxyphenyl)-2-(methylsulfonyl)ethenamine (2.0 g, 7.4 mmol). The resulting mixture was heated to 50° C. and hydrogenated under 90 psig hydrogen pressure. After 18 h, the mixture was cooled to ambient temperature and removed from the hydrogenator. The mixture was evaporated and the residue was purified by chromatography on a C18 reverse phase column using a water-acetonitrile gradient. The appropriate fractions were pooled and evaporated to ~150 mL. To this solution was added brine (20 mL), and the resulting solution was extracted with EtOAc (3×50 mL). The combined organic layers were dried (MgSO$_4$) and evaporated to provide the product as a white crystalline solid (1.4 g, 70% yield); achiral HPLC (Hypersil BDS C$_8$, 5.0 μm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 9.11 (99.6%); chiral HPLC (Chiralpak AD-H 5.0 μm Daicel, 250×4.6 mm, 1.0 mL/min, 280 nm, 70:30:0.1 heptane-i-PrOH-diethylamine): 7.32 (97.5%), 8.26 (2.47%); $^1$H NMR (DMSO-d$_6$) δ 1.32 (t, J=7.0 Hz, 3H), 2.08 (s, 2H), 2.96 (s, 3H), 3.23 (dd, J=3.6, 14.4 Hz, 1H), 3.41 (dd, J=9.4, 14.4 Hz, 1H), 3.73 (s, 3H), 4.02 (q, J=7.0 Hz, 2H), 4.26 (dd, J=3.7, 9.3 Hz, 1H), 6.89 (s, 2H), 7.02 (s, 1H); $^{13}$C NMR (DMSO-d$_6$) δ 14.77, 41.98, 50.89, 55.54, 62.03, 63.68, 111.48, 111.77, 118.36, 137.30, 147.93, 148.09.

Example 3

S)—N-(2-(1-(3-ethoxy-4-methoxyphenyl)-2-(methylsulfonyl)ethyl)-1,3-dioxoisoindolin-4-yl)acetamide (H—CH2-CH3-Compound A

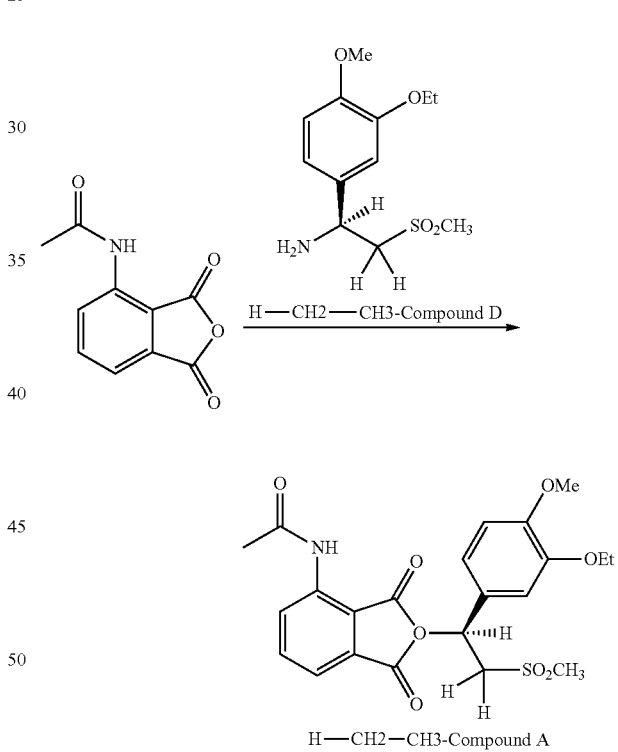

H—CH2—CH3-Compound D

H—CH2—CH3-Compound A

N-(1,3-dioxo-1,3-dihydroisobenzofuran-4-yl)acetamide, which may be obtained via techniques known in the art, (S)-1-(3-ethoxy-4-methoxyphenyl)-2-(methylsulfonyl)ethanamine, and glacial acetic acid is refluxed overnight and then cooled to <50° C. The solvent is then removed in vacuo, and the residue is dissolved in ethyl acetate. The resulting solution is washed with water, saturated aqueous NaHCO$_3$, brine, and dried over sodium sulphate. The solvent is evaporated in vacuo, and the residue is recrystallized from a binary solvent containing ethanol and acetone. The solid is isolated by vacuum filtration and washed with ethanol. The product is then dried to afford H—CH2-CH3-Compound A.

Example 4

S)—N-(2-(1-(3-ethoxy-4-methoxlyphenyl)-2-(methylsulfonyl)ethyl)-1,3-dioxoisoindolin-4-yl)acetamide (H—CH2-CH3-Compound B

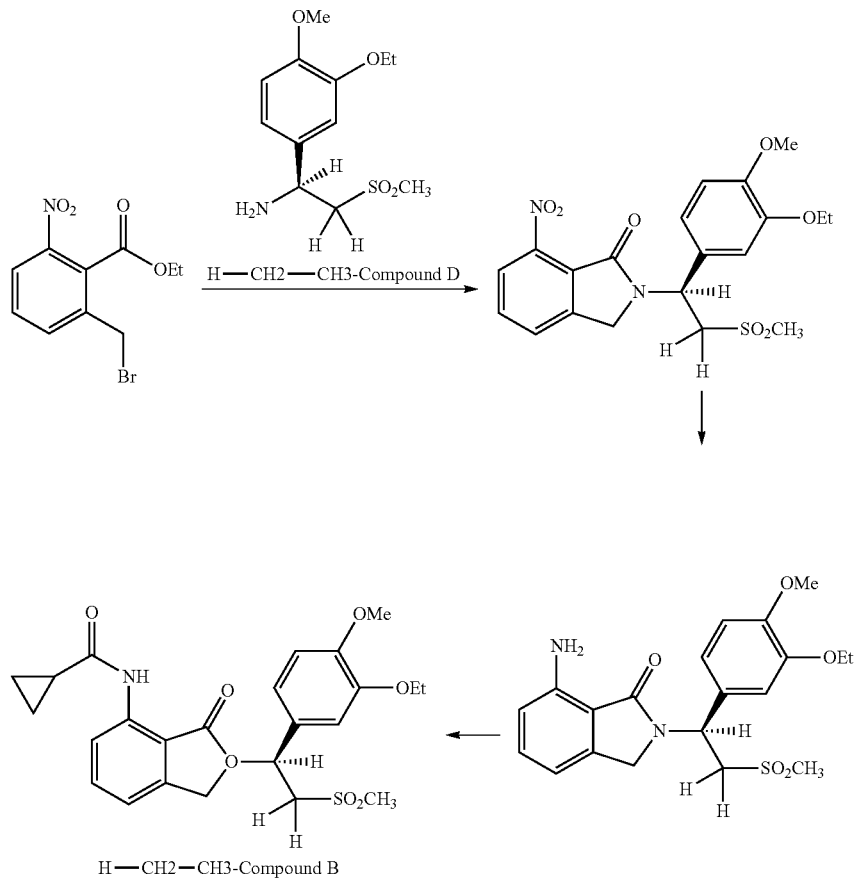

A mixture of ethyl 2-(bromomethyl)-6-nitrobenzoate and H—CH2-CH3-Compound D, triethyl amine in DMF is heated to reflux. The solvent is removed in vacuo. The crude mixture is purified by column chromatography to give (S)-2-(1-(3-ethoxy-4-methoxyphenyl)-2-(methylsulfonyl)ethyl)-7-nitroisoindolin-1-one. A mixture of (S)-2-(1-(3-ethoxy-4-methoxyphenyl)-2-(methylsulfonyl)ethyl)-7-nitroisoindolin-1-one and Pd/C in ethyl acetate is shaken under hydrogen. The suspension is filtered thru a pad of Celite. The solvent is removed in vacuo. The crude mixture is purified by column chromatography to give (S)-7-amino-2-(1-(3-ethoxy-4-methoxyphenyl)-2-(methylsulfonyl)ethyl)isoindolin-1-one.

(S)—N-(2-(1-(3-ethoxy-4-methoxyphenyl)-2-(methylsulfonyl)ethyl)-3-oxoisoindolin-4-yl)cyclopropanecarboxamide is synthesized based upon the procedures described, for example, in Example 7 of U.S. Pat. No. 6,667,316, starting from (S)-7-amino-2-(1-(3-ethoxy-4-methoxyphenyl)-2-(methylsulfonyl)ethyl)isoindolin-1-one. The product is further purified by column chromatography or crystallization.

Example 5

D-CH2-CH3-Compound D

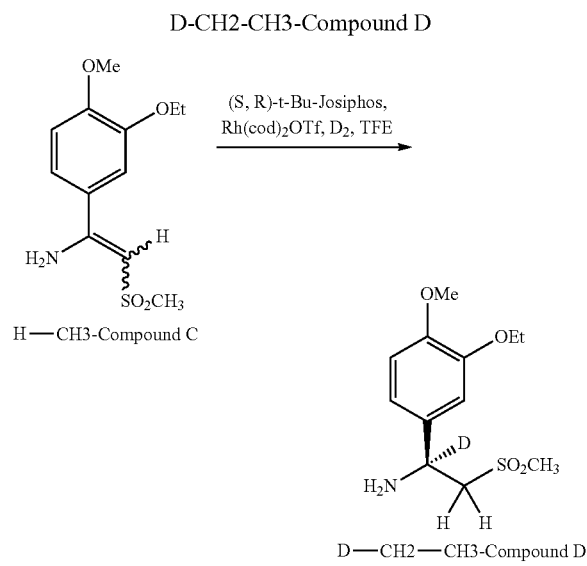

D-CH2-CH3-Compound D is prepared based on the routes described in Example 2, but using deuterium gas in place of hydrogen gas.

Example 6

D-CH2-CH3-Compound A

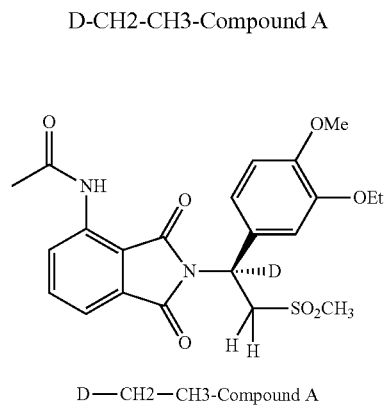

D—CH2—CH3-Compound A

D-CH2-CH3-Compound A is prepared based on the routes described in Example 3, but using D-CH2-CH3-Compound D in place of H—CH2-CH3-Compound D.

Example 7

D-CH2-CH3-Compound B

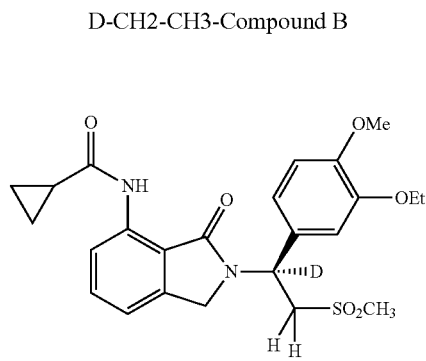

D—CH2—CH3-Compound B

D-CH2-CH3-Compound B is prepared based on the routes described in Example 4, but using D-CH2-CH3-Compound D in place of H—CH2-CH3-Compound D.

Example 8

H-CD2-CH3-Compound D

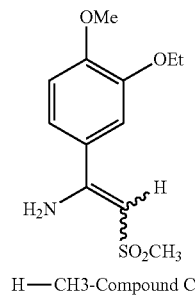

H—CH3-Compound C

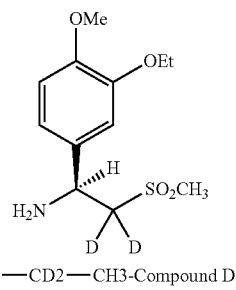

H—CD2—CH3-Compound D

H-CD2-CH3-Compound D is prepared based on the routes described in Example 2, but using d¹-TFE in place of TFE as solvent.

Example 9

H-CD2-CH3-Compound A

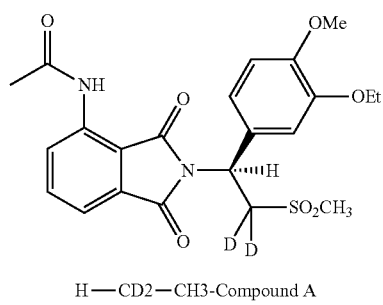

H—CD2—CH3-Compound A

H-CD2-CH3-Compound A is prepared based on the routes described in Example 3, but using H-CD2-CH3-Compound D in place of H—CH2-CH3-Compound D.

Example 10

H-CD2-CH3-Compound B

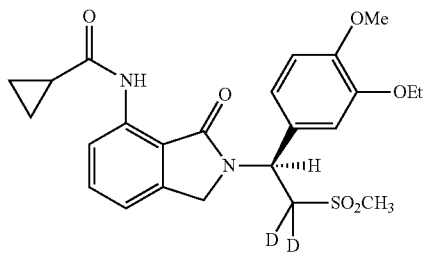

H—CD2—CH3-Compound B

H-CD2-CH3-Compound B is prepared based on the routes described in Example 4, but using H-CD2-CH3-Compound D in place of H—CH2-CH3-Compound D.

Example 11

D-CD2-CH3-Compound D

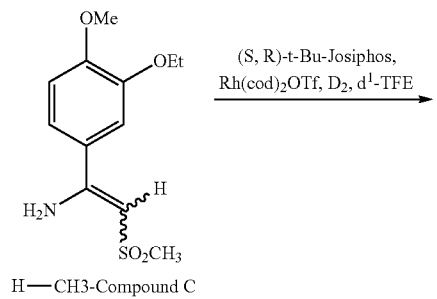

H—CH3-Compound C (S, R)-t-Bu-Josiphos, Rh(cod)$_2$OTf, D$_2$, d$^1$-TFE →

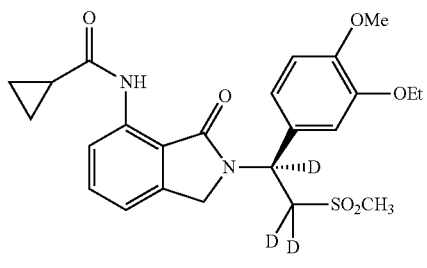

D—CD2—CH3-Compound D

D-CD2-CH3-Compound D is prepared based on the routes described in Example 2, but using deuterium gas in place of hydrogen gas and using d$^1$-TFE in place of TFE as solvent.

Example 12

D-CD2-CH3-Compound A

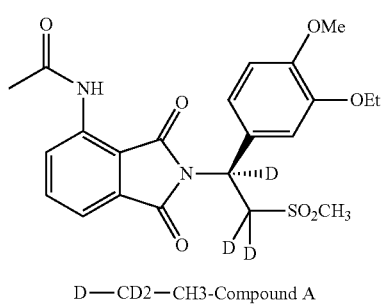

D—CD2—CH3-Compound A

D-CD2-CH3-Compound A is prepared based on the routes described in Example 3, but using D-CD2-CH3-Compound D in place of H—CH2-CH3-Compound D.

Example 13

D-CD2-CH3-Compound B

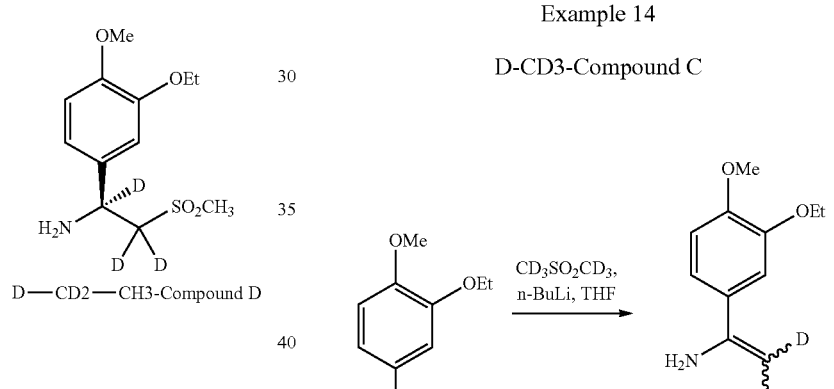

D—CD2—CH3-Compound B

D-CD2-CH3-Compound B is prepared based on the routes described in Example 4, but using D-CD2-CH3-Compound D in place of H—CH2-CH3-Compound D.

Example 14

D-CD3-Compound C

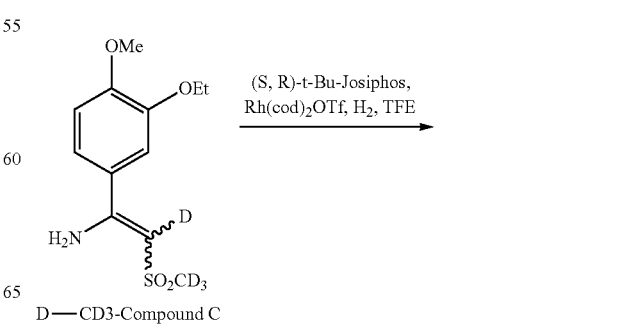

D—CD3-Compound C

D-CD3-Compound C is prepared based on the routes described in Example 1, but using CD$_3$SO$_2$CD$_3$ in place of CH$_3$SO$_2$CH$_3$.

Example 15

H—CH2-CD3-Compound D

D—CD3-Compound C (S, R)-t-Bu-Josiphos, Rh(cod)$_2$OTf, H$_2$, TFE →

-continued

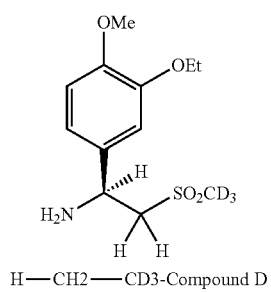

H—CH2—CD3-Compound D

H—CH2-CD3-Compound D is prepared based on the routes described in Example 2, but using D-CD3-Compound C in place of H—CH3-Compound C.

Example 16

H—CH2-CD3-Compound A

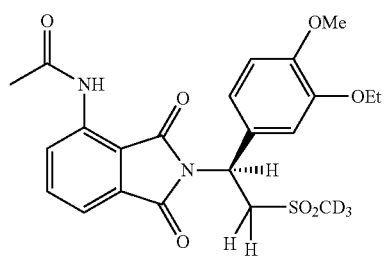

H—CH2—CD3-Compound A

H—CH2-CD3-Compound A is prepared based on the routes described in Example 3, but using H—CH2-CD3-Compound D in place of H—CH2-CH3-Compound D.

Example 17

H—CH2-CD3-Compound B

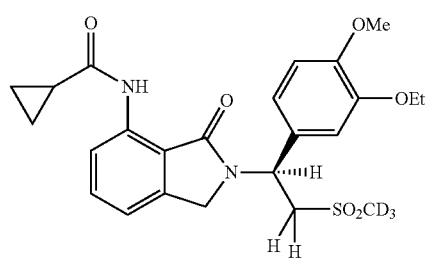

H—CH2—CD3-Compound B

H—CH2-CD3-Compound B is prepared based on the routes described in Example 4, but using H—CH2-CD3-Compound D in place of H—CH2-CH3-Compound D.

Example 18

D-CH2-CD3-Compound D

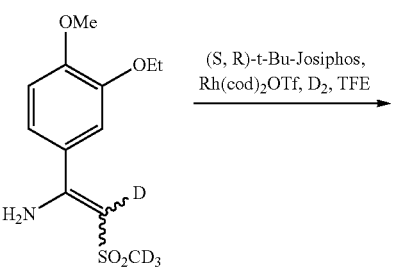

D—CD3-Compound C

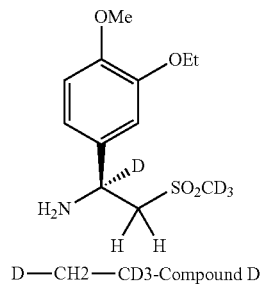

D—CH2—CD3-Compound D

D-CH2-CD3-Compound D is prepared based on the routes described in Example 2, but using D-CD3-Compound C in place of H—CH3-Compound C and using deuterium gas in place of hydrogen gas.

Example 19

D-CH2-CD3-Compound A

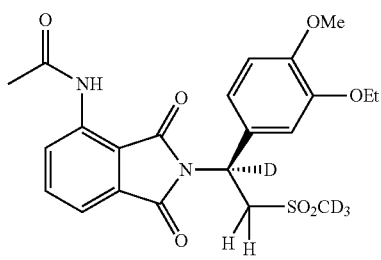

D—CH2—CD3-Compound A

D-CH2-CD3-Compound A is prepared based on the routes described in Example 3, but using D-CH2-CD3-Compound D in place of H—CH2-CH3-Compound D.

Example 20

D-CH2-CD3-Compound B

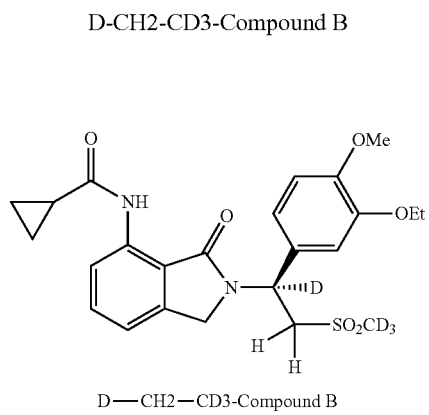

D—CH2—CD3-Compound B

D-CH2-CD3-Compound B is prepared based on the routes described in Example 4, but using D-CH2-CD3-Compound D in place of H—CH2-CH3-Compound D.

Example 21

H-CD2-CD3-Compound D

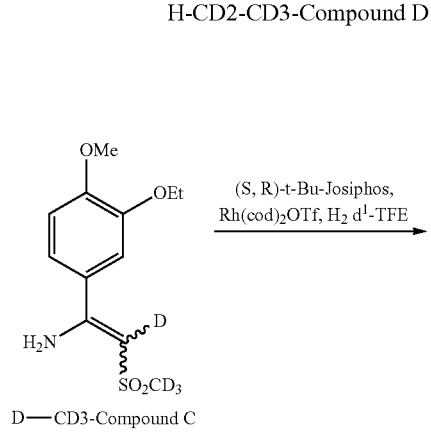

H—CD2—CD3-Compound D

H-CD2-CD3-Compound D is prepared based on the routes described in Example 2, but using D-CD3-Compound C in place of H—CH3-Compound C and using $d^1$-TFE in place of TFE as solvent.

Example 22

H-CD2-CD3-Compound A

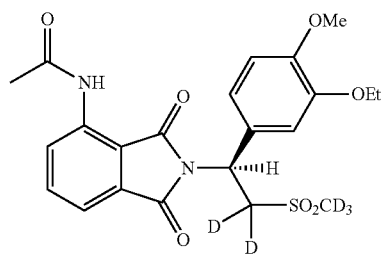

H—CD2—CD3-Compound A

H-CD2-CD3-Compound A is prepared based on the routes described in Example 3, but using H-CD2-CD3-Compound D in place of H—CH2-CH3-Compound D.

Example 23

H-CD2-CD3-Compound B

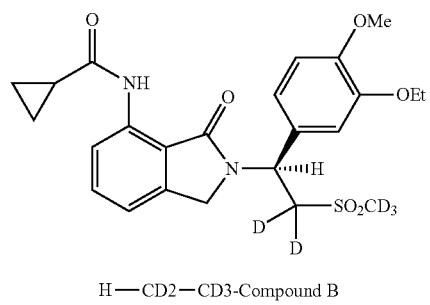

H—CD2—CD3-Compound B

H-CD2-CD3-Compound B is prepared based on the routes described in Example 4, but using H-CD2-CD3-Compound D in place of H—CH2-CH3-Compound D.

Example 24

D-CD2-CD3-Compound D

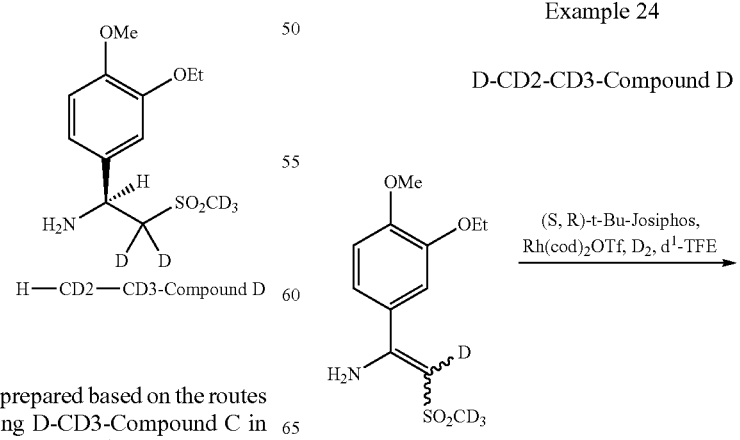

D—CD3-Compound C

73

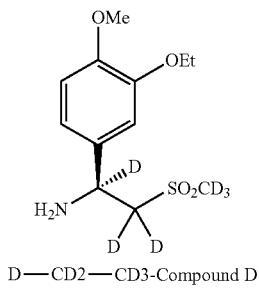

D—CD2—CD3-Compound D

D-CD2-CD3-Compound D is prepared based on the routes described in Example 2, but using D-CD3-Compound C in place of H—CH3-Compound C, using deuterium gas in place of hydrogen gas, and using $d^1$-TFE in place of TFE as solvent.

Example 25

D-CD2-CD3-Compound A

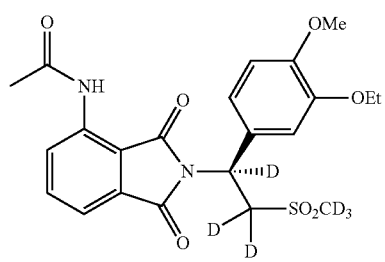

D—CD2—CD3-Compound A

D-CD2-CD3-Compound A is prepared based on the routes described in Example 3, but using D-CD2-CD3-Compound D in place of H—CH2-CH3-Compound D.

Example 26

D-CD2-CD3-Compound B

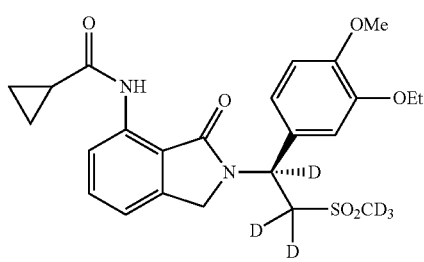

D—CD2—CD3-Compound B

D-CD2-CD3-Compound B is prepared based on the routes described in Example 4, but using D-CD2-CD3-Compound D in place of H—CH2-CH3-Compound D.

74

Example 27

Preparation of 3-ethoxy-4-($d_3$-methoxy)-benzaldehyde

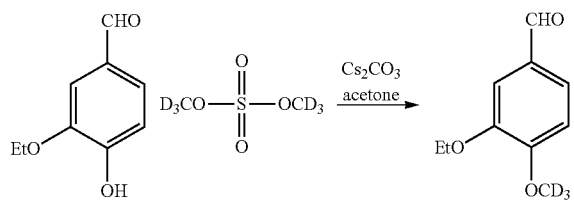

Two batches of 3-ethoxy-4-(methoxy-$d_3$)-benzaldehyde were synthesized using the conditions shown below. The first batch was 10 g scale (based on $(CD_3)_2SO_4$) and provided 13.9 g of product, area % 99.7%; and the second batch was 20 g scale and provided 28 g of product, area % 99.9%. The yields for both batches were quantitative.

A mixture of 3-ethoxy-4-hydroxybenzaldehyde (12.6 g, 76 mmol) and $Cs_2CO_3$ (24.7 g, 75.9 mmol) in acetone was cooled in ice-water bath. $(CD_3)_2SO_4$ (10.0 g, 75.9 mmol) was added and the reaction was allowed to warm slowly to room temperature and was stirred overnight. The reaction mixture was filtered through a pad of celite, the filtrate was concentrated to dryness to give a colorless liquid. The liquid was cooled to room temperature, forming a blue solid. The solid was dried under vacuum at 40° C. providing 13.9 g of the product, in 100% yield; $^1$H NMR ($d_6$-DMSO) δ 1.35 (t, J=7.0 Hz, 3H), 4.09 (q, J=6.9 Hz, 2H), 7.17 (d, J=8.3 Hz, 1H), 7.37 (d, J=1.7 Hz, 1H), 7.55 (dd, J=1.9, 8.1 Hz, 1H), 9.83 (s, 1H).

Example 28

Preparation of 3-ethoxy-4-($d_3$-methoxy)-benzonitrile

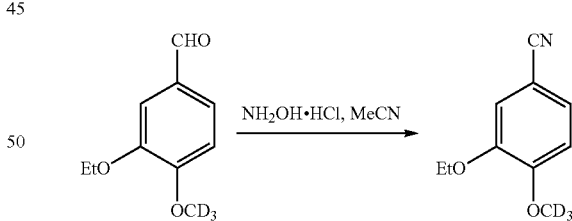

A mixture of hydroxylamine hydrochloride (12.3 g, 177 mmol) in acetonitrile (15 mL) was heated to 70° C. A solution of ethoxy-4-($d_3$-methoxy)benzaldehyde (27.0 g, 147 mmol) in acetonitrile (40 mL) was charged to the mixture and the batch was stirred at 70° C. for 4 hours. The batch was heated to 85° C. for 1 hour and cooled to 20° C. The reaction mixture was evaporated to dryness and dissolved in ethyl acetate (250 mL). The organic layer was washed with water (3×50 mL), brine (30 mL), dried with magnesium sulfate and filtered. The filtrate was evaporated to dryness and the residue was chromatographed (silica gel), eluting with hexane-ethyl acetate 5:1 providing 24.5 g of the product, in 92% yield; $^1$H NMR (d$_6$-DMSO) δ 1.33 (t, J=7.0 Hz, 3H), 4.06 (q, J=7.0 Hz, 2H), 7.11 (d, J=8.3 Hz, 1H), 7.30-7.49 (m, 2H).

Example 29

Preparation of d$_3$-enamine

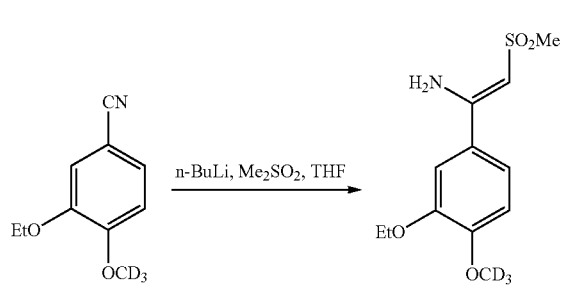

A mixture of dimethylsulfone (5.22 g, 55.5 mmol) in THF (31 mL) was cooled to 0-5° C., and n-butyllithium (31.0 ml, 49.7 mmol) was added at 0-5° C. After the addition was complete, the mixture was stirred at 0-5° C. for 1 hour and a solution of 3-ethoxy-4-methoxybenzonitrile-d$_3$ (5.00 g 27.7 mmol) in THF (15 mL) was added, and the mixture was warmed to room temperature. Water (85 mL) was charged at 20-30° C. and the batch was stirred at 20° C. overnight. The precipitated solid was filtered, washed with 2:1 water:THF (12.5 mL), water (12.5 mL, 2.5×) and heptane (2×12.5 mL). The product was dried under vacuum at 40° C. providing 6.6 g of product, in 87% yield; $^1$H NMR (d$_6$-DMSO) δ 1.34 (t, J=7.0 Hz, 3H), 2.99 (s, 3H), 4.08 (q, J=6.9 Hz, 2H), 5.02 (s, 1H), 6.81 (br, 2H), 7.00 (d, J=8.5 Hz, 1H), 7.12 (d, J=2.1 Hz, 1H), 7.14-7.22 (m, 1H).

Example 30

Preparation of d$_7$-enamine

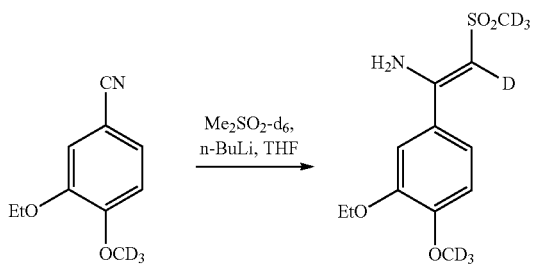

A mixture of d$_6$-dimethylsulfone (5.56 g, 55.5 mmol) and THF (30 mL) was cooled to 0-5° C., and n-butyllithium (31.0 mL, 49.7 mmol) was added at 0-5° C. After addition was complete, the mixture was stirred at 0-5° C. for 1 hour and a solution of d$_3$-[3-ethoxy-4-methoxybenzonitrile] (5.00 g 27.7 mmol) in THF (15 mL) was added and the mixture was warmed up to room temperature. Water (85 mL) was charged at 20-30° C. and the batch was stirred at 20° C. overnight. The precipitated solid was filtered, washed with 2:1 water:THF (12.5 mL), water (12.5 mL, 2.5×) and heptane (2×12.5 mL). The product was dried under vacuum at 40° C. providing 6.5 g of the product, in 84% yield; $^1$H NMR (d$_6$-DMSO) δ 1.26-1.44 (m, 3H), 4.08 (q, J=7.0 Hz, 2H), 6.95-7.07 (m, 1H), 7.09-7.27 (m, 2H).

Example 31

Preparation of d$_3$-aminosulfone N-acetyl-L-leucine salt

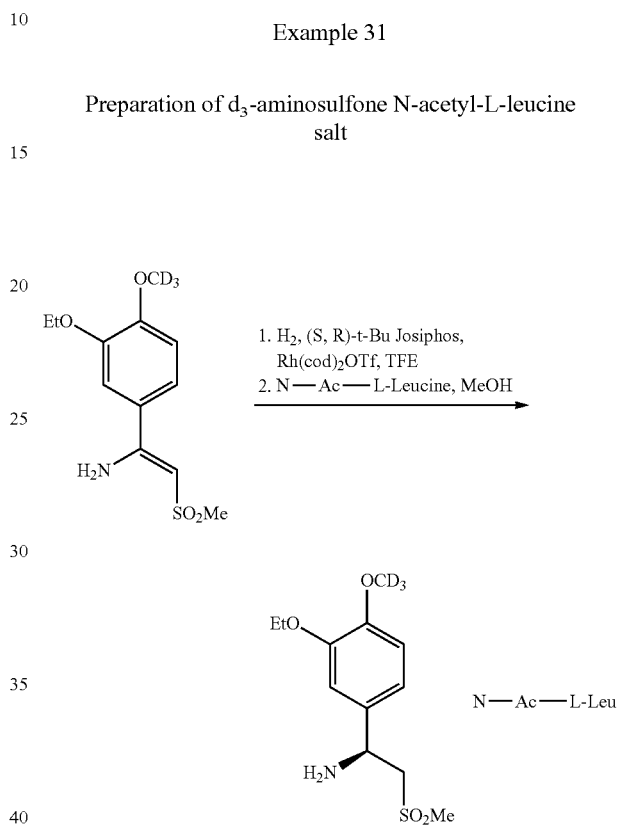

d$_3$-Enamine (2.0 g, 7.3 mmol) was added to a solution of Rh(cod)$_2$OTf (8.9 mg, 0.018 mmol) and (S,R)-t-Bu-Josiphos (9.89 mg, 0.018 mmol) in 2,2,2-trifluoroethanol (10 mL), and the resulting mixture was hydrogenated under 50 psi hydrogen at 50° C. for 16 h. When the reaction was complete, Ecosorb C-941 (0.2 g) was charged to flask and the mixture was stirred at room temperature for 3 hours. The mixture was filtered through celite into a 50 mL jacket flask, the celite pad was washed with 2,2,2-trifluoroethanol (2 mL). The batch was heated to 55° C. and a solution of (S)-2-acetamido-4-methylpentanoic acid (1.263 g, 7.29 mmol) (N—Ac-Leu) in methanol (14 ml) was charged over 1 hour. The batch was cooled to room temperature and filtered, washed with methanol (4 mL) and dried under vacuum, providing 2.6 g of the product, in 79% yield; HPLC (Hypersil BDS C$_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 8.54 (99.8%): chiral HPLC (Chiralpak AD-H 5.0 µm Daicel, 250× 4.6 mm, 1.0 mL/min, 280 nm, 50:40:10 heptane-EtOH-i-PrOH): 6.94 (0.53%), 7.55 (99.47%); $^1$H NMR (d$_6$-DMSO) δ 0.86 (dd, J=6.5, 14.1 Hz, 6H), 1.33 (t, J=6.9 Hz, 3H), 1.42-1.54 (m, 2H), 1.61 (dd, J=6.9, 13.5 Hz, 1H), 1.83 (s, 3H), 2.94 (s, 3H), 3.23-3.37 (m, 1H), 3.37-3.51 (m, 1H), 4.02 (q, J=7.0

Hz, 2H), 4.18 (q, J=7.8 Hz, 1H), 4.29 (dd, J=4.1, 9.0 Hz, 1H), 6.89 (s, 2H), 7.03 (s, 1H), 8.03 (d, J=8.1 Hz, 1H).

Example 32

Preparation of d$_4$-aminosulfone N-acetyl-L-leucine salt

2H), 4.02 (q, J=7.0 Hz, 2H), 4.18 (q, J=7.7 Hz, 1H), 6.81-6.96 (m, 2H), 7.03 (s, 1H), 8.04 (d, J=7.9 Hz, 1H).

Example 33

Preparation of d6-aminosulfone N-acetyl-L-leucine salt

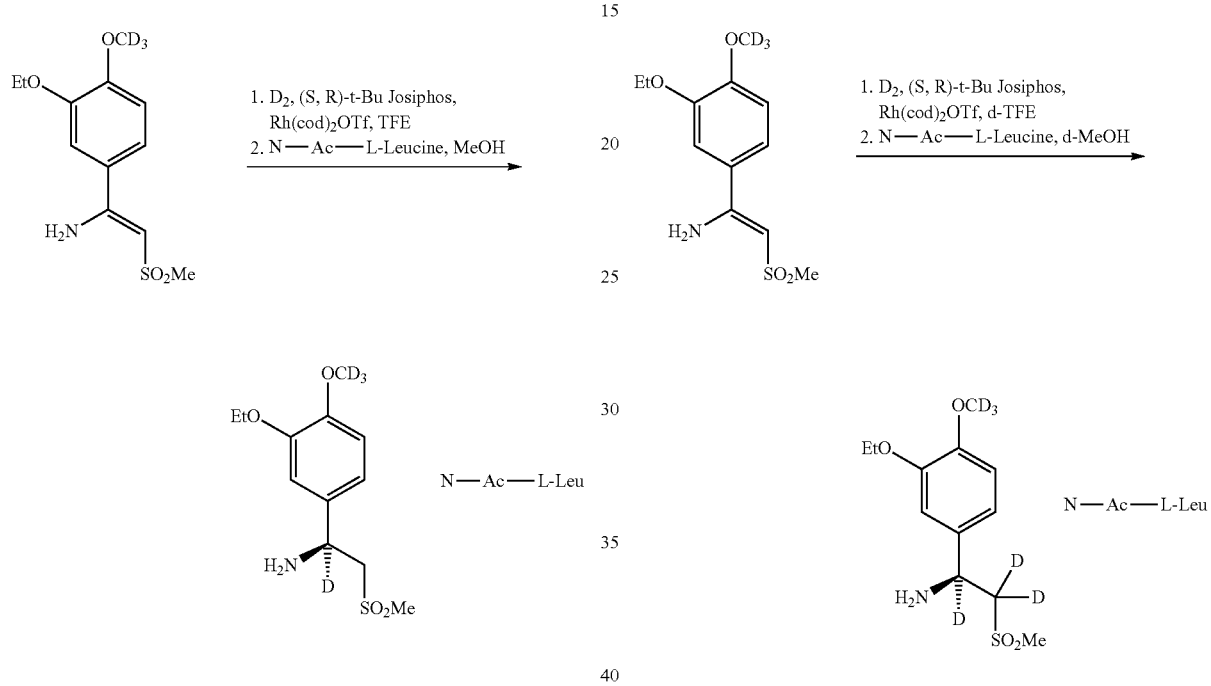

d$_3$-Enamine-(3 g, 10.93 mmol) was added to a solution of Rh(cod)$_2$OTf (13 mg, 0.027 mmol) and (S,R)-t-Bu-Josiphos (15 mg, 0.027 mmol) in d-2,2,2-trifluoroethanol (15 mL), and the resulting mixture was stirred under 50 psi deuterium gas at 50° C. for 16 h. Then, Ecosorb C-941 (0.3 g) was added and the mixture was stirred at room temperature for 3 hours, and was then filtered through celite. The mixture was heated to 55° C. and a solution of(S)-2-acetamido-4-methylpentanoic acid (1.89 g, 10.9 mmol) (N—Ac-Leu) in methanol (21 ml) was added over 1 hour. The batch was held at 55° C. for 1 hour, cooled to 20° C. over 2 hours and then stirred at 20° C. overnight. The precipitate was filtered, washed with methanol (6 mL), and dried under vacuum, providing 4.3 g of product, in 86% yield; HPLC (Hypersil BDS C$_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 7.28 (99.8%); chiral HPLC (Chiralpak AD-H 5.0 µm Daicel, 250×4.6 mm, 1.0 mL/min, 280 nm, 50:40:10 heptane-EtOH-i-PrOH): 5.37 (0.08%), 5.92 (99.92%); $^1$H NMR (DMSO-d$_6$) δ 0.77-0.96 (m, 6H), 1.24-1.38 (m, 3H), 1.40-1.53 (m, 2H), 1.55-1.74 (m, 1H), 1.75-1.91 (m, 3H), 2.87-3.02 (m, 3H), 3.21-3.54 (m, d$_3$-Enamine (3.0 g, 10.93 mmol) was added to a solution of Rh(cod)$_2$OTf (13 mg, 0.027 mmol) and (S,R)-1-Bu-Josiphos (15 mg, 0.027 mmol) in 2,2,2-trifluoroethanol (15 mL), and the resulting mixture was stirred under 50 psi deuterium gas at 50° C. for 16 h. Then, Ecosorb C-941 (0.3 g) was added and the mixture was stirred at room temperature for 3 hours, and was then filtered through celite. The mixture was heated to 55° C. and a solution of(S)-2-acetamido-4-methylpentanoic acid (1.89 g, 10.9 mmol) (N—Ac-Leu) in methanol (24 ml) was added over 1 hour. The batch was held at 55° C. for 1 hour, cooled to 20° C. over 2 hours and then stirred at 20° C. overnight. The precipitate was filtered, washed with d-methanol (6 mL), and dried under vacuum, providing 4.2 g of product, in 85% yield; HPLC (Hypersil BDS C$_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 7.03 (99.5%); chiral HPLC (Chiralpak AD-H 5.0 µm Daicel, 250×4.6 mm, 1.0 mL/min, 280 nm, 50:40:10 heptane-EtOH-i-PrOH): 5.39 (0.48%), 5.92 (99.52%); $^1$H NMR (d$_6$-DMSO) δ 0.83-0.90 (m, 6H), 1.30-1.35 (t, J=7.0 Hz, 3H), 1.45-1.50 (m, 2H), 1.60-1.64 (m, 1H), 1.83 (s, 3H), 2.94 (s, 3H), 4.02 (q, J=7.0 Hz, 2H), 4.15-4.19 (m, 1H), 6.81-6.96 (m, 2H), 7.04 (s, 1H), 8.03 (d, J=6.0 Hz, 1H).

Example 34

Preparation of $d_9$-aminosulfone N-acetyl-L-leucine salt

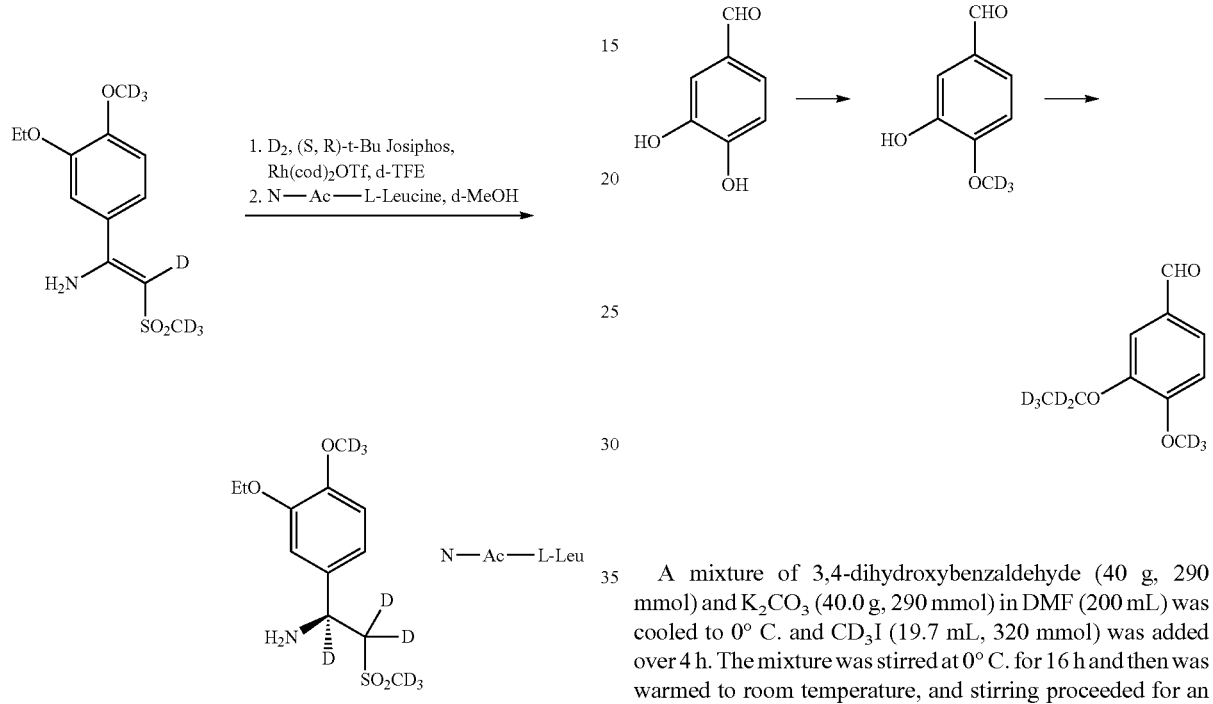

$d_7$-Enamine (4 g, 14.27 mmol) was added to a solution of Rh(cod)$_2$OTf (17 mg, 0.036 mmol) and (S,R)-t-Bu-Josiphos (19 mg, 0.036 mmol) in d-2,2,2-trifluoroethanol (20 mL), and the resulting mixture was stirred under 50 psi deuterium gas at 50° C. for 16 h. Then the mixture was cooled to room temperature. Ecosorb C-941 (0.4 g) was added and the mixture was stirred at room temperature for 3 hours. The mixture was filtered through celite and was then heated to 55° C. and a solution of $d_2$-(S)-2-acetamido-4-methylpentanoic acid (2.5 g, 14.3 mmol) ($d_2$-N—Ac-Leu) in d-methanol (28 ml) was charged over 1 hour, and then the mixture was cooled to room temperature. The precipitated solid was filtered, washed with d-methanol (8 mL) and dried under vacuum, providing 5.6 g, in 85% yield; achiral HPLC (Hypersil BDS C$_8$, 5.0 m, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 7.31 (99.9%); chiral HPLC (Chiralpak AD-H 5.0 μm Daicel, 250× 4.6 mm, 1.0 mL/min, 280 nm, 50:40:10 heptane-EtOH-i-PrOH): 5.39 (0.19%), 5.88 (99.8%); $^1$H NMR (d$_6$-DMSO) d 0.87 (dd, J=6.5, 14.4 Hz, 6H), 1.33 (t, J=7.0 Hz, 3H), 1.41- 1.52 (m, 2H), 1.52-1.71 (m, 1H), 1.83 (s, 3H), 4.02 (q, J=7.0 Hz, 2H), 4.12-4.24 (m, 1H), 6.89 (s, 2H), 6.99-7.11 (m, 1H), 7.03 (s, 1H).

Example 35

Preparation of 3-(d$_5$-ethoxy)-4-(d$_3$-methoxy)-benzaldehyde

A mixture of 3,4-dihydroxybenzaldehyde (40 g, 290 mmol) and K$_2$CO$_3$ (40.0 g, 290 mmol) in DMF (200 mL) was cooled to 0° C. and CD$_3$I (19.7 mL, 320 mmol) was added over 4 h. The mixture was stirred at 0° C. for 16 h and then was warmed to room temperature, and stirring proceeded for an additional 20 h. The mixture was diluted with ethyl acetate (600 mL) and filtered through a pad of Celite. The filtrate was concentrated to give a brown oil, which was then redissolved in EtOAc (600 mL). Water (200 mL) was added and the pH was adjusted to pH ~3 by the addition of 1N HCl. The organic layer was separated and the aqueous phase was extracted with EtOAc (2×200 mL). The combined organic solution was dried (Na$_2$SO$_4$) and concentrated. The crude material was purified by silica gel column chromatography using a hexanes-ethyl acetate gradient. The product thus obtained was recrystallized from dichloromethane/hexanes to give 11.5 g of d$_3$-isovanillin (25.6%); $^1$H NMR (CDCl$_3$) δ 5.74 (s, 1H), 6.97 (dd, J=6.3, 2.4 Hz, 1H), 7.42-7.45 (m, 2H), 9.98 (s, 1H); HPLC (Waters Nova-pack C$_{18}$, 4.0 μm, 150×3.9 mm, 1.0 mL/min, 278 nm, 70/30 isocratic acetonitrile/water with 1% TFA, 15 min): 1.92 (98.4%).

To a mixture of thus formed d$_3$-isovanillin (11.0 g, 70.9 mmol), and K$_2$CO$_3$ (19.6 g, 142 mmol) in DMF (40 mL) was added d$_5$-ethyl iodide (6.80 ml, 84.5 mmol) in dropwise fashion, and the mixture was stirred at rt for 2 days. The reaction was quenched with 500 mL of ice-water. The precipitated product was collected by filtration and washed with water (100 mL). The product was dried under vacuum to provide 12.6 g (94%) of produc; $^1$H NMR (CDCl$_3$) δ 6.97 (d, J=8.1 Hz, 1H), 7.40 (d, J=1.9 Hz, 1H), 7.44 (dd J=8.1, 1.9 Hz, 1H), 9.84 (s, 1H); HPLC (Waters Nova-pack C$_{18}$, 4.0 μm, 150×3.9

Example 36

Preparation of 3-($d_5$-ethoxy)-4-($d_3$-methoxy)-benzonitrile

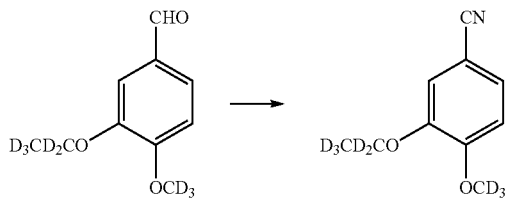

A mixture of hydroxylamine hydrochloride (5.4 g, 78 mmol) in acetonitrile (16 mL) was warmed to 72° C., and a solution of $d_8$-3-ethoxy-4-methoxybenzaldehyde (12.2 g, 64.8 mmol) in acetonitrile (18 mL) was added. The mixture was stirred for 12 h at this temperature and then cooled to room temperature. Water (70 mL) was added, and the product was collected by filtration and dried under vacuum to provide the desired product (11.8 g, 98%); $^1$H NMR (CDCl$_3$) δ 6.89 (d J=8.4 Hz, 1H), 7.06 (d, J=1.8 Hz, 1H), 7.26 (dd J=8.4, 1.8 Hz, 1H); HPLC (Waters Nova-pack C$_{18}$, 4.0 μm, 150×3.9 mm, 1.0 mL/min, 278 nm, 70/30 isocratic acetonitrile/water with 1% TFA, 15 min): 7.74 (97.2%).

Example 37

Preparation of $d_8$-enamine

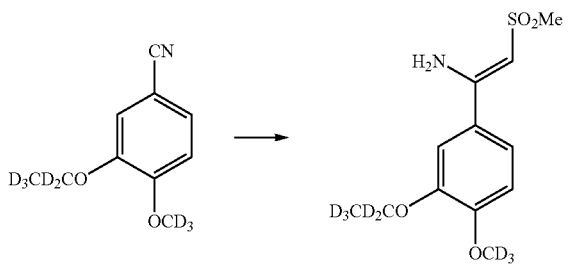

A mixture of dimethylsulfone (2.03 g, 21.6 mmol) in THF (15.9 mL) was cooled to 0° C., and n-butyllithium (12.1 mL, 19.3 mmol) was added dropwise. The mixture was stirred at 0° C. for 1 h, and then a solution of $d_8$-benzonitrile (2.0 g, 10.8 mmol) in THF (6.0 mL) was added over 30 min. After completion of the addition, the mixture was warmed to 25-30° C. and stirred at that temperature for 3 h, and then water (25 mL) was added in dropwise fashion. The resulting slurry was stirred at 28° C. overnight and then cooled to 5° C. The precipitated product was collected by filtration, washed with 2:1 water/THF (10 mL), water (2×10 mL) and hexane (2×10 mL), and dried under vacuum to provide 2.4 g (82%); $^1$H NMR (CDCl$_3$) δ 2.99 (s, 3H), 3.32 (s, 2H), 6.81 (br, 2H), 7.00 (d, J=8.4 Hz, 1H), 7.12 (d, J=2.1 Hz, 1H,), 7.17 (dd J=8.4, 2.1 Hz, 1H,); HPLC (Hypersil BDS C$_8$, 5.0 μm, 250× 4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 13.60 (99.0%).

Example 38

Preparation of $d_{12}$-enamine

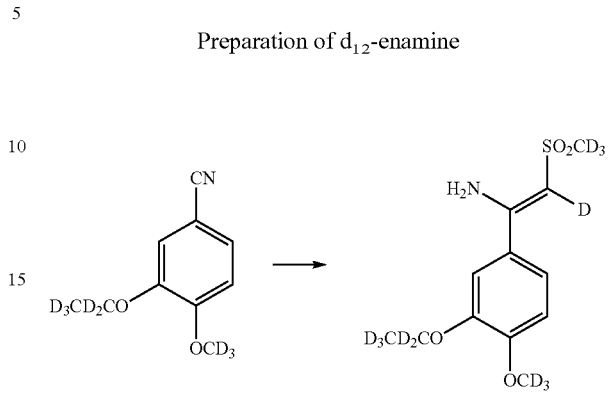

A mixture of $d_6$-dimethylsulfone (4.33 g, 43.2 mmol) in THF (31.8 mL) was cooled to 0° C., and n-butyllithium (24.2 mL, 38.7 mmol) was added over 1 h. The resulting mixture was stirred at 0° C. for 1 h. Then, a solution of $d_8$-benzonitrile (4.0 g, 21.6 mmol) in THF (11.5 mL) was added over 30 min and then the mixture was warmed to 25-30° C. over 30 min. The mixture was stirred at this temperature for 3 h then deuterium oxide (41.2 mL, 2290 mmol) was added dropwise. Organic solvent was evaporated under reduced pressure until precipitate formed. The precipitated product was filtered, washed with MTBE (10 mL, and dried under vacuum to afford 4.3 g of the product, in 70% yield; $^1$H NMR (CDC$_3$) δ 7.00 (d J=8.4 Hz, 1H,), 7.12 (d, J=1.8 Hz, 1H), 7.17 (dd, J=8.4, 2.1 Hz, 1H,); HPLC (Hypersil BDS C$_8$, 5.0 μm, 250× 4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 13.58 (97.58%).

Example 39

Preparation of $d_9$-aminosulfone N-acetyl-L-leucine salt

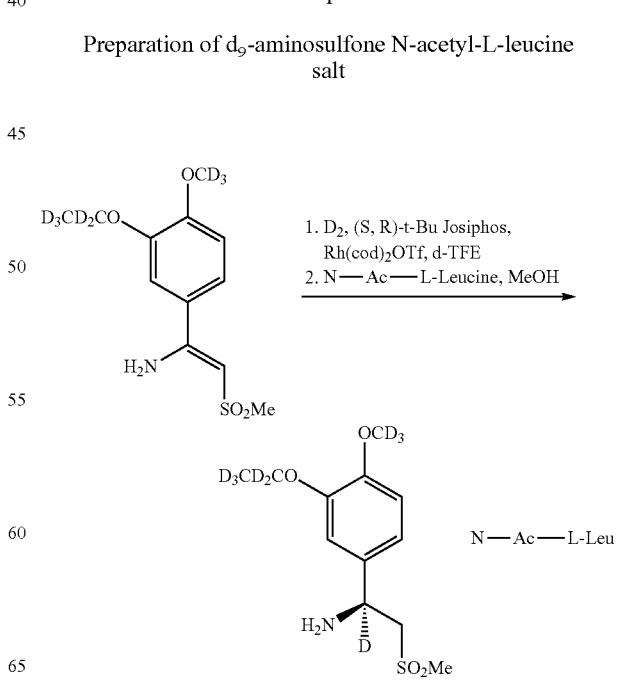

$d_8$-Enamine (2.0 g, 7.3 mmol) was added to a solution of Rh(cod)$_2$OTf (8.9 mg, 0.018 mmol) and (S,R)-t-Bu-Josiphos (9.89 mg, 0.018 mmol) in 2,2,2-trifluoroethanol (10 mL), and the resulting mixture was stirred under 50 psi deuterium at 50° C. for 16 h. When the reaction was complete, Ecosorb C-941 (0.2 g) was charged to flask and the mixture was stirred at room temperature for 3 hours. The mixture was filtered through celite into a 50 mL jacket flask, the celite pad was washed with 2,2,2-trifluoroethanol (2 mL). The batch was heated to 55° C. and a solution of (S)-2-acetamido-4-methylpentanoic acid (1.89 g, 10.9 mmol) (N—Ac-Leu) in methanol (24 ml) was added over 1 hour. The batch was cooled to room temperature and filtered, washed with methanol (2×10 mL) and dried under vacuum, providing 3.3 g of the product, in 68% yield; HPLC (Hypersil BDS C$_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 6.61 (99.44%); chiral HPLC (Chiralpak AD-H 5.0 µm Daicel, 250×4.6 mm, 1.0 mL/min, 280 nm, 50:40:10 heptane-EtOH-i-PrOH): 5.51 (0.29%), 5.82 (99.71%); $^1$H NMR (d$_6$-DMSO) δ 0.86 (dd, J=7.5, 15.0 Hz, 6H), 1.45-1.50 (m, 2H), 1.58-1.67 (m, 1H), 1.83 (s, 3H), 4.18 (m, 1H), 6.89 (s, 2H), 7.03 (s, 1H), 8.04 (d, J=9.0 Hz, 1H).

Example 40

Preparation of d$_4$-aminosulfone N-acetyl-L-leucine salt

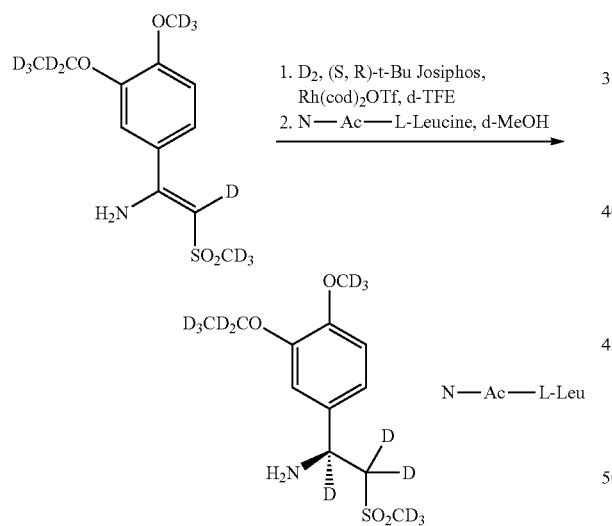

$d_{12}$-Enamine (3 g, 14.27 mmol) was added to a solution of Rh(cod)$_2$OTf (12 mg, 0.036 mmol) and (S,R)-t-Bu-Josiphos (14 mg, 0.036 mmol) in d-2,2,2-trifluoroethanol (15 mL), and the resulting mixture was stirred under 50 psi deuterium gas at 50° C. for 40 h. Then the mixture was cooled to room temperature. Ecosorb C-941 (0.4 g) was added and the mixture was stirred at room temperature for 3 hours. The mixture was filtered through celite and was then heated to 55° C. and a solution of (S)-2-acetamido-4-methylpentanoic acid (2.5 g, 14.3 mmol) (N—Ac-Leu) in d-methanol (28 ml) was charged over 1 hour, and then the mixture was cooled to room temperature. The precipitated solid was filtered, washed with d-methanol (8 mL) and dried under vacuum, providing 5.6 g, in 85% yield; achiral HPLC (Hypersil BDS C$_8$, 5.0 µm, 250×4.6 mm, 1.5 mL/min, 278 nm, 90/10 gradient to 80/20 0.1% aqueous TFA/MeOH over 10 min then gradient to 10/90 0.1% aqueous TFA/MeOH over the next 15 min): 7.31 (99.9%); chiral HPLC (Chiralpak AD-H 5.0 µm Daicel, 250×4.6 mm, 1.0 mL/min, 280 nm, 50:40:10 heptane-EtOH-i-PrOH): 5.39 (0.19%), 5.88 (99.8%); $^1$H NMR (d$_6$-DMSO) d 0.87 (dd, J=6.5, 14.4 Hz, 6H), 1.33 (t, J=7.0 Hz, 3H), 1.41-1.52 (m, 2H), 1.52-1.71 (m, 1H), 1.83 (s, 3H), 4.02 (q, J=7.0 Hz, 2H), 4.12-4.24 (m, 1H), 6.89 (s, 2H), 6.99-7.11 (m, 1H), 7.03 (s, 1H).

Example 41

Preparation of d$_3$-Compound A

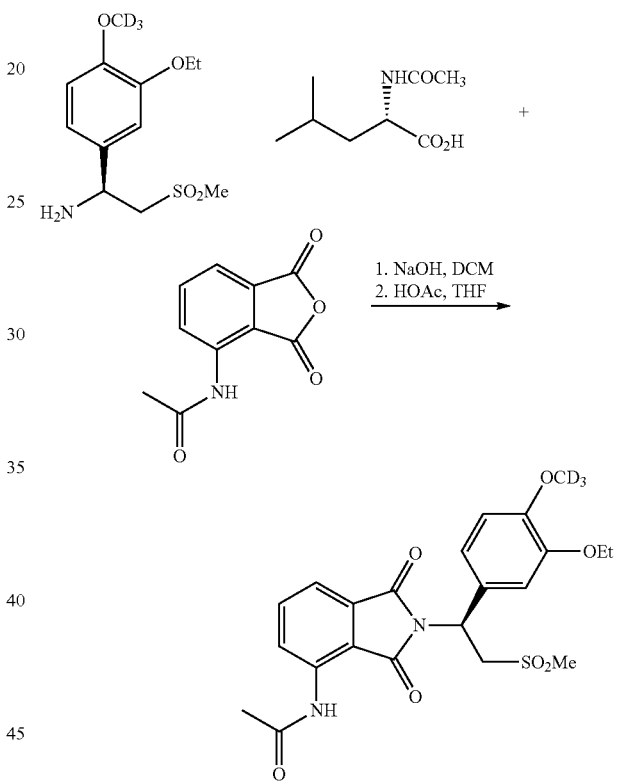

To a slurry of d$_3$-aminosulfone leucine salt (2.2 g, 4.89 mmol) in dichloromethane (20 mL) was charged 17% aqueous NaOH (2.2 mL). The mixture was stirred for 5 minutes at room temperature, and then the organic layer was dried (MgSO$_4$) and evaporated. To the residue was added THF (13.2 mL), acetic acid (3.27 g, 57.3 mmol) and N-(1,3-dioxo-1,3-dihydroisobenzofuran-4-yl)acetamide (1.00 g, 4.89 mmol). The resulting mixture was heated at 70° C. for 24 hours. The batch was cooled to 35° C., THF (12 mL) and iPrOAc (24 mL) were added, the reaction mixture was washed with 10% NaH$_2$PO$_4$ solution (3×7 mL), and water (3×7 mL), and was evaporated to dryness. To the residue was added iPrOAc (3×20 mL), and the mixture was evaporated to dryness. The residue was dissolved in iPrOAc (9 mL) and the product was precipitated by adding MTBE (13 mL) slowly. The precipitate was filtered, washed with MTBE (4.4 mL) and dried under vacuum. The crude product was recrystallized in acetone-EtOH (7 mL:22 mL), providing 1.7 g of the product, in 79% yield; UPLC (BEH C$_{18}$, 1.7 µm, 2.1×50 mm, 0.6 mL/min, 230 nm, 95/5 gradient to 15/85 0.06% aqueous TFA/Acetonitrile (0.06% TFA) over 5 min): 2.60 (99.9%); chiral HPLC (Chiralpak AD-H 5.0 μm Daicel, 250×4.6 mm, 1.0 mL/min, 280 nm, 70:30 heptane-EtOH): 13.32 (0.51%), 15.30 (99.49%); $^1$H NMR (d$_6$-DMSO) δ 1.32 (t, J=6.9 Hz, 3H), 2.19 (s, 3H), 3.02 (s, 3H), 4.02 (q, J=7.0 Hz, 2H), 4.09-4.23 (m, 1H), 4.35 (dd, J=10.7, 14.3 Hz, 1H), 5.78 (dd, J=4.2, 10.4 Hz, 1H), 6.88-7.03 (m, 2H), 7.07 (d, J=1.7 Hz, 1H), 7.57 (d, J=7.2 Hz, 1H), 7.79 (t, J=7.8 Hz, 1H), 8.44 (d, J=8.3 Hz, 1H), 9.72 (s, 1H); $^{13}$C NMR (d$_6$-DMSO) δ 14.63, 24.15, 41.03, 47.16, 52.87, 63.87, 111.79, 112.42, 116.66, 118.18, 119.71, 126.10, 129.42, 131.33, 135.89, 136.48, 147.86, 148.91, 166.89, 167.80, 169.21; Anal. (C$_{22}$H$_{21}$D$_3$N$_2$O$_7$S) C, H, N. Calcd C, 57.00; H, 5.22; N, 6.04. Found C, 57.15; H, 5.51; N, 6.04.

Example 42

Preparation of d$_7$-Compound A

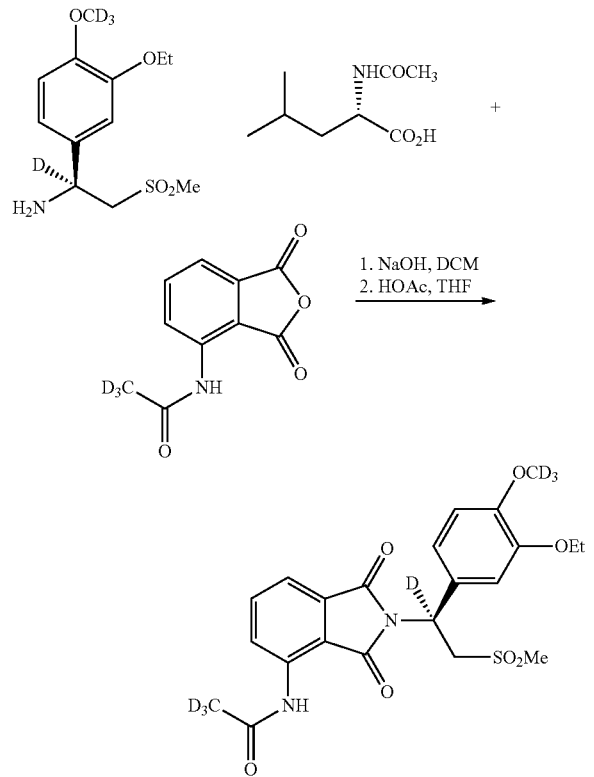

To slurry of aminosulfone leucine salt (3 g, 6.64 mmol) in dichloromethane (30 mL) was added 17% aqueous NaOH (3 mL). The mixture was stirred for 5 minutes and the organic layer was dried (MgSO$_4$) and evaporated. To the residue was added THF (18 mL), d1-acetic acid (4.75 g, 78 mmol) and d$_3$-N-(1,3-dioxo-1,3-dihydroisobenzofuran-4-yl)acetamide (1.38 g, 6.64 mmol). The resulting mixture was heated at 72° C. for 24 hours. Then the mixture was cooled to 35° C., THF (18 mL) and iPrOAc (36 mL) were added, and the reaction mixture was washed with 10% NaH$_2$PO$_4$ solution (3×9 mL), and water (3×9 mL), and the organic phase was evaporated to dryness. To the residue was added i-PrOAc (3×30 mL), and the mixture was evaporated to dryness. The residue was dissolved in i-PrOAc (12 mL) and the product was precipitated by adding MTBE (18 mL) slowly. The precipitate was filtered, washed with MTBE (6 mL) and dried under vacuum. The crude product was recrystallized in acetone-EtOH (9 mL:28 mL), providing 2 g of the product, in 75% yield; UPLC (BEH C$_{18}$, 1.7 μm, 2.1×50 mm, 0.6 mL/min, 230 nm, 95/5 gradient to 15/85 0.06% aqueous TFA/Acetonitrile (0.06% TFA) over 5 min): 2.54 (99.3%); chiral HPLC (Chiralpak AD-H 5.0 μm Daicel, 250×4.6 mm, 1.0 mL/min, 280 nm, 70:30 heptane-EtOH): 12.86 (0.34%), 14.61 (99.66%); $^1$H NMR (d$_6$-DMSO) δ 1.31 (t, J=6.9 Hz, 3H), 2.89-3.16 (m, 3H), 4.01 (q, J=6.9 Hz, 2H), 4.12 (d, J=14.4 Hz, 1H), 4.27-4.44 (m, 1H), 6.78-7.03 (m, 2H), 7.06 (s, 1H), 7.56 (d, J=7.2 Hz, 1H), 7.78 (t, J=7.8 Hz, 1H), 8.43 (d, J=8.3 Hz, 1H), 9.70 (s, 1H); $^{13}$C NMR (d$_6$-DMSO) δ 14.63, 41.03, 52.80, 63.87, 111.69, 111.79, 112.43, 116.66, 118.15, 119.72, 126.08, 129.27, 129.36, 131.32, 135.87, 136.46, 147.85, 148.93, 166.88, 167.78, 169.24; Anal. (C$_{22}$H$_{17}$D$_7$N$_2$O$_7$S) C, H, N. Calcd C, 56.51; H, 5.17; N, 5.99. Found C, 56.58; H, 5.12; N, 5.95.

Example 43

Preparation of d$_9$-Compound A

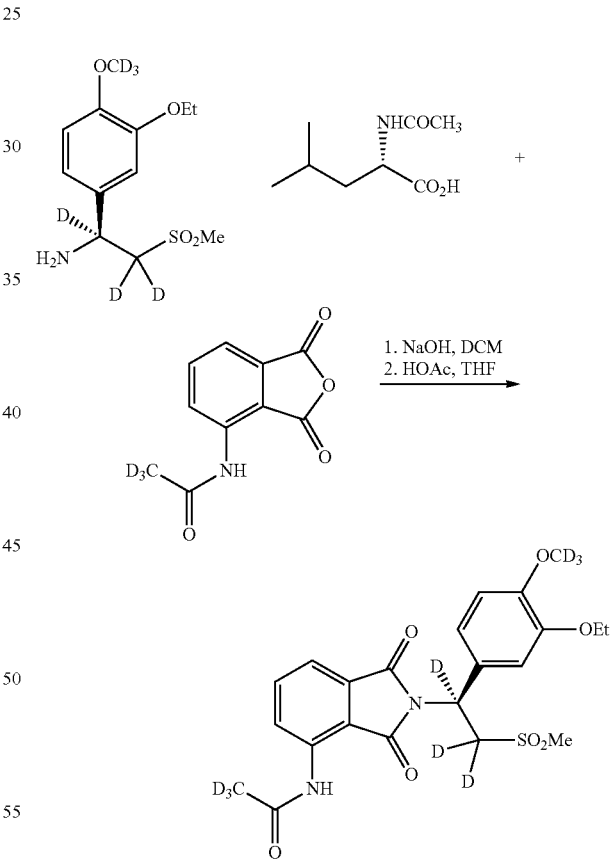

To slurry of aminosulfone leucine salt (3.0 g, 6.6 mmol) in dichloromethane (30 mL) was added 17% aqueous NaOH (3 mL). The mixture was stirred for 5 minutes and the organic layer was dried (MgSO$_4$) and evaporated. To the residue was added THF (18 mL), d$_1$-acetic acid (4.74 g, 78 mmol) and d$_3$-N-(1,3-dioxo-1,3-dihydroisobenzofuran-4-yl)acetamide (1.38 g, 6.63 mmol). The resulting mixture was heated at 73° C. for 24 hours, and then the mixture was cooled to 35° C. THF (18 mL) and i-PrOAc (36 mL) were added, and the mixture was washed with 10% NaH$_2$PO$_4$ solution (3×9 mL), and water (3×9 mL), and the organic phase was evaporated to dryness. To the residue was added i-PrOAc (3×30 mL), and the mixture was evaporated to dryness. The residue was dissolved in i-PrOAc (12 mL) and the product was precipitated by adding MTBE (18 mL) slowly. The precipitate was filtered, washed with MTBE (6 mL) and dried under vacuum. The crude product was recrystallizated in acetone-EtOH (9 mL:28 mL), providing 2.0 g of the product, in 69% yield; UPLC (BEH C$_{18}$, 1.7 µm, 2.1×50 mm, 0.6 mL/min, 230 nm, 95/5 gradient to 15/85 0.06% aqueous TFA/Acetonitrile (0.06% TFA) over 5 min): 2.54 (99.9%); chiral HPLC (Chiralpak AD-H 5.0 µm Daicel, 250×4.6 mm, 1.0 mL/min, 280 nm, 70:30 heptane-EtOH): 12.52 (0.32%), 14.21 (99.68%); $^1$H NMR (d$_6$-DMSO) δ 1.32 (t, J=7.0 Hz, 3H), 2.96-3.06 (m, 3H), 4.02 (d, J=7.0 Hz, 2H), 6.90-7.03 (m, 2H), 7.05-7.12 (m, 1H), 7.57 (d, J=6.8 Hz, 1H), 7.69-7.92 (m, 1H), 8.44 (d, J=8.1 Hz, 1H), 9.71 (s, 1H); $^{13}$C NMR (d$_6$-DMSO) δ 14.63, 41.00, 52.57, 63.87, 111.69, 111.79, 112.42, 116.66, 118.15, 119.71, 126.08, 129.35, 131.33, 135.87, 136.46, 147.85, 148.93, 166.88, 167.78, 169.25; Anal. (C$_{22}$H$_{15}$D$_9$N$_2$O$_7$S) C, H, N. Calcd C, 56.27; H, 5.15; N, 5.97. Found C, 56.34; H, 5.16; N, 5.93.

Example 44

Preparation of d$_9$-Compound A

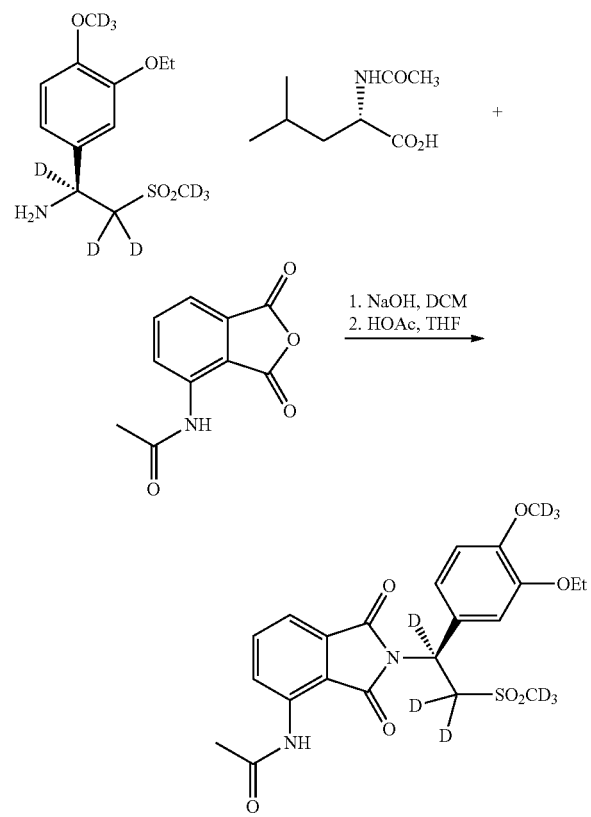

To a slurry of aminosulfone leucine salt (2.5 g, 5.44 mmol) in dichloromethane (25 mL) was added 17% aqueous NaOH (2.5 mL). The mixture was stirred for 5 minutes and the organic layer was dried (MgSO$_4$) and evaporated under vacuum. To the residue was added THF (15 mL), d$_6$-acetic acid (4.1 g, 63.6 mmol) and N-(1,3-dioxo-1,3-dihydroisobenzofuran-4-yl)acetamide (1.12 g, 5.44 mmol). The resulting mixture was heated at 70° C. for 24 hours, and then the mixture was cooled to 35° C. THF (15 mL) and iPrOAc (30 mL) were added, and the mixture was washed with 10% NaH$_2$PO$_4$ solution (3×7.5 mL), and water (3×7.5 mL), and the organic phase was evaporated to dryness. To the residue was added i-PrOAc (3×20 mL), and the mixture was evaporated to dryness. The residue was dissolved in i-PrOAc (10 mL) and the product was precipitated by adding MTBE (15 mL) slowly. The precipitate was filtered, washed with MTBE (5 mL) and dried under vacuum. The crude product was recrystallized in acetone-EtOH (7.6 mL:24 mL), providing 1.85 g of the product, in 76% yield; UPLC (BEH C$_{18}$, 1.7 µm, 2.1×50 mm, 0.6 mL/min, 230 nm, 95/5 gradient to 15/85 0.06% aqueous TFA/Acetonitrile (0.06% TFA) over 5 min): 2.55 (99.7%); chiral HPLC (Chiralpak AD-H 5.0 µm Daicel, 250×4.6 mm, 1.0 mL/min, 280 nm, 70:30 heptane-EtOH): 13.04 (0.43%), 14.90 (99.57%); $^1$H NMR (d$_6$-DMSO) δ 1.32 (t, J=6.9 Hz, 3H), 2.19 (s, 3H), 4.02 (q, J=6.9 Hz, 2H), 6.86-7.03 (m, 2H), 7.03-7.19 (m, 1H), 7.57 (d, J=7.2 Hz, 1H), 7.79 (t, J=7.8 Hz, 1H), 8.44 (d, J=8.3 Hz, 1H), 9.71 (s, 1H); $^{13}$C NMR (d$_6$-DMSO) δ 14.63, 24.15, 63.87, 111.69, 111.79, 112.43, 116.66, 118.16, 119.72, 126.08, 129.26, 129.35, 131.33, 135.88, 136.49, 147.86, 148.93, 166.89, 167.80, 169.20; Anal. (C$_{22}$H$_{15}$D$_9$N$_2$O$_7$S) C, H, N. Calcd C, 56.27; H, 5.15; N, 5.97. Found C, 56.58; H, 5.12; N, 5.95.

Example 45

Preparation of d$_{12}$-Compound A

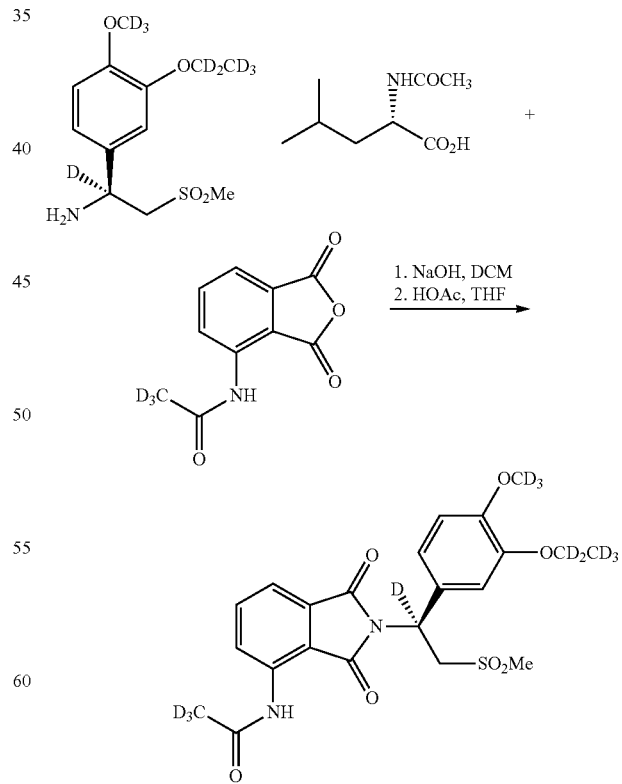

To slurry of aminosulfone leucine salt (2.3 g, 5.2 mmol) in dichloromethane (23 mL) was added 17% aqueous NaOH (2.3 mL). The mixture was stirred for 5 minutes and the organic layer was dried (MgSO$_4$) and evaporated under vacuum. To the residue was added THF (14 mL), d-acetic acid (3.74 g, 61.2 mmol) and d$_3$-N-(1,3-dioxo-1,3-dihydroisobenzofuran-4-yl)acetamide (1.09 g, 5.23 mmol). The resulting mixture was heated at 73° C. for 43 hours, and then the mixture was cooled to 35° C. THF (12 mL) and i-PrOAc (24 mL) were added, and the reaction mixture was washed with 10% NaH$_2$PO$_4$ solution (3×7 mL) and water (3×7 mL), and the organic phase was evaporated to dryness. To the residue was added i-PrOAc (3×20 mL), and the mixture was evaporated to dryness. The residue was dissolved in i-PrOAc (9 mL) and the product was precipitated by adding MTBE (14 mL) slowly. The precipitate was filtered, washed with MTBE (5 mL) and dried under vacuum. The crude product was recrystallizated in acetone-EtOH (9 mL:28 mL), providing 1.66 g of product, in 73% yield; UPLC (BEH C$_{18}$, 1.7 μm, 2.1×50 mm, 0.6 mL/min, 230 nm, 95/5 gradient to 15/85 0.06% aqueous TFA/Acetonitrile (0.06% TFA) over 5 min): 2.53 (100%); chiral HPLC (Chiralpak AD-H 5.0 μm Daicel, 250×4.6 mm, 1.0 mL/min, 280 nm, 70:30 heptane-EtOH): 12.06 (0.29%), 13.62 (99.71%); $^1$H NMR (d-DMSO) δ 3.01 (s, 3H), 4.13 (d, J=14.4 Hz, 1H), 4.25-4.43 (m, 1H), 6.79-7.03 (m, 2H), 7.03-7.14 (m, 1H), 7.56 (d, J=6.6 Hz, 1H), 7.72-7.86 (m, 1H), 8.43 (d. J=8.3 Hz, 1H), 9.70 (s, 1H); $^{13}$C NMR (d$_6$-DMSO) δ 41.05, 47.16, 52.81, 111.50, 111.69, 111.79, 112.41, 116.66, 118.16, 119.70, 126.08, 129.27, 129.38, 131.33, 135.88, 136.48, 142.54, 147.88, 148.93, 166.89, 167.78, 169.25; Anal. (C$_{22}$H$_{12}$D$_{12}$N$_2$O$_7$S) C, H, N. Calcd C, 55.91; H, 5.12; N, 5.93. Found C, 56.10; H, 5.03; N, 6.05.

Example 46

Preparation of d$_7$-Compound A

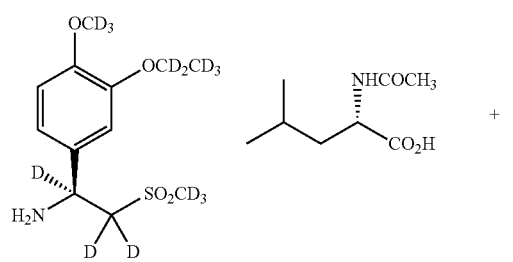

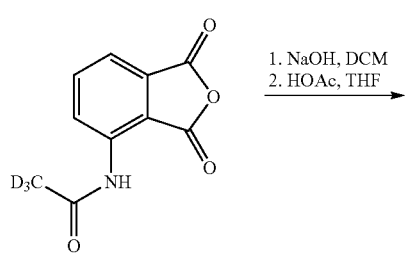

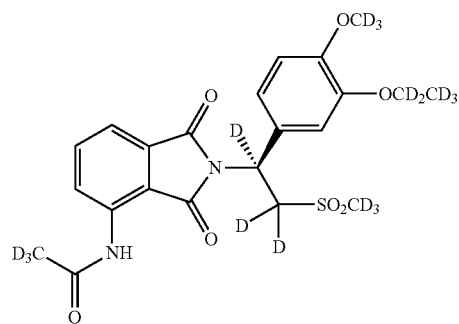

To slurry of aminosulfone leucine salt (3.0 g, 6.6 mmol) in dichloromethane (30 mL) was added 17% aqueous NaOH (3 mL). The mixture was stirred for 5 minutes and the organic layer was dried (MgSO$_4$) and evaporated. To the residue was added THF (18 mL), d$_1$-acetic acid (4.74 g, 78 mmol) and d$_3$-N-(1,3-dioxo-1,3-dihydroisobenzofuran-4-yl)acetamide (1.38 g, 6.63 mmol). The resulting mixture was heated at 73° C. for 40 hours, and then the mixture was cooled to 35° C. i-PrOAc (18 mL) was added, and the mixture was washed with 10% NaH$_2$PO$_4$ solution (3×10 mL), and water (10 mL), and the organic phase was evaporated to dryness. To the residue was added i-PrOAc (3×30 mL), and the mixture was evaporated to dryness. The residue was dissolved in i-PrOAc (12 mL) and the product was precipitated by adding MTBE (18 mL) slowly. The precipitate was filtered, washed with MTBE (10 mL) and dried under vacuum. The crude product was recrystallizated in acetone-EtOH (9 mL:28 mL), providing 1.9 g of the product, in 67% yield; UPLC (BEH C is, 1.7 μm, 2.1×50 mm, 0.6 mL/min, 230 nm, 95/5 gradient to 15/85 0.06% aqueous TFA/Acetonitrile (0.06% TFA) over 5 min): 2.53 (99.9%); chiral HPLC (Chiralpak AD-H 5.0 μm Daicel, 250×4.6 mm, 1.0 mL/min, 280 nm, 70:30 heptane-EtOH): 12.32 (0.64%), 14.08 (99.16%); $^1$H NMR (d$_6$-DMSO) δ 6.92-6.99 (m, 2H), 7.07-7.08 (m, 1H), 7.57 (d, J=6.8 Hz, 1H), 7.76-7.81 (m, 1H), 8.45 (d, J=8.1 Hz, 1H), 9.71 (s, 1H); $^{13}$C NMR (d$_6$-DMSO) δ 111.79, 112.41, 116.65, 118.15, 119.68, 126.05, 129.35, 131.33, 135.87, 136.49, 147.89, 148.93, 166.88, 167.78, 169.25; Anal. (C$_{22}$H$_7$D$_{17}$N$_2$O$_7$S) C, H, N. Calcd C, 55.31; H, 5.06; N, 5.86. Found C, 55.43; H, 4.98; N, 5.81.

Example 47

Preparation of 3-ethoxy-4-(methoxy-d$_3$)-benzaldehyde

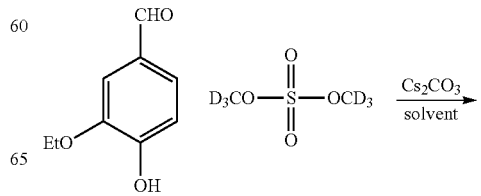

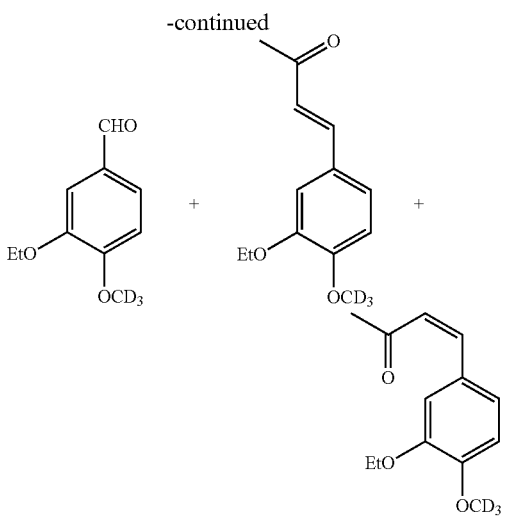

The synthesis of 3-ethoxy-4-(methoxy-d$_3$)-benzaldehyde was performed according to the scheme above. Reaction conditions were screened and the results are summarized in Table 1. When acetone was used as the solvent, and about 1.5 equiv. of Cs$_2$CO$_3$ was used, significant impurity formation was observed to the extent of ~40 Area %. LCMS and NMR indicated the side products derived from aldol condensation of the solvent acetone with the product aldehyde. LCMS showed the reaction was complete after 1.5 hours, at which time there was very little side product formation; impurities formed with extended reaction time. The formation of the impurities was suppressed in the presence of water.

TABLE 1

Reaction condition screening-methylation of 3-ethoxy-4-hydroxybenzaldehyde

| Reaction | Solvent | Cs$_2$CO$_3$ (eq.) | % product 1 h | % side product 1 h | % product 6 h | % side product 6 h | % product, 21 h | % side product 21 h |
|---|---|---|---|---|---|---|---|---|
| 1 | acetone | 1.53 | 100 | 0 | 75 | 25 | 50 | 50 |
| 2 | acetone + 5% water | 1.53 | 100 | 0 | 100 | 0 | 100 | 0 |
| 3 | acetone | 1 | 92 | 0 | 97 | 0 | 100 | 0 |
| 4 | DMF | 1.53 | ND | ND | ND | ND | 100 | 0 |

Example 48

Determination of Isotopic Enrichment

Isotopic enrichment may be confirmed and quantified by mass spectrometry and/or NMR, including, for example, proton-NMR; carbon-13 NMR; or nitrogen-15 NMR.

Isotopic enrichment may also be confirmed by single-crystal neutron diffraction. For example, the isotopic ratio at a particular hydrogen/deuterium position in a deuterated compound can be determined using single-crystal neutron diffraction. Neutron diffraction is advantageous because neutrons are scattered by the nucleus of an atom, therefore allowing for discrimination between isotopes, such as hydrogen and deuterium, that differ in the number of neutrons in the nucleus.

A single crystal of suitable size and quality comprising the deuterated compound is grown using standard methods of crystal growth. For single-crystal neutron diffraction experiments, crystals of several cubic millimeters are generally required for suitable data collection. A minimum size for a single crystal is typically about 1 cubic millimeter. Suitable single crystals are obtained by dissolving the deuterated compound in a solvent with appreciable solubility, then slowly evaporating or cooling the solution to yield crystals of suitable size and quality. Alternatively, suitable single crystals are obtained by dissolving the deuterated compound in a solvent with appreciable solubility, then slowly diffusing into the solution of antisolvent (i.e., a solvent in which the deuterated compound is not appreciably soluble) to yield crystals of suitable size and quality. These and other suitable methods of crystal growth are known in the art and are described, e.g., in George H. Stout & Lyle H. Jensen, X-Ray Structure Determination: A Practical Guide 74-92 (John Wiley & Sons, Inc. 2nd ed. 1989) (the entirety of which is incorporated herein).

After isolating a suitable single crystal comprising the deuterated compound, the crystal is mounted in a neutron beam, neutron diffraction data is collected, and the crystal structure is solved and refined. Different neutron sources can be used, including steady-state sources and pulsed spallation sources. Examples of steady-state sources include the Grenoble ILL High Flux Reactor (Grenoble, France) and the Oak Ridge High Flux Isotope Reactor (Oak Ridge, Tenn.). Examples of pulsed spallation sources include ISIS, the spallation neutron source at Rutherford Appleton Laboratory (Oxfordshire, UK); the Intense Pulsed Neutron Source (IPNS) at Argonne National Laboratory (Argonne, Ill.), the Los Alamos Neutron Science Center (LANSCE) at Los Alamos National Laboratory (Los Alamos, N. Mex.), and the Neutron Science Laboratory (KENS) at KEK (Tsukuba, Ibaraki, Japan).

For a steady-state neutron source, four-circle diffractometer techniques are used with a monochromatic beam and a single detector, rotating the crystal and detector to measure each reflection sequentially. Diffractometer control software and step-scanning methods for intensity extraction can be adopted from routine four-circle X-ray diffractometry methods. One or more area detectors, including area detector arrays, may alternatively be used to increase the region of reciprocal space accessed in a single measurement. A broad band (white) beam used with an area detector allows for Laue or quasi-Laue diffraction with a stationary crystal and detector.

For a pulse source with a white neutron beam, time-of-flight Laue diffraction techniques are used, which allow for the determination of the velocity, energy, and wavelength of each neutron detected. This approach combines wavelength sorting with large area position-sensitive detectors, and allows for fixed scattering geometries (i.e. a stationary crystal and detector). Pulse source data collected in this fashion allows for rapid collection of data sets and good accuracy and precision in standard structural refinements. Additional details regarding steady-state and pulse source neutron diffraction experiments are well known in the art. See. e.g., Chick C. Wilson, Neutron Single Crystal Diffraction, 220 Z. Kristallogr. 385-98 (2005) (incorporated by reference herein in its entirety).

Crystal structure data, including particular isotopic ratios, are obtained from neutron diffraction data following routine structure solution and refinement processes. Structure solution is carried out using one of several methods, including direct methods and Patterson methods. For convenience, atomic coordinates from prior single crystal X-ray diffraction experiments may be used as a starting point for structure refinement using neutron diffraction data; this approach permits additional refinement of atomic positions, including hydrogen and deuterium positions. Refinement is conducted using full-matrix least-squares methods to achieve optimal agreement between the observed diffraction intensities and those calculated from the structural model. Ideally, full anisotropic refinement is carried out on all atoms, including the H/D atomic positions of interest. Data collection, structure solution and structure refinement methods, both for X-ray and neutron diffraction data, are well known in the art. See, e.g., Chick C. Wilson, Single Crystal Neutron Diffraction from Molecular Materials (World Scientific Publishing Co. 2000); George H. Stout & Lyle H. Jensen, X-Ray Structure Determination: A Practical Guide (John Wiley & Sons, Inc. 2nd ed. 1989) (both of which are incorporated herein in their entireties).

The isotopic ratio for a particular position on a deuterated compound is calculated by examining the neutron scattering cross sections for the H/D atomic position of interest. The scattering cross section is obtained as part of the refinement process discussed above. An example of determining the isotopic ratio for a partially deuterated compound is provided by G. A. Jeffrey et al., *Neutron Diffraction Refinement of Partially Deuterated β-D-Arabinopyranose and α-L-Xylopyranose at 123 K*, B36 Acta Crystallographica 373-77 (1980) (incorporated by reference herein in its entirety). Jeffrey et al. used single-crystal neutron diffraction to determine the percentage deuterium substitution for hydroxyl groups on two sugar compounds of interest. Employing the methods discussed by Jeffrey et al., one may similarly ascertain the isotopic ratio for a particular H/D position on a deuterated compound.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A process for the preparation of an enantiomerically enriched or enantiomerically pure compound of Formula (I):

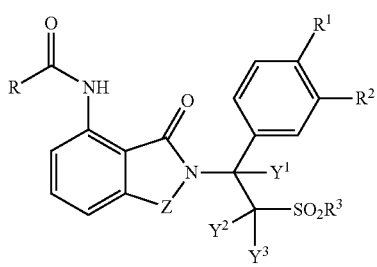

(I)

or a salt, stereoisomer, or isotopologue thereof, wherein:
$R^1$ and $R^2$ are each independently hydrogen, halogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, —$CF_3$, $(C_3-C_{18})$cycloalkyl-$(C_1-C_6)$alkoxy, or an isotopologue thereof;
$R^3$ is $(C_1-C_6)$alkyl, or an isotopologue thereof;
R is $(C_1-C_3)$alkyl, $(C_3-C_6)$cycloalkyl, or an isotopologue thereof;
Z is C=O, methylene, or an isotopologue thereof; and
$Y^1, Y^2$, and $Y^3$ are independently hydrogen or deuterium;
Comprising the step of
(a) reducing an enamine of Formula (II):

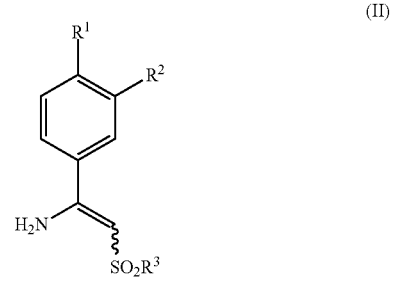

(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

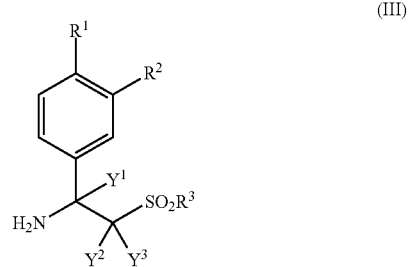

(III)

or a salt or isotopologue thereof; wherein deuterium gas or a solvent containing exchangeable deuterium for proton-deuterium exchange or both is used.

2. The process of claim 1 for the preparation of an enantiomerically enriched or enantiomerically pure compound of Formula (I-a):

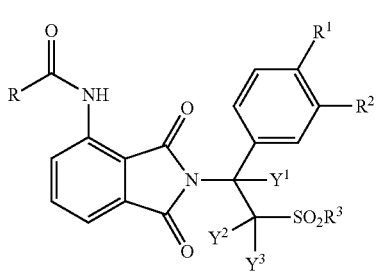

(I-a)

or a salt, stereoisomer, or isotopologue thereof, wherein:
  $R^1$ and $R^2$ are each independently hydrogen, halogen, substituted or unsubstituted $(C_1$-$C_6)$alkyl, substituted or unsubstituted $(C_1$-$C_6)$alkoxy, $(C_3$-$C_{18})$cycloalkyl, $(C_3$-$C_6)$cycloalkoxy, cyano, —$CF_3$, $(C_3$-$C_{18})$cycloalkyl-$(C_1$-$C_6)$alkoxy, or an isotopologue thereof;
  $R^3$ is $(C_1$-$C_6)$alkyl, or an isotopologue thereof;
  R is $(C_1$-$C_3)$alkyl, $(C_3$-$C_6)$cycloalkyl, or an isotopologue thereof; and
  $Y^1$, $Y^2$, and $Y^3$ are independently hydrogen or deuterium;
comprising the steps of
  (a) reducing an enamine of Formula (II):

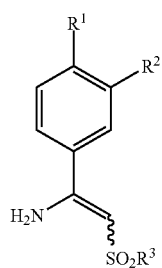
(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

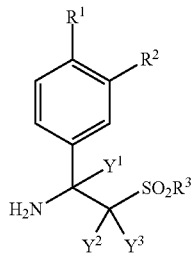
(III)

or a salt or isotopologue thereof; wherein deuterium gas or a solvent containing exchangeable deuterium for proton-deuterium exchange or both is used; and
  (b) reacting the enantiomerically enriched or enantiomerically pure aminosulfone of Formula (III), or a salt or isotopologue thereof, with a compound of Formula (V):

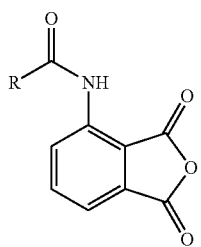
(V)

or a salt or isotopologue thereof, to form the enantiomerically enriched or enantiomerically pure compound of Formula (I-a), or a salt or isotopologue thereof.

3. The process of claim 1 for the preparation of an enantiomerically enriched or enantiomerically pure compound of Formula (I-b):

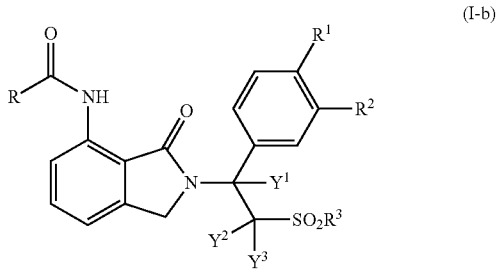
(I-b)

or a salt, stereoisomer, or isotopologue thereof, wherein:
  $R^1$ and $R^2$ are each independently hydrogen, halogen, substituted or unsubstituted $(C_1$-$C_6)$alkyl, substituted or unsubstituted $(C_1$-$C_6)$alkoxy, $(C_3$-$C_{18})$cycloalkyl, $(C_3$-$C_6)$cycloalkoxy, cyano, —$CF_3$, $(C_3$-$C_{18})$cycloalkyl-$(C_1$-$C_6)$alkoxy, or an isotopologue thereof;
  $R^3$ is $(C_1$-$C_6)$alkyl, or an isotopologue thereof;
  R is $(C_1$-$C_3)$alkyl, $(C_3$-$C_6)$cycloalkyl, or an isotopologue thereof; and
  $Y^1$, $Y^2$, and $Y^3$ are independently hydrogen or deuterium;
comprising the steps of
  (a) reducing an enamine of Formula (II):

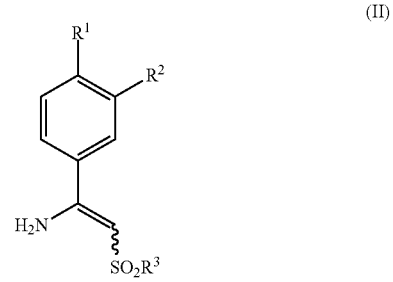
(II)

or a salt or isotopologue thereof, via hydrogenation with hydrogen gas or deuterium gas, in a solvent, and in the presence of (1) a metal catalyst and a chiral ligand or (2) a chiral metal catalyst/ligand complex to form an enantiomerically enriched or enantiomerically pure aminosulfone of Formula (III):

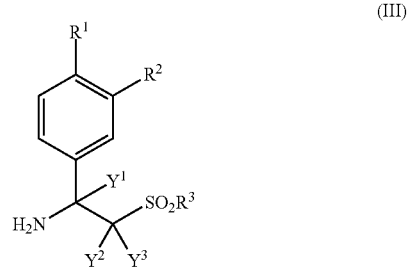
(III)

or a salt or isotopologue thereof; wherein deuterium gas or a solvent containing exchangeable deuterium for proton-deuterium exchange or both is used;

(b) reacting the enantiomerically enriched or enantiomerically pure aminosulfone of Formula (III), or a salt or isotopologue thereof, with a compound of Formula (VI):

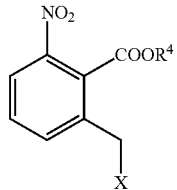
(VI)

or a salt or isotopologue thereof, wherein R⁴ is (C₁-C₃)alkyl, and X is halogen, to form an enantiomerically enriched or enantiomerically pure compound of Formula (VII):

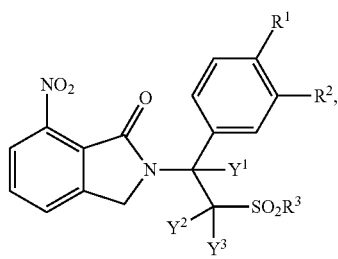
(VII)

or a salt or isotopologue thereof;

(c) reducing the enantiomerically enriched or enantiomerically pure compound of Formula (VII), or a salt or isotopologue thereof, to form an enantiomerically enriched or enantiomerically pure compound of Formula (VIII):

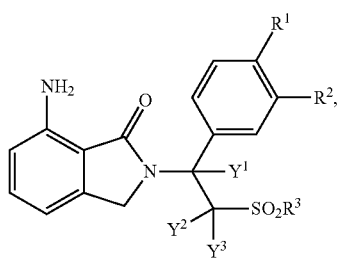
(VIII)

or a salt or isotopologue thereof; and (d) reacting the enantiomerically enriched or enantiomerically pure compound of Formula (VIII), or a salt or isotopologue thereof, with an acid chloride RCOCl, or an isotopologue thereof, to form the enantiomerically enriched or enantiomerically pure compound of Formula (I-b), or a salt or isotopologue thereof.

4. The process of claim 1, wherein Y¹ is hydrogen or deuterium; and Y² and Y³ are both hydrogen or both deuterium.

5. The process of claim 4, wherein Y¹ is hydrogen or deuterium; and Y² and Y³ are both hydrogen or both deuterium, wherein not all of Y¹, Y², and Y³ are hydrogen.

6. The process of claim 1, wherein the enamine of Formula (II), or a salt or isotopologue thereof, is synthesized by reacting a nitrile of Formula (IV):

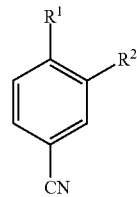
(IV)

or an isotopologue thereof, with LiCH₂SO₂R³, or an isotopologue thereof.

7. The process of claim 1, wherein R¹ and R² are substituted or unsubstituted (C₁-C₆)alkoxy, or an isotopologue thereof.

8. The process of claim 7, wherein R¹ is OMe enriched with 0, 1, 2, or 3 deuterium, and R² is OEt enriched with 0, 1, 2, 3, 4, or 5 deuterium.

9. The process of claim 8, wherein R¹ is OCD₃, and R² is OEt.

10. The process of claim 8, wherein R¹ is OCD₃, and R² is OCD₂CD₃.

11. The process of claim 1, wherein R³ is Me enriched with 0, 1, 2, or 3 deuterium.

12. The process of claim 1, wherein the enamine of Formula (II), or a salt or isotopologue thereof, is an enamine of Formula (II-a):

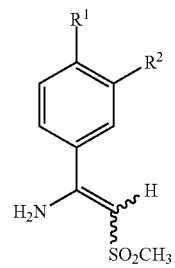
(II-a)

or a salt or isotopologue thereof, wherein the enamine of Formula (II-a), or a salt or isotopologue thereof, is synthesized by reacting a nitrile of Formula (IV):

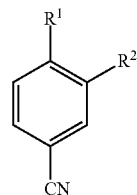
(IV)

or an isotopologue thereof, with CH₃SO₂CH₃ and n-BuLi.

13. The process of claim 1, wherein the enamine of Formula (II), or a salt or isotopologue thereof, is an enamine of Formula (II-b):

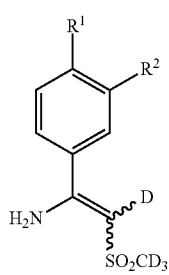
(II-b)

or a salt or isotopologue thereof, wherein the enamine of Formula (II-b), or a salt or isotopologue thereof, is synthesized by reacting a nitrile of Formula (IV):

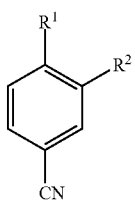
(IV)

or an isotopologue thereof, with $CD_3SO_2CD_3$ and n-BuLi.

14. The process of claim 1, wherein R is methyl enriched with 0, 1, 2, or 3 deuterium or cyclopropyl enriched with 0, 1, 2, 3, 4, or 5 deuterium.

15. The process of claim 1, wherein the hydrogenation in step (a) occurs with hydrogen gas.

16. The process of claim 1, wherein the hydrogenation in step (a) occurs with deuterium gas.

17. The process of claim 1, wherein the hydrogenation in step (a) occurs in a solvent containing exchangeable proton for proton-deuterium exchange.

18. The process of claim 17, wherein the solvent containing exchangeable proton for proton-deuterium exchange is 2,2,2-trifluoroethanol.

19. The process of claim 1, wherein the hydrogenation in step (a) occurs in a solvent containing exchangeable deuterium for proton-deuterium exchange.

20. The process of claim 19, wherein the solvent containing exchangeable deuterium for proton-deuterium exchange is 2,2,2-trifluoroethanol-d$^1$.

21. The process of claim 1, wherein the hydrogenation in step (a) occurs in a solvent containing neither exchangeable proton nor exchangeable deuterium for proton-deuterium exchange.

22. The process of claim 1, wherein the metal catalyst is $Rh(cod)_2OTf$.

23. The process of claim 1, wherein the chiral ligand is (S,R)-t-Bu Josiphos.

24. The process of claim 1, wherein the compound of Formula (I) is

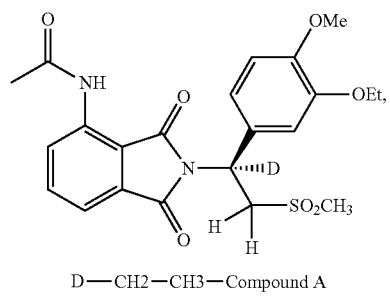

D—CH2—CH3—Compound A

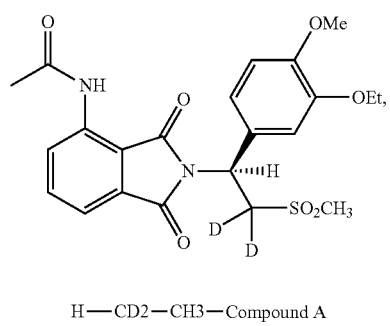

H—CD2—CH3—Compound A

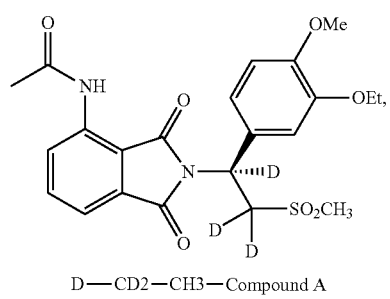

D—CD2—CH3—Compound A

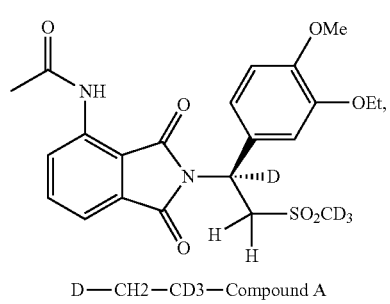

D—CH2—CD3—Compound A

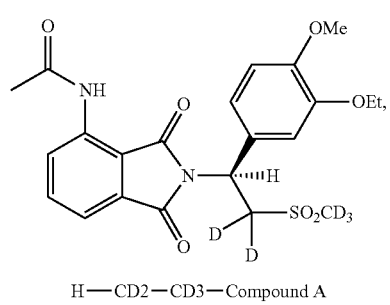

H—CD2—CD3—Compound A

-continued
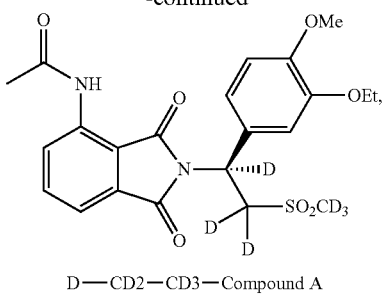
D—CD2—CD3—Compound A
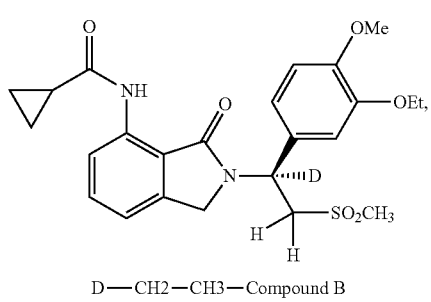
D—CH2—CH3—Compound B
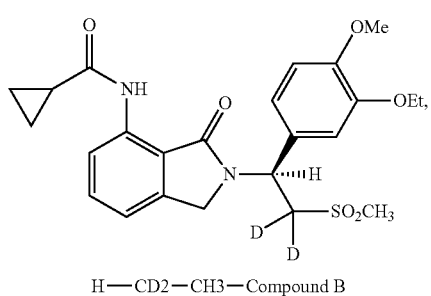
H—CD2—CH3—Compound B
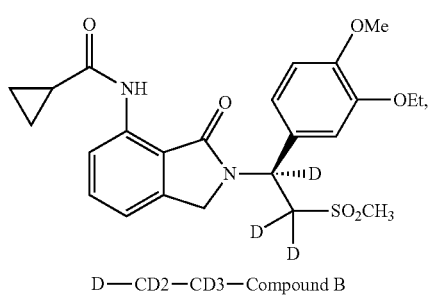
D—CD2—CD3—Compound B
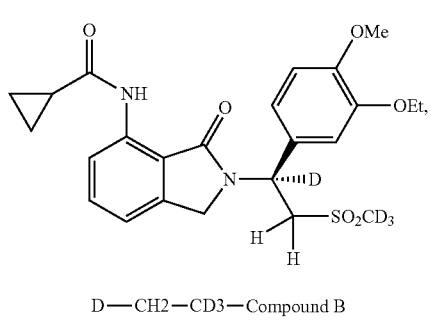
D—CH2—CD3—Compound B
-continued
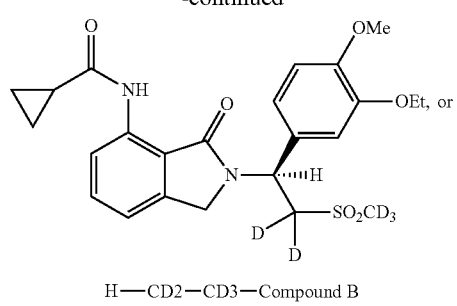
H—CD2—CD3—Compound B
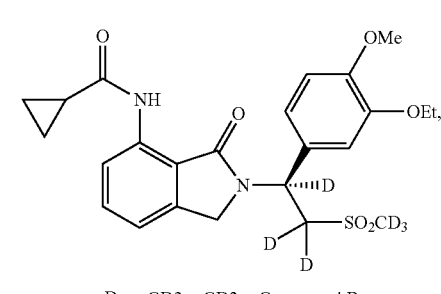
D—CD2—CD3—Compound B
or a salt, stereoisomer, or isotopologue thereof.
25. The process of claim 1, wherein the compound of Formula (I) is
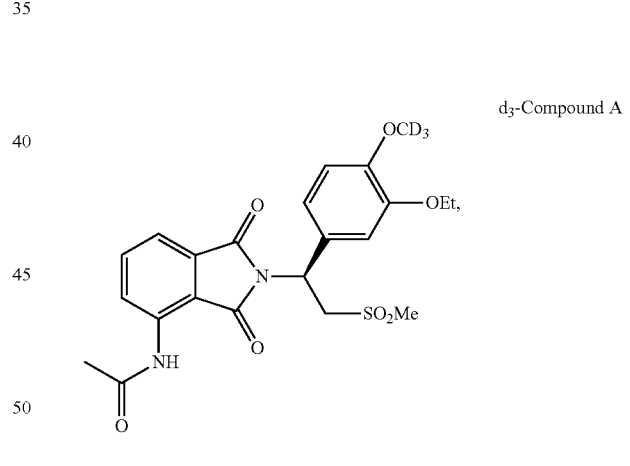
d$_3$-Compound A
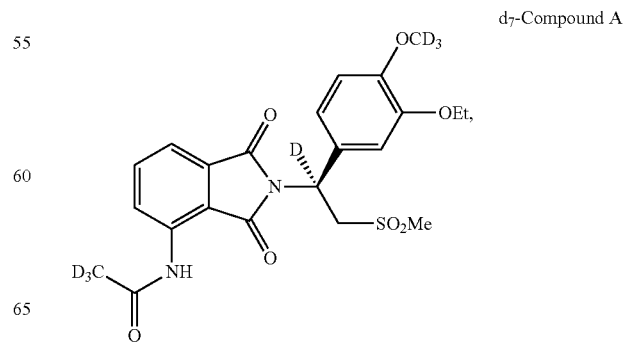
d$_7$-Compound A

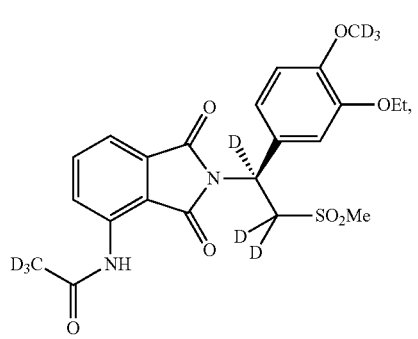
d9-Compound A
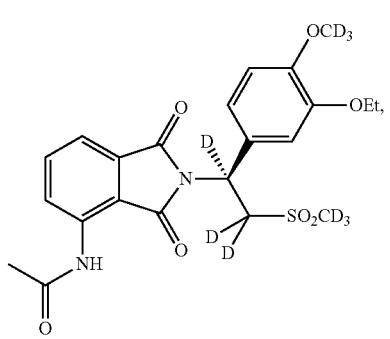
d9-Compound A
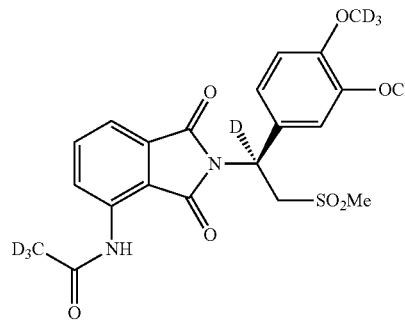
d12-Compound A
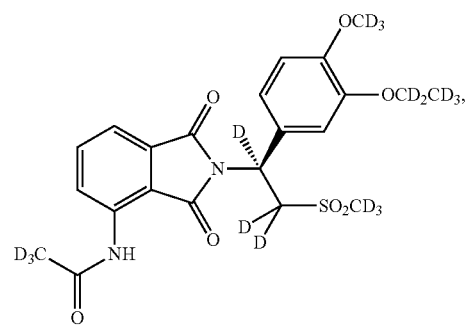
d17-Compound A
or a salt, stereoisomer, or isotopologue thereof.
* * * * *